US009932393B2

(12) United States Patent
Krumlauf et al.

(10) Patent No.: US 9,932,393 B2
(45) Date of Patent: Apr. 3, 2018

(54) ANTIBODY THAT BINDS MURINE WISE PROTEIN

(71) Applicant: Stowers Institute for Medical Research, Kansas City, MO (US)

(72) Inventors: Robb Krumlauf, Mission Hills, KS (US); Debra Ellies, Kansas City, MO (US)

(73) Assignee: Stowers Institute for Medical Research, Kansas City, MO (US)

( * ) Notice: Subject to any disclaimer, the term of this patent is extended or adjusted under 35 U.S.C. 154(b) by 406 days.

(21) Appl. No.: 14/564,979

(22) Filed: Dec. 9, 2014

(65) Prior Publication Data

US 2015/0152173 A1   Jun. 4, 2015

Related U.S. Application Data

(60) Continuation of application No. 13/950,553, filed on Jul. 25, 2013, now abandoned, which is a continuation of application No. 13/030,863, filed on Feb. 18, 2011, now Pat. No. 8,519,105, which is a division of application No. 12/459,764, filed on Jul. 6, 2009, now Pat. No. 7,914,786, which is a division of application No. 11/613,658, filed on Dec. 20, 2006, now Pat. No. 7,585,501, which is a continuation-in-part of application No. 11/508,701, filed on Aug. 23, 2006, now Pat. No. 7,893,218, and a continuation-in-part of application No. 10/464,368, filed on Jun. 16, 2003, now abandoned.

(60) Provisional application No. 60/710,803, filed on Aug. 23, 2005.

(51) Int. Cl.
| | |
|---|---|
| C07K 16/18 | (2006.01) |
| C07K 16/26 | (2006.01) |
| C07K 14/47 | (2006.01) |
| C07K 14/705 | (2006.01) |
| C07K 16/30 | (2006.01) |
| C07K 14/575 | (2006.01) |
| A61K 38/00 | (2006.01) |
| A61K 48/00 | (2006.01) |
| A61K 39/00 | (2006.01) |

(52) U.S. Cl.
CPC ............. *C07K 16/18* (2013.01); *C07K 14/47* (2013.01); *C07K 14/4702* (2013.01); *C07K 14/705* (2013.01); *C07K 16/30* (2013.01); *A01K 2217/05* (2013.01); *A01K 2217/075* (2013.01); *A01K 2227/105* (2013.01); *A61K 38/00* (2013.01); *A61K 48/00* (2013.01); *A61K 2039/505* (2013.01); *C07K 14/575* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,196,265 | A | 4/1980 | Koprowski et al. |
| 4,673,641 | A | 6/1987 | George et al. |
| 4,683,195 | A | 7/1987 | Mullis et al. |
| 4,683,202 | A | 7/1987 | Mullis |
| 5,780,263 | A | 7/1998 | Hastings et al. |
| 5,840,832 | A * | 11/1998 | Ono .................. C07K 14/4703 435/320.1 |
| 5,855,866 | A | 1/1999 | Thorpe et al. |
| 5,877,289 | A | 3/1999 | Thorpe et al. |
| 5,965,132 | A | 10/1999 | Thorpe et al. |
| 6,004,555 | A | 12/1999 | Thorpe et al. |
| 6,051,230 | A | 4/2000 | Thorpe et al. |
| 6,395,511 | B1 | 5/2002 | Brunkow et al. |
| 6,489,445 | B1 | 12/2002 | Brunkow et al. |
| 6,495,736 | B1 | 12/2002 | Brunkow et al. |
| 6,803,453 | B1 | 10/2004 | Brunkow et al. |
| 6,875,570 | B2 | 4/2005 | Gerlach et al. |
| 7,381,409 | B2 | 6/2008 | Winkler et al. |
| 7,572,899 | B2 | 8/2009 | Brunkow et al. |
| 7,578,999 | B2 | 8/2009 | Winkler et al. |
| 7,585,501 | B2 | 9/2009 | Krumlauf et al. |
| 7,893,218 | B2 | 2/2011 | Krumlauf et al. |
| 7,914,786 | B2 | 3/2011 | Krumlauf et al. |
| 7,968,301 | B2 | 6/2011 | Krumlauf et al. |
| 8,168,761 | B2 | 5/2012 | Krumlauf et al. |
| 8,173,125 | B2 | 5/2012 | Krumlauf et al. |
| 8,519,105 | B2 | 8/2013 | Krumlauf et al. |
| 8,546,545 | B2 | 10/2013 | Krumlauf et al. |

(Continued)

FOREIGN PATENT DOCUMENTS

| | | |
|---|---|---|
| EP | 90/404097 | 6/1990 |
| WO | 90/004036 | 4/1990 |

(Continued)

OTHER PUBLICATIONS

GenBank Accession No. AAN08617, no author listed, 1 page as printed, available on-line at https://www.ncbi.nlm.nih.gov/protein/27923584/ with a public release date of Jan. 28, 2003.*
Publication PT2-011-1, "Antipeptide Antibodies", no author listed, pp. 1-12; available on-line at http://www.mimotopes.com/files/editor_upload/File/PeptidesAndAntibodies/PT2011-1-Antipeptide-Antibodies.PDF with a date of Feb. 1, 2002 per Google.*
Pierce Chemical Co., Pierce Catalog and Handbook, 1994-1995. Pierce Chemical Co., Rockford, Ill.
Kuby Immunology, W. H. Freeman (3rd Ed), 1997.
Kostelny, S.A., et al., Formation of a bispecific antibody by the use of leucine zippers, The Journal of Immunology, (Mar. 1992) 148:(5), 1547-1553.

(Continued)

*Primary Examiner* — Zachary Howard
(74) *Attorney, Agent, or Firm* — Bryan Cave LLP

(57) ABSTRACT

The present invention relates to methods and compositions for the prevention and treatment of renal damage. The invention provides protein-based renal therapeutic agents for administration to subjects in order to prevent or treat renal degeneration or damage.

6 Claims, 1 Drawing Sheet

(56) References Cited

U.S. PATENT DOCUMENTS

| | | |
|---|---|---|
| 2003/0166247 A1 | 9/2003 | Brunkow et al. |
| 2003/0229041 A1 | 12/2003 | Sutherland et al. |
| 2004/0023356 A1 | 2/2004 | Krumlauf et al. |
| 2004/0158045 A1 | 8/2004 | Brunkow et al. |
| 2005/0106683 A1 | 5/2005 | Winkler et al. |
| 2007/0072797 A1 | 3/2007 | Robinson et al. |
| 2007/0110747 A1 | 5/2007 | Paszty et al. |
| 2007/0292444 A1 | 12/2007 | Krumlauf et al. |
| 2007/0298038 A1 | 12/2007 | Krumlauf et al. |
| 2008/0160060 A1 | 7/2008 | Ellies |
| 2010/0015159 A1 | 1/2010 | Krumlauf et al. |
| 2012/0014959 A1 | 1/2012 | Krumlauf et al. |
| 2012/0016108 A1 | 1/2012 | Krumlauf et al. |
| 2012/0022237 A1 | 1/2012 | Krumlauf et al. |
| 2013/0022613 A1 | 1/2013 | Krumlauf et al. |
| 2013/0023651 A1 | 1/2013 | Krumlauf et al. |
| 2013/0209474 A1 | 8/2013 | Krumlauf et al. |

FOREIGN PATENT DOCUMENTS

| | | |
|---|---|---|
| WO | 90/010077 | 9/1990 |
| WO | 92/002190 | 2/1992 |
| WO | 93/011161 | 6/1993 |
| WO | WO 00/32773 | 6/2000 |
| WO | WO 01/92308 | 12/2001 |
| WO | WO 02/24888 | 3/2002 |

OTHER PUBLICATIONS

Holliger, et al., Diabodies: small bivalent and bispecific antibody fragments, Proc Natl Acad Sci U S A. Jul. 15, 1993; 90(14):6444-8.
Gruber, M. et al., Efficient tumor cell lysis mediated by a bispecific single chain antibody expressed in *Escherichia coli*, J Immunol. Jun. 1, 1994;152(11):5368-74.
Zhu, S. et al., Remodeling domain interfaces to enhance heterodimer formation, Protein Science, (1997), 6:781-788, Cambridge Univ. Press.
Hu, S.Z. et al, (1996), Minibody: A Novel Engineered Anti-Carcinoembryonic Antigen Antibody Fragment (Single-Chain Fv-CH3) Which Exhibits Rapid, High-Level Targeting of Xenografts1Cancer Res. 56:3055-3061, Jul. 1, 1996.
Adams, G.P. et al., Highly Specific in Vivo Tumor Targeting by Monovalent and Divalent Forms of 741F8 Anti-c-erbB-2 SingleiChair Fv, Cancer Research 53. 4026-4034, Sep. 1, 1993.
McCartney, J.E., et al., Engineering disulfide-linked single-chain Fv dimers [(sFv')2] with improved solution and targeting properties: anti-digoxin 26-10 (sFv')2 and anti-c-erbB-2 741F8 (sFv')2 made by protein folding and bonded through C-terminal cysteinyl peptides, Protein Engineering, Design and Selection, vol. 8, Issue 3, Mar. 1, 1995, pp. 301.
Huse, et al, Generation of a Large Combinatorial Library of the Immunoglobulin Repertoire in Phage Lambda, Science 246:1275-1281 (1989).
Ward et al, Binding activities of a repertoise of single immunoglobulin variable domains secreted from *Escherichia coli*, Nature 341: 544-546 (1989).
Vaughan T., et al., Human Antibodies with Sub-nanomolar Affinities Isolated from a Large Non-immunized Phage Display Library, Nature Biotechnology, vol. 14, Mar. 1, 1996, pp. 309-314.
Harlow, E, et al., Antibodies: A Laboratory Manual, Cold Spring Harbor Laboratory, 1988.
Smith & Waterman, Adv. Appl. Math., J. Mol. Biol., 2:482, 1981.
Needleman & Wunsch, J. Mol. Biol., 48:443, 1970.
Pearson & Lipman, Improved tools for biological sequence comparison, Proc Natl Acad Sci U S A. Apr. 1988;85 (8):2444-8.
Ausubel, F. M., et al., Current Protocols in Molecular Biology, eds., 1995 supplement; and, Current Protocols in Molecular Biology,1990, pp. 8.2.8 to 8.2.13.
Altschul, S. F., et al., Gapped BLAST and PSI-BLAST: a new generation of protein database search programs, Nucleic Acids Research, 1997, vol. 25, No. 17 3389-3402.
Altschul, S. F., et al., Basic Local Alignment Search Tool. Journal of Molecular Biology 215, 403-410 (1990).
Henikoff S., et al., Amino acid substitution matrices from protein blocks, Proc. Natl. Acad. Sci. U S A. Nov. 15, 1992;89(22):10915-9.
Karlin, S., et al., Applications and statistics for multiple high-scoring segments in molecular sequences, Proc. Natl. Acad. Sci. USA, vol. 90, pp. 5873-5877, Jun. 1993.
Brenner & Lazarus, Harrison's Principles of Internal Medicine, 13th ed., 1994.
Isselbacher, K. J. et al., (Eds), Harrison's Principles of Internal Medicine, Ninth Edition—Published by McGraw-Hill Book Co., NY (1982).
Barany, G., et al., Solid Phase Peptide Synthesis in Peptides, vol. 2, Academic Press, NY, NY, pp. 100-118 (1980).
Wilson., G.L., et al., cDNA Cloning of the B Cell Membrane Protein CD22: A Mediator of B-B Cell Interactions, J. Exp. Med., 173:137, 1991.
Wilson., G.L., et al., Genomic structure and chromosomal mapping of the human CD22 gene, J Immunol Jun. 1, 1993, 150 (11) 5013-5024.
Wosnick, M.A., Rapid construction of large synthetic genes: total chemical synthesis of two different versions of the bovine prochymosin gene, Gene, vol. 60, Issue 1, 1987, pp. 115-127.
Ausabel, et al., (eds.), Short Protocols in Molecular Biology, 3rd Ed., pp. 8-8 to 8-9, John Wiley & Sons, 1995.
Adang, M. J., et al., The reconstruction and expression of a *Bacillus thuringiensis* cryIIIA gene in protoplasts and potato plants, Plant Molecular Biology, Mar. 1993, vol. 21, Issue 6, pp. 1131-1145.
Bambot, S.B., et al., Efficient total gene synthesis of 1.35-kb hydrid alpha-lytic protease gene using the polymerase chain reaction, Genome Res., 1993, vol. 2: 266-271.
Dillon, P.J., Use of Polymerase Chain Reaction for the Rapid Construction of Synthetic Genes, PCR Protocols pp. 263-268, Part of the Methods in Molecular Biology book series (MIMB, vol. 15), Abstract.
Goding, J.W., Monoclonal Antibodies: Principles and Practice, Third Ed., Academic Press, pp. 65-66, 1986.
Campbell, et al., In: Monoclonal Antibody Technology, Laboratory Techniques in Biochemistry and Molecular Biology, Burden and Von Knippenberg (Eds.), Elseview, Amsterdam, 13:71-74/75-83, 1984.pp. 75-83, 1984.
Liu, A.Y., et al., I. Chimeric mouse-human IgGi antibody that can mediate lysis of cancer cells, Proc. Natl. Acad. Sci. USA, vol. 84, 3439-3443, 1987.
Kabat et al, Sequences of Proteins of Immunological Interest, N.I.H. publication No. 91-3242, (1983).
Zapata, G., et al., Engineering linear F(ab')2 fragments for efficient production in *Escherichia coli* and enhanced antiproliferative activity, Protein Engineering, Design and Selection, vol. 8, Issue 10, Oct. 1, 1995.
Current Protocols in Cell Biology, Unit 10, 2003 and Unit 20, 2004, Pub. Wiley & Sons, Inc.
Remington's Pharmaceutical Sciences, 19th Ed., 1995.
Brenner & Lazarus, Harrison's Principles of Internal Medicine, 13th Ed., Isselbacher et al., eds., McGraw Hill Text, NY, 1994.
Sherwood, J.K., et al., Controlled Antibody Delivery Systems, Nature Biotechnology 10, 1446-1449 (1992).
Saltzman, W. M., et al., Transport rates of proteins in porous materials with known microgeometry, Biophys. J. Jan. 1989; 55(1): 163-171.
Hillman, GG., Experimental animal models for the study of therapeutic approaches in renal cell carcinoma, In Vivo, 1994: 8:77-80.
Sayers, T.J., et al., Antitumor Effects of α-Interferon and γ-Interferon on a Murine Renal Cancer (Renca) in Vitro and in Vivo, Cancer Research, 50: 5414-5420, 1990.
Salup, R.R., et al., Adjuvant Immunotherapy of Established Murine Renal Cancer by Interleukin 2-stimulated Cytotoxic Lymphocytes, Cancer Research 46, 3358-3363, Jul. 1986.
Aberg et al., "Phenotypic Changes in Dentition of Runx2 Homozygote-Null Mutant Mice," J. Histochem. Cytochem., vol. 52, pp. 131-139 (2004).

(56) References Cited

OTHER PUBLICATIONS

Abreu, J. G., Ketpura, N. I., Reversade, B. & De Robertis, E. M. Connective-tissue growth factor (CTGF) modulates cell signalling by BMP and TGF-beta. Nat Cell Biol. 4, 599-604 (2002).
Albertsen et al., "A physical map and candidate genes in the BRCA1 region on chromosome 17q12-21," Nature Genetics, 7:472-479 (1994).
Amaya et al., "Expression of a Dominant Negative Mutant of the FGF Receptor Disrupts Mesoderm Formation in Xenopus Embryos," Cell, vol. 66, pp. 257-270 (1991).
Aubin et al., "Monoclonal Antibodies as Tools for Studying the Osteoblast Lineage," Microscopy Research and Technique, vol. 33, pp. 128-140 (1996).
Axelrod et al., "Differential Recruitment of Dishevelled Provides Signaling Specificity in the Planar Cell Polarity and Wingless Signaling Pathways," Genes & Development, vol. 12, pp. 2610-2622 (1998).
Bachiller et al., "The Organizer Factors Chordin and Noggin Are Required for Mouse Forebrain Development," Nature, vol. 403, pp. 658-661 (2000).
Baker et al., "Wnt Signaling in Xenopus Embryos Inhibits Bmp4 Expression and Activates Neural Development," Genes & Development, vol. 13, pp. 3149-3159 (1999).
Balemans et al., "Localization of the Gene for Sclerosteosis to the van Buchem Disease-Gene Region on Chromosome 17q12-q21," Am. J. Hum. Genet., 64:1661-1669 (1999).
Balemans et al., "Extracellular Regulation of BMP Signaling in Vertebrates: A Cocktail of Modulators," Developmental Biology, vol. 250, pp. 231-250 (2002).
Balemans et al., "Increased Bone Density in Sclerosteosis Is Due to the Deficiency of a Novel Secreted Protein (SOST)," Human Molecular Genetics, vol. 10, No. 5, pp. 537-543 (2001).
Balemans et al., "Lack of Association Between the SOST Gene and Bone Mineral Density in Perimenopausal Women: Analysis of Five Polymorphisms," Bone, vol. 31, No. 4, pp. 515-519 (2002).
Balmain et al., "Cancer Resistance Genes in Mice: Models for the Study of Tumour Modifiers," Trends in Genetics, vol. 14, No. 4, pp. 139-144 (1998).
Beddington et al., "Anterior Patterning in Mouse," Trends in Genetics, vol. 14, pp. 277-284 (1998).
Beddington et al., "Axis Development and Early Asymmetry in Mammals," Cell, vol. 96, pp. 195-209 (1999).
Beighton, "Sclerosteosis," Journal of Medical Genetics, vol. 25, pp. 200-203 (1988).
Benzing et al., "Wnt Signaling in Polycystic Kidney Disease," J. American Society of Nephrology, vol. 18, pp. 1389-1398 (2007).
Blumberg et al., "An Essential Role for Retinoid Signaling in Anteroposterior Neural Patterning," Development, vol. 124, pp. 373-379 (1997).
Bork, "The Modular Architecture of a New Family of Growth Regulators Related to Connective Tissue Growth Factor," FEBS Letters, vol. 327, No. 2, pp. 125-130 (1993).
Bourguignon et al., "XBF-1, A Winged Helix Transcription Factor With Dual Activity, Has a Role in Positioning Neurogenesis in Xenopus Competent Ectoderm," Development, vol. 125, pp. 4889-4900 (1998).
Boyden et al., "High Bone Density Due to a Mutation in LOL-Receptor-Related Protein 5," The New England Journal of Medicine, vol. 346, No. 20, pp. 1513-1521 (2002).
Bradley et al., "Modifying the Mouse: Design and Desire," Bio/Technology, 10:534-539 (1992).
Bradley et al., "Different Activities of the Frizzled-Rotated Proteins frzb2 and sizzled2 During Xenopus Anteroposterior Patterning," Developmental Biology, vol. 227, pp. 118-132 (2000).
Brannon et al., "A β-catentin/XTcf-3 Complex Binds to the Slamois Promoter to Regulate Dorsal Axis Specification in Xenopus," Genes & Development, vol. 11, pp. 2359-2370 (1997).
Bruder et al., "Monoclonal Antibodies Reactive With Human Osteogenic Cell Surface Antigens," Bone, vol. 21, No. 3, pp. 225-235 (1997).

Brunkow et al., "Bone Dysplasia Sclerosteosis Results From Loss of the SOST Gene Product, A Novel Cysteine Knot-Containing Protein," Am. J. Hum. Genet., vol. 68, pp. 577-589 (2001).
Cadigan et al., "Wnt Signaling: A Common Theme in Animal Development," Genes & Development, vol. 11, pp. 3286-3305 (1997).
Cameron, "Recent Advances in Transgenic Technology," Molec. Biol., vol. 7, pp. 253-265 (1997).
Campbell et al., "Totipotency or Multipotentiality of Cultured Cells: Applications and Progress," Theriogenology, 47:63-72 (1997).
Campbell, Monoclonal Antibody Technology, 1984, Chapter 1, pp. 1-32.
Capdevila et al., "Control of Dorsoventral Somite Patterning by Wnt-1 and β-Catenin," Developmental Biology, vol. 193, pp. 182-194 (1998).
Capecchi, "Targeted Gene Replacement," Scientific American, vol. 270, No. 3, pp. 52-59 (1994).
Chan et al., "New paradigm in the treatment of osteoporosis: Wnt pathway proteins and their antagonists," Current Opinion in Investigational Drugs, 8(4):293-298 (2007).
Chen et al., "Thy-1 Antigen Expression by Cells in the Osteoblast Lineage," Journal of Bone and Mineral Research, vol. 14, No. 3, pp. 362-375 (1999).
Christian et al., "Interactions Between Xwnt-8 and Spemann Organizer Signaling Pathways Generate Dorsoventral Pattern in the Embryonic Mesoderm of Xenopus," Genes & Development, vol. 7, pp. 13-28.
Condie et al., "Most of the Homeobox-Containing Xhox 36 Transcripts in Early Xenopus Embryos Cannot Encode a Homeodomain Protein," Molecular and Cellular Biology, vol. 10, pp. 3376-3385 (1990).
Cook et al., "Structural Basis for a Functional Antagonist in the Transforming Growth Factor β Superfamily," J. Biol. Chem., 280(48):40177-186 (2005).
Cox et al., "Caudalization of Neural Fate by Tissue Recombination and bFGF," Development, vol. 121, pp. 4349-4358 (1995).
Danielian et al., "Engrailed-1 as a Target of the Wnt-1 Signalling Pathway in Vertebrate Midbrain Development," Nature, vol. 383, pp. 332-334 (1996).
Dewitt, "Bone and Cartilage," Nature, vol. 423, p. 315 (2003).
Dickinson et al., "Dorsalization of the Neural Tube by the Non-Neural Ectoderm," Development, vol. 121, pp. 2099-2106 (1995).
Doniach, "Planar and Vertical Induction of Anteroposterior Pattern During the Development of Theamphibian Central Nervous System," Journal of Neurobiology, vol. 24, No. 10, pp. 1256-1275 (1993).
Ebisawa et al., "Characterization of Bone Morphogenetic Protein-6 Signaling Pathways in Osteoblast Differentiation," Journal of Cell Science, vol. 112, pp. 3519-3527 (1999).
Ellies et al., "Bone Density Ligand, Sclerostin, Directly Interacts With LRP5 but Not $LRP5^{G1/1V}$ to Modulate Wnt Activity," J. Bone and Mineral Research, vol. 21, pp. 1738-1749 (2006).
Ensini et al., "The Control of Rostrocaudal Pattern in the Developing Spinal Cord: Specification of Motor Neuron Subtype Identity Is Initiated by Signals From Paraxial Mesoderm," Development, vol. 125, pp. 969-982 (1998).
Fagotto et al., "Induction of the Primary Dorsalizing Center in Xenopus by the Wnt/GSK/β-Catenin Signaling Pathway, But Not by Vg1, Activin or Noggin," Development, vol. 124, pp. 453-460 (1997).
Fan et al., "A Role for Siamois in Spemann Organizer Formation," Development, vol. 124, No. 13, pp. 2581-2589 (1997).
Final Office Action dated Apr. 27, 2010 in U.S. Appl. No. 11/508,701 (Paper No. 20100422).
Final Office Action dated May 13, 2010 in U.S. Appl. No. 11/985,836 (Paper No. 20100426).
Fredieu et al., "Xwnt-8 and Lithium Can Act Upon Either Dorsal Mesodermal or Neurectodermal Cells to Cause a Loss of Forebrain in Xenopus Embryos," Developmental Biology, vol. 188, pp. 100-114 (1997).
Fullwood et al., "X Linked Exudative Vitreoretinopathy: Clinical Features and Genetic Linkage Analysis," Br. J. Ophthalmol., vol. 77, pp. 168-170 (1993).

(56) References Cited

OTHER PUBLICATIONS

Gall et al., *Autoradiography and Correlative Imaging* (ed. W.E. Stumpf and H. F. Solomon), pp. 379-399.(Academic Press) (1995).
Gavalas et al., "Retinoid Signalling and Hindbrain Patterning," *Cur. Opin. Genet. Dev.*, vol. 10, pp. 380-386 (2000).
Glinka et al., "Dickkopf-1 is a Member of a New Family of Secreted Proteins and Functions in Head Induction," *Nature*, vol. 391, pp. 357-382 (1998).
Glinka et al., "Head Induction by Simultaneous Repression of Bmp and Wnt Signalling in Xenopus," *Nature*, vol. 389, pp. 517-519 (1997).
Gong et al., "LDL Receptor-Related Protein 5 (LRP5) Affects Bone Accrual and Eye Development," *Cell*, vol. 107, pp. 513-523 (2001).
Gould et al., "Initiation of Rhombomeric Hoxb4 Expression Requires Induction by Somites and a Retinoid Pathway," *Neuron*, vol. 21, pp. 39-51 (1998).
Grapin-Botton et al., "Hox Gene Induction in the Neural Tube Depends on Three Parameters: Competence, Signal Supply and Paralogue Group," *Development*, vol. 124, pp. 849-859 (1997).
Groppe et al., "Structural Basis of BMP Signalling Inhibition by the Cystine Knot Protein Noggin," *Nature*, vol. 420, pp. 636-642 (2002).
Hamburger et al., "A Series of Normal Stages in the Development of the Chick Embryo," *J. Morph.*, vol. 88, pp. 49-92 (1951).
Hamersma et al., "The Natural History of Sclerosteosis," *Clinical Genetics*, vol. 63, pp. 192-197 (2003).
Harada et al., "Control of Osteoblast Function and Regulation of Bone Mass," *Nature*, vol. 423, pp. 349-355.
Harris et al., "Human Fetal Osteoblast Progenitor Cell Lines (hFOB)," http.//www.mayo.edutachcomm/93010.html, visited Jun. 11, 2003.
Hartley et al., "Targeted Gene Expression in Transgenic Xenopus Using the Binary Ga14-UAS System," *Proc. Natl. Acad. Sci.*, vol. 99, No. 3, pp. 1377-1382 (2002).
Hartmann, "Wnt-Signaling and Skeletogenesis," *J. Musculoskel. Neuron Interact.*, vol. 2, No. 3, pp. 274-276 (2002).
He et al., "A Member of the Frizzled Protein Family Mediating Axis Induction by Wnt-5A," *Science*, vol. 275, pp. 1652-1654 (1997).
Heasman et al., "β-Catenin Signaling Activity Dissected in the Early Xenopus Embryo: A Novel Antisense Approach," *Developmental Biology*, vol. 222, pp. 124-134 (2000).
Heisenberg et al., "Silberblick/Wnt11 Mediates Convergent Extension Movements During Zebrafish Gastrulation," *Nature*, vol. 405, pp. 76-81 (2000).
Hemmati-Brivanlou et al., "Follistatin, an Antagonist of Activin, Is Expressed in the Spemann Organizer and Displays Direct Neuralizing Activity," *Cell*, vol. 77, pp. 283-295 (1994).
Hemmati-Brivanlou et al., "Inhibition of Activin Receptor Signaling Promotes Neuralization in Xenopus," *Cell*, vol. 77, pp. 273-281 (1994).
Hemmati-Brivanlou et al., "Vertebrate Embryonic Cells Will Become Nerve Cells Unless Told Otherwise," *Cell*, vol. 88, pp. 13-17 (1997).
Hemmati-Brivanlou, "Vertebrate Neural Induction," *Annual Review Neuroscience*, vol. 20, pp. 43-60 (1997).
Hoffman et al., "BMP Signaling Pathways in Cartilage and Bone Formation," *Critical Review in Eukaryotic Gene Expression*, 11(1-3):23-45 (2001).
Hoppler et al., *Expression of a Dominant-Negative Wnt Blocks Induction of MyoD in Xenopus Embryos*, Genes & Development, vol. 10, pp. 2805-2817 (1996).
Hoppler, "Wnt Signalling in Xenopus Development," http://www.personal.dundee.ac.uk/—sphopple/research.html, visited on May 1, 2002.
Houdebine, "Production of Pharmaceutical Proteins From Transgenic Animals," *J. Biotech*, vol. 34, pp. 269-287 (1994).
Houghten et al., "New Approaches to Immunization", *Vaccines 86*, Cold Spring Harbor Laboratory, p. 21-25, 1986.
Hsieh et al., "A New Secreted Protein That Binds to Wnt Proteins and Inhibits Their Activities," *Nature*, vol. 398, pp. 431-436 (1999).
Hsu et al., "The Xenopus Dorsalizing Factor Gremlin Identifies a Novel Family of Secreted Proteins That Antagonize BMP Activities," *Mol. Cell*, vol. 1, pp. 673-683 (1998).
Itasaki et al., "Reprogramming Hox Expression in the Vertebrate Hindbrain: Influence of Paraxial Mesoderm and Rhombomere Transposition," *Neuron*, vol. 18, pp. 487-500 (1996).
Itasaki et al., "Wise, A Context-Dependent Activator and Inhibitor of Wnt Signaling," *Development*, vol. 130, pp. 4295-4305 (2003).
Itoh et al., *Axis Determination by Inhibition of Wnt Signaling in Xenopus*, Genes & Development, vol. 13, pp. 2328-2338 (1999).
Itoh et al., "Graded Amounts of Xenopus Disheveled Specify Discrete Anteroposterior Cell Fates in Prospective Ectoderm," *Mechanisms of Development*, vol. 61, pp. 113-125 (1997).
Itoh et al., "Specific Modulation of Ectodermal Cell Fates in Xenopus Embryos by Glycogen Syntase Kinase," *Development*, vol. 121, pp. 3979-3988 (1995).
Ivkovic et al., "Connective Tissue Growth Factor Coordinates Chondrogenesis and Angiogenesis During Skeletal Development," *Development*, vol. 130, pp. 2779-2791 (2003).
Jena et al., "BMP7 Null Mutation in Mice: Developmental Defects in Skeleton, Kidney, and Eye," *Experimental Cell Research*, vol. 230, pp. 28-37 (1997).
Jones et al., "An Overview of Xenopus Development," *Methods in Molecular Biology*, vol. 97, pp. 331-340 (1999).
Jones et al., "Wholemount in Situ Hybridization to Xenopus Embryos," *Methods in Molecular Biology*, vol. 97, pp. 635-640 (1999).
Joyner, "Engrailed, Wnt and Pax Genes Regulate Midbrain-Hindbrain Development, "*Trends in Genetics*, vol. 12, No. 1, pp. 15-20 (1996).
Kadkhodayan et al., "Cloning, Expression, and One-Step Purification of the Minimal Essential Domain of the Light Chain of Botulinum Neurotoxin Type A," *Protein Expression and Purification*, vol. 19, pp. 125-130 (2000).
Karsenty et al., *Reaching a Genetic and Molecular Understanding of Skeletal Development*, Dev. Cell, vol.2, pp. 389-406 (2002).
Karsenty, "*Minireview: Transcriptional Control of Osteoblast Differentiation,*" *Endocrinology*, vol. 142, pp. 2731-2733 (2001).
Karsenty, "*The Complexities of Skeletal Biology,*" *Nature*, vol. 423, pp. 316-318 (2003).
Katagiri et al., "*Skeletal Abnormalities in Doubly Heterozygous Bmp4 and Bmp7 Mice,*" *Developmental Genetics*, vol. 22, pp. 340-348 (1998).
Kato et aL, "*Cbfa1-Independent Decrease in Osteoblast Proliferation, Osteopenia, and Persistent Embryonic Eye Vascularization in Mice Deficient in Lrp5, A Wnt Coreceptor,*" *The Journal of Cell Biology*, vol. 157, No. 2, pp. 303-314 (2002).
Keller et al., "Molecular Recognition of BMP-2 and BMP Receptor IA," *Nat. Struct. Mol. Biol*., 11(5):481-488 (2004).
Keri et al., "*Luteinizing Hormone Induction of Ovarian Tumors: Oligogenic Differences Between Mouse Strains Dictates Tumor Disposition,*" *PNAS*, vol. 7, No. 1, pp. 383-387 (2000).
Kerszberg et al., "*A Simple Molecular Model of Neurulation,*" *BioEssays*, vol. 20, pp. 758-770 (1998).
Kintner, "*Molecular Bases of Early Neural Development in Xenopus Embryos,*" *Ann. Rev. Neurosci*., vol. 15, pp. 251-284 (1992).
Kolm et al., "*Xenopus Hindbrain Patterning Requires Retinoid Signaling,*" *Developmental Biology*, vol. 192, pp. 1-16 (1997).
Krieg et al., "*In Vitro RNA Synthesis with SP6 RNA Polymerase,*" *Methods in Enzymology*, vol. 155, pp. 397-415 (1988).
Kronenberg et al., "*Developmental Regulation of the Growth Plate,*" *Nature*, vol. 423, pp. 332-338 (2003).
Kronenberg, "*Twist Genes Regulate Runx2 and Bone Formation,*" *Dev. Cell*, vol. 6, No. 3, pp. 17-18 (2004).
Krumlauf et al., U.S. Appl. No. 13/438,413, filed Apr. 3, 2012.
Krumlauf et al., U.S. Appl. No. 13/427,296, filed Mar. 22, 2012.
Kusu et al., "*Sclerostin is a Novel Secreted Osteoclast-Derived Bone Morphogenetic Protein (BMP) Antagonist with Unique Ligand Specificity,*" *The American Society for Biochemistry and Molecular Biology, Inc*., (Manuscript) M301716200 (Apr. 17, 2003).

(56) References Cited

OTHER PUBLICATIONS

Kusu et al., "Sclerostin Is a Novel Secreted Osteoclast-Derived Bone Morphogenetic Protein Antagonist With Unique Ligand Specificity," *J. Biol. Chem.*, vol. 278, pp. 24113-24117 (2003).
Kuure, "*Kidney Induction: Control by Notch, Wnt and GDNF/Ret Signaling,*" Helsinki University Biomedical Dissertations, No. 90 (2007).
Lamb et al., *Fibroblast Growth Factor Is a Direct Neural Inducer, Which Combined With Noggin Generates Anterior-Posterior Neural Pattern*, Development, vol. 121, pp. 3627-3636 (1995).
Latinkic et al., "*Xenopus Cyr61 Regulates Gastrulation Movements and Modulates Wnt Signalling,*" Development, vol. 130, pp. 2429-2441 (2003).
Laurikkala et al., "Identification of a Secreted BMP Antagonist, Ectodin, Integrating BMP, FGF, and SHH Signals From the Tooth Enamel Knot," *Developmental Biology*, vol. 264, No. 1, pp. 91-105 (2003).
Lederman et al., "*A Single Amino Acid Substitution in a Common African Allele of the CD4 Molecule Ablates Binding of the Monoclonal Antibody, OKT4,*" Mol. Immunology, vol. 28, pp. 1171-1181 (1991).
Lee et al., "*The Specification of Dorsal Cell Fates in the Vertebrate Central Nervous System,*" Annual Review of Neuroscience, vol. 22, No. 1, pp. 261-294 (1999).
Leyns et al., "*Frzb-1 is a Secreted Antagonist of Wnt Signaling Expresses in the Spemann Organizer,*" Cell, vol. 88, pp. 747-756 (1997).
Li et al., "Sclerostin Binds to LRP5/6 and Antagonizes Canonical Wnt Signalling," *Jour. Bio. Chem.*, 280(20); 19883-19887 (2005).
Li et al., "*Beta-Endorphin Omission Analogs: Dissociation of Immunoreactivity From Other Biological Activities,*" Proc. Natl. Acad. Sci., vol. 77, pp. 3211-3214 (1980).
Lian et al., "Bone Formation: Osteoblast Lineage Cells, Growth Factors, Matrix Proteins, and the Mineralization Process," *Primer on the Metabolic Bone Diseases and Disorders of Mineral Metabolism*, 4th Edition, 14-29 (1999).
Liem et al., "*A Role for the Roof Plate and Its Resident TGFβ-Related Proteins in Neuronal Patterning in the Dorsal Spinal Cord,*" Cell, vol. 91, pp. 127-138 (1997).
Liem et al., "*Dorsal Differentiation of Neural Plate Cells Induced by BMP-Mediated Signals from Epidermal Ectoderm,*" Cell, vol. 82, pp. 969-979 (1995).
Lin et al., "*Daily Cooperates With Drosophila Frizzled 2 to Transduce Wingless Signaling,*" Nature, vol. 400, pp. 281-284 (1999).
Lintern et al., "Characterization of Wise Protein and Its Molecular Mechanism to Interact with both Wnt and BMP Signals," *J. Bio. Chem.*, 284:23159-23168 (2009).
Little et al., "*A Mutation in the LDL Receptor-Related Protein 5 Gene Results in the Autosomal Dominant High-Bone-Mass Trait,*" The American Journal of Human Genetics, vol. 70, pp. 11-19 (2002).
Little et al., "*High Bone Density Due to a Mutation in LDL-Receptor-Related Protein 5,*" The New England Journal of Medicine, vol. 347, No. 12, pp. 943-944 (2002).
Lu et al., "*Isolation and Characterization of Checker β-Catenin,*" Gene, vol. 196, pp. 201-207 (1997).
Lumsden et al., "*Patterning the Vertebrate Neuraxis,*" Science, vol. 274, pp. 1109-1115 (1996).
Mao et al., "*LDL-Receptor-Related Protein 6 Is a Receptor for Dickkopf Proteins,*" Nature, vol. 411, pp. 321-325 (2001).
Marchler-Bauer et al., "*COD: A Curated Entrez Database of Conserved Domain Alignments,*" Nucleic Acids Research, vol. 31, No. 1, pp. 383-387 (2003).
Mathis et al., "*Pre-Steady-State Study of Recombinant Sesquiterpene Cyclases,*" Biochemistry, vol. 38, pp. 8340-8348 (1997).
McClary et al., "The Effects of Ascorbic Acid on the Osteoblast Extracellular Matrix," http://lsvl.la.asu.edu/ubep2001/abstracts/mcclary1, visited on Jun. 11, 2003.

McGrew et al., "*Direct Regulation of the Xenopus Engrailed-2 Promoter by the Wnt Signaling Pathway, and a Molecular Screen for Wnt-Responsive Genes, Confirm a Role for Wnt Signaling During Neural Patterning in Xenopus,*" Mechanisms of Development, vol. 87, pp. 21-32 (1999).
McGrew et al., "*Specification of the Anteroposterior Neural Axis through Synergistic Interaction of the Wnt Signaling Cascade with noggin and follistatin,*" Developmental Biology, vol. 172, pp. 337-342 (1995).
McGrew et al., "*Wnt and FGF Pathways Cooperatively Pattern Anteroposterior Neural Ectoderm in Xenopus,*" Mechanisms of Development, vol. 69, pp. 105-114 (1997).
McMahon et al., "*Noggin-Mediated Antagonism of BMP Signaling Is Required for Growth and Patterning of the Neural Tube and Somite,*" Genes & Development, vol. 12, pp. 1438-1452 (1998).
McMahon et al., "*The Midbrain-Hindbrain Phenotype of Wnt-1-/Wnt-1- Mice Results from Stepwise Deletion of engrailed-Expressing Cells by 9.5 Days Postcoitum,*" Cell, vol. 69, pp. 581-595 (1992).
Meitinger et al., "*Molecular Modelling of the Norrie Disease Protein Predicts a Cystine Knot Growth Factor Tertiary Structure,*" Nature Genetics, vol. 5, pp. 376-380 (1993).
Mercurio et al., "*Connective-Tissue Growth Factor (CTGF) Modulates Wnt Signalling and Interacts With the Wnt Receptor Complex,*" Development, vol. 131, pp. 2137-2147.
Mizuno et al., "*Hepatocyte growth factor prevents renal fibrosis and dysfunction in a mouse model of chronic renal disease,*" J. Clinical Investigation, vol. 101, pp. 1827-1834 (1998).
Moon, R.T., et al., Overview of the role of beta-catenin in specification of the dorsal-ventral axis of Xenopus, http://www.ucalgary.ca/UofC/eduweb/virtualembryo/beta_catenin.html (1998).
Moon et al., "*Structurally Related Receptors and Antagonists Compete for Secreted Wnt Ligands,*" Cell, vol. 88, pp. 725-728 (1997).
Muhr et al., "*Assignment of Early Caudal Identity to Neural Plate Cells by a Signal from Caudal Paraxial Mesoderm,*" Neuron, vol. 19, pp. 487-502 (1997).
Muhr et al., "*Convergent Inductive Signals Specify Midbrain, Hindbrain, and Spinal Cord Identity in Gastrula Stage Chick Embryos,*" Neuron, vol. 23, pp. 689-702 (1999).
Mullins et al., "Transgenesis in the Rat and Larger Mammals," *J. Clin. Invest.*, 97(7):1557-1560 (1996).
Munsterberg et al., "*Combinatorial Signaling by Sonic Hedgehog and Wnt Family Members Induces Myogenic bHLH Gene Expression in the Somite,*" Genes & Development, vol. 9, pp. 2911-2922 (1995).
Niemann, "*Transgenic Farm Animals Get Off the Ground. Transgenic Animals in Agriculture,*" Transg. Res., vol. 7, pp. 73-75 (1998).
Nieuwkoop et al., "*Activation and Organization of the Central Nervous System in Amphibians,*" The Journal of Experimental Zoology, vol. 120, No. 1, pp. 1-108 (1952).
Nijweide et al., "*Identification of Osteocytes in Osteoblast-Like Cell Cultures Using a Monoclonal Antibody Specifically Directed Against Osteocytes,*" Histochemistry, vol. 84, pp. 342-347 (1986).
Non-Final Office Action dated Oct. 15, 2009 in U.S. Appl. No. 11/985,836 (Paper No. 20090930).
Non-Final Office Action dated Sep. 17, 2009 in U.S. Appl. No. 11/508,701 (Paper No. 20090903).
Oshima et al., "*TGF-β Receptor Type II Deficiency Results in Defects of Yolk Sac Hematopoiesis and Vasculogenesis,*" Developmental Biology, 179:297-302 (1996).
Patel et al., "*Regulation of Bone Formation and Vision by LRP5,*" The New England Journal of Medicine, vol. 346, No. 20, pp. 1572-1574 (2002).
Patel, Z., et al., The Role of Retinoic Acid in Patterning of the CNS in Xenopus, http://www.ucalnary.ca/UofC/eduwebg/virtualembryo/retinoic_CNS.html (1998).
Pera et al., "*A Direct Screen for Secreted Proteins in Xenopus Embryos Identifies Distinct Activities for the Wnt Antagonists Crescent and Frzb-1,*" Mechanisms of Development, vol. 98, pp. 183-195 (2000).

(56) References Cited

OTHER PUBLICATIONS

Piccolo et al., "*Dorsoventral Patterning in Xenopus: Inhibition of Ventral Signals by Direct Binding of Chordin to BMP-4,*" Cell, vol. 86, pp. 589-598 (1996).
Piccolo et al., "*The Head Inducer Cerberus Is a Multifunctional Antagonist of Nodal, BMP and Wnt Signals,*" Nature, vol. 397, pp. 707-710 (1999).
Pinson et al., "*An LDL-Receptor-Related Protein Mediates Wnt Signalling in Mice,*" Nature, vol. 407, pp. 535-538 (2000).
Pittenger et al., "Multilineage Potential of Adult Human Mesenchymal Stem Cells," Science, 284:143-147.
Pockwinse et aL, "Expression of Cell Growth and Bone Specific Genes at Single Cell Resolution During Development of Bone Tissue-Like Organization in Primary Osteoblast Cultures," Journal of Cellular Biochemistry, 49:310-323 (1992).
Pownall et al., "*eFGF, Xcad3 and Hox Genes Form a Molecular Pathway That Establishes the Anteroposterlor Axis in Xenopus,*" Development, vol. 122, pp. 3881-3892 (1998).
Pownall et al., "*Two Phases of Hox Gene Regulation During Early Xenopus Development,*" Current Biology, vol. 8, No. 11, pp. 673-676 (1998).
Prince et al., "*Hox Gene Expression Reveals Regionalization Along the Anteroposterior Axis of the Zebrafish Notochord,*" Dev. Genes Evol., vol. 208, pp. 517-522 (1998).
Rasmussen et al., "*Regulation of Eye Development by Frizzled Signaling in Xenopus,*" Proc. Natl. Acad. Sci. USA, vol. 98, No. 7, pp. 3881-3866 (2001).
Reddi, A.H., Interplay between bone morphogenetic proteins and cognate binding proteins in bone and cartilage development: noggin, chordin and DAN, commentary available online http://arthritis-research.com/content/3/001. Arthritis Res., vol. 3, No. 1, 5 pages (2000).
Response to Final Office Action dated Apr. 27, 2010 in U.S. Appl. No. 11/508,701.
Response to Final Office Action dated May 13, 2010 in U.S. Appl. No. 11/985,836.
Response to Non-Final Office Action dated Oct. 15, 2009 in U.S. Appl. No. 11/985,836.
Response to Non-Final Office Action dated Sep. 17, 2009 in U.S. Appl. No. 11/508,701.
Rosen et al., "*Defining the Genetics of Osteoporosis: Using the Mouse to Understand Man,*" Osteoporosis International, vol. 12, pp. 803-810 (2001).
Rothberg et al., *Slit: An Extracellular Protein Necessary for Development of Midline Glia and Commissural Axon Pathways Contains Both EGF and LRR Domains*, Genes & Development, vol. 4, pp. 2169-2187 (1990).
Ruiz I Altaba, "*Pattern Formation in the Vertebrate Neural Plate,*" TINS, vol. 17, No. 6, pp. 233-243 (1994).
Salic et al., "*Sizzled: A Secreted Xwnt8 Antagonist Expressed in the Ventral Marginal Zone of Xenopus Embryos,*" Development, vol. 124, pp. 4739-4748 (1997).
Sasai et al., "*Xenopus Chordin: A Novel Dorsalizing Factor Activated by Organizer-Specific Homeobox Genes,*" Cell, vol. 79, pp. 779-790 (1994).
Schmitt et al., "Bone Morphogenetic Proteins: An Update on Basic Biology and Clinical Relevance," Journal of Orthopaedic Research,17:269-278 (1999).
Schweizer, et al., Wnt/Wingless signaling through β-catenin requires the function of both LRP/Arrow and frizzied, classes of receptors, BMC Cell Biology research article available at http://www.biomedcentral.com/1471-2121/4/4. BMC Cell Biology, vol. 4, 11 pages (2003).
Segarini et al., "*The Low Density Lipoprotein Receptor-Related Protein/alpha2-Macroglobulin Receptor is a Receptor for Connective Tissue Growth Factor (CTGF),*" The American Society for Biochemistry and Molecular Biology, Inc., (Manuscript) M105180200 (2001).

Semenov et al., "*SOST Is a Ligand for LRP5/LRP6 and a Wnt Signaling Inhibitor,*" J. Biol. Chem., vol. 280, No. 29, pp. 26770-26775 (2005).
Sevetson et al., "*Cbfa1/RUNX2 Directs Specific Expression of the Sclerosteosis Gene (SOST),*" J. Biol. Chem., (Manuscript) (Jan. 22, 2004).
Simmons et al., "*Uterine Sensitization-Associated Gene-1: A Novel Gene Induced Within the Rat Endometrium at the Time of Uterine Receptivity/Sensitization for the Decidual Cell Reaction,*" Biology of Reproduction, vol. 67, pp. 1638-1645 (2002).
Smith, "TGF β inhibitors, new and unexpected requirements in vertebrate development," TIG, 15(1):3-5 (1999).
Solloway et al., "*Mice Lacking Bmp8 Function,*" Developmental Genetics, pp. 22:321-339 (1998).
Stanley et al., "*DAN Is a Secreted Glycoprotein Related to Xenopus Cerberus,*" Mech. Dev., vol. 77, pp. 173-184 (1998).
Stebbins et al., "*Structure of the VHL-ElonginC-ElonginB Comples: Implications for VHL Tumor Suppressor Function,*" Science, vol. 284, pp. 455-461 (1999).
Stephen et al., "*Dental and Oral Manifestations of Sclerosteosis,*" International Dental Journal, vol. 51, pp. 287-290 (2001).
Streit et al., "*Neural Induction a Bird's Eye View,*" Trends in Genetics, vol. 15, No. 1, pp. 20-24 (1999).
Tada et al., "*Xwnt 11 Is a Target of Xenopus Brachyury: Regulation of Gastrulation Movements via Dishevelled, But Not Through the Canonical Wnt Pathway,*" Development, vol. 127, pp. 2227-2238 (2000).
Tamai et al., "*LDL-Receptor-Related Proteins in Wnt Signal Transduction,*" Nature, vol. 407, pp. 530-535.
Tanaka et al., "*Expression of BMP-7 and USAG-1 (A BMP Antagonist) In Kidney Development and Injury*", Kidney International, vol. 73, pp. 181-191 (2008).
Thisse et al., "*Activin- and Nodal-Related Factors Control Antero-Posterior Patterning of the Zebrafish Embryo,*" Nature, vol. 403, pp. 425-428 (2000).
Torres et al., "The Cologne Guide to Gene Targeting," (Manuscript) (1995).
Trainor et al., "*Plasticity in Mouse Neural Crest Cells Reveals a New Patterning Role for Cranial Mesoderm,*" Nature Cell Biology, vol. 2, pp. 96-102 (2000).
Tsuda et al., "*The Cell-Surface Proteoglycan Daily Regulates Wingless Signalling in Drosophila,*" Nature, vol. 400, pp. 276-280 (1999).
Van Bezooijen et al., "Wnt but Not BMP Signaling Is Involved in the Inhibitory Action of Sclerostin on BMP-Stimulated Bone Formation," J. Bone. Miner. Res., 22:19-28 (2007).
Vleminckx et al., The C-Terminal Transactivation Domain of β-Catenin Is Necessary and Sufficient for Signalling by the LEF-1/β-Catenin Complex in Xenopus Laevis, Mechanisms of Development, vol. 81, pp. 65-74 (1999).
Von Heune, "*A New Method for Predicting Signal Sequence Cleavage Sites,*" Nucleic Acid Research, vol. 14, pp. 4683-4690 (1986).
Wall, "*Transgenic Livestock: Progress and Prospects for the Future,*" Theriogenology, vol. 45, pp. 57-68 (1996).
Wallingford et al., "*Disheveled Controls Cell Polarity During Xenopus Gastrulation,*" Nature, vol. 405, pp. 81-85 (2000).
Wang et al., "*Frzb, a Secreted Protein Expressed in the Spemann Organizer, Binds and inhibits Wnt-8,*" Cell, vol. 88, pp. 757-766 (1997).
Wehrli et al., "*Arrow Encodes an LDL-Receptor-Related Protein Essential for Wingless Signalling,*" Nature, vol. 407, pp. 527-530 (2000).
Winkler et al., "*Osteocyte Control of Bone Formation Via Sclerostin, A Novel BMP Antagonist,*" The European Molecular Biology Organization Journal, vol. 22, No. 23, pp. 6267-6276 (2003).
Wood et al., "*Jaw Involvement in Sclerosteosis: A Case Report,*" Dentomaxillofac. Radiol., vol. 17, pp. 145-148 (1988).
Wu et al., "*Mutual Antagonism Between Dickkopf1 and Dickkopf2 Regulates Wnt/Beta-Catenin Signaling,*" Curr. Biol., vol. 10, No. 24, pp. 1611-1614 (2000).

(56) References Cited

OTHER PUBLICATIONS

Yanagita et al., "*Uterine Sensitization-Associated Gene-1 (USAG-1), A Novel BMP Antagonist Expressed in the Kidney, Accelerates Tubular Injury,*" *J. Clinical Investigation*, vol. 116, pp. 70-79 (2006).

Yang et al., "CBFAI, OSF-1 *Expression and Ex Vivo Mineralisation by Human Osteoprogenitors on 3-Dimensional Porous Biodegradable Structures,*" *Poster Session, 47th Annual Meeting, Orthopaedic Research Society*, Feb. 25-28, 2001, San Francisco, CA.

Yokouchi et al., "*Antagonistic Signaling by Caronte, A Novel Cerberus-Related Gene, Establishes Left-Right Asymmetric Gene Expression,*" *Cell*, vol. 98, pp. 573-583 (1999).

Zelzer et al., "*The Genetic Basis for Skeletal Diseases,*" *Nature*, vol. 423, pp. 343-348 (2003).

Non-Final Office Action dated Nov. 20, 2012 in U.S. Appl. No. 13/438,413 (Paper No. 20121118).

U.S. Appl. No. 13/863,939, filed Apr. 16, 2013.

Non-Final Office Action dated Dec. 13, 2012 in U.S. Appl. No. 13/030,863 (Paper No. 20121211B).

Response to Non-Final Office Action dated Dec. 13, 2012 in U.S. Appl. No. 13/030,863 dated Apr. 15, 2013.

Non-Final Office Action dated Jun. 16, 2008 in U.S. Appl. No. 11/613,658 (Paper No. 20080609).

Response to Non-Final Office Action dated Jun. 16, 2008 in U.S. Appl. No. 11/613,658 dated Dec. 16, 2008.

Non-Final Office Action dated Jan. 31, 2006 in U.S. Appl. No. 10/464,368 (Paper No. 01182005).

Response to Non-Final Office Action dated Jan. 31, 2006 in U.S. Appl. No. 10/464,368 dated Jul. 31, 2006.

Final Office Action dated Oct. 18, 2006 in U.S. Appl. No. 10/464,368 (Paper No. 10112006).

Response to Final Office Action dated Oct. 18, 2006 in U.S. Appl. No. 10/464,368 dated Mar. 14, 2007.

Non-Final Office Action dated May 18, 2007 in U.S. Appl. No. 10/464,368 (Paper No. 05102007).

\* cited by examiner

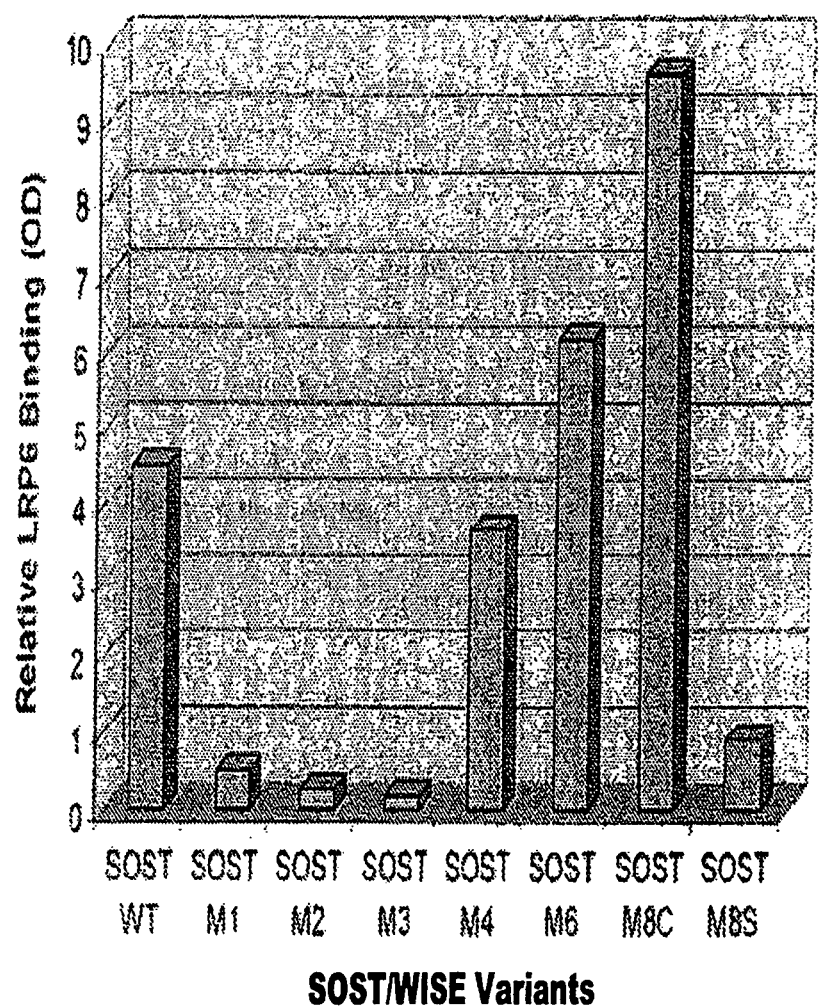

under renal failure, which is often life threatening. Renal damage and failure can only be managed through dialysis or organ transplantation.

SEQUENCE LISTING

```
<160> NUMBER OF SEQ ID NOS: 217

<210> SEQ ID NO 1
<211> LENGTH: 4131
<212> TYPE: DNA
<213> ORGANISM: Human

<400> SEQUENCE: 1
atgggggccg tcctgaggag cctcctggcc tgcagcttct gtgtgctcct gagagcggcc        60
cctttgttgc tttatgcaaa cagacgggac ttgcgattgg ttgatgctac aaatggcaaa       120
gagaatgcta cgattgtagt tggaggcttg gaggatgcag ctgcggtgga ctttgtgttt       180
agtcatggct tgatatactg gagtgatgtc agcgaagaag ccattaaacg aacagaattt       240
aacaaaactg agagtgtgca gaatgttgtt gtttctggat tattgtcccc cgatgggctg       300
gcatgtgatt ggcttggaga aaaattgtac tggacagatt ctgaaactaa tcggattgaa       360
gtttctaatt tagatggatc tttacgaaaa gttttatttt ggcaagagtt ggatcaaccc       420
agagctattg ccttagatcc ttcaagtggg ttcatgtact ggacagactg gggagaagtg       480
ccaaagatag aacgtgctgg aatggatggt tcaagtcgct tcattataat aaacagtgaa       540
atttactggc caaatggact gactttggat tatgaagaac aaaagcttta ttgggcagat       600
gcaaaactta atttcatcca caaatcaaat ctggatggaa caaatcggca ggcagtggtt       660
aaaggttccc ttccacatcc ttttgccttg acgttatttg aggacatatt gtactggact       720
gactggagca cacactccat tttggcttgc aacaagtata ctggtgaggg tctgcgtgaa       780
atccattctg acatcttctc tcccatggat atacatgcct tcagccaaca gaggcagcca       840
aatgccacaa atccatgtgg aattgacaat gggggttgtt cccatttgtg tttgatgtct       900
ccagtcaagc ctttttatca gtgtgcttgc cccactgggg tcaaactcct ggagaatgga       960
aaaacctgca aagatggtgc cacagaatta ttgcttttag ctcgaaggac agacttgaga      1020
cgcatttctt tggatacacc agattttaca gacattgttc tgcagttaga agacatccgt      1080
catgccattg ccatagatta cgatcctgtg gaaggctaca tctactggac tgatgatgaa      1140
gtgagggcca tacgccgttc atttatagat ggatctggca gtcagtttgt ggtcactgct      1200
caaattgccc atcctgatgg tattgctgtg gactgggttg cacgaaatct ttattggaca      1260
gacactggca ctgatcgaat agaagtgaca aggctcaatg ggaccatgag gaagatcttg      1320
atttcagagg acttagagga accccgggct attgtgttag atcccatggt tgggtacatg      1380
tattggactg actggggaga aattccgaaa attgagcgag cagctctgga tggttctgac      1440
cgtgtagtat tggttaacac ttctcttggt tggccaaatg gtttagcctt ggattatgat      1500
gaaggcaaaa tatactgggg agatgccaaa acagacaaga ttgaggttat gaatactgat      1560
ggcactggga gacgagtact agtggaagac aaaattcctc acatatttgg atttactttg      1620
```

```
ttgggtgact atgtttactg gactgactgg cagaggcgta gcattgaaag agttcataaa    1680
cgaagtgcag agagggaagt gatcatagat cagctgcctg acctcatggg cctaaaggct    1740
acaaatgttc atcgagtgat tggttccaac ccctgtgctg aggaaaacgg gggatgtagc    1800
catctctgcc tctatagacc tcagggcctt cgctgtgctt gccctattgg ctttgaactc    1860
atcagtgaca tgaagacctg cattgtccca gaggctttcc ttttgttttc acggagagca    1920
gatatcagac gaatttctct ggaaacaaac aataataatg tggctattcc actcactggt    1980
gtcaaagaag cttctgcttt ggattttgat gtgacagaca accgaattta ttggactgat    2040
atatcactca agaccatcag cagagccttt atgaatggca gtgcactgga acatgtggta    2100
gaattcggct tagattatcc agaaggcatg gcagtagact ggcttgggaa gaacttgtac    2160
tgggcagaca caggaacgaa tcgaattgag gtgtcaaagt tggatgggca gcaccgacaa    2220
gttttggtgt ggaaagacct agatagtccc agagctctcg cgttggaccc tgccgaagga    2280
tttatgtatt ggactgaatg gggtggaaaa cctaagatag acagagctgc aatggatgga    2340
agtgaacgta ctaccttagt tccaaatgtg gggcgggcaa acggcctaac tattgattat    2400
gctaaaagga ggctttattg gacagacctg gacaccaact taatagaatc ttcaaatatg    2460
cttgggctca accgtgaagt tatagcagat gacttgcctc atcctttgg cttaactcag    2520 taccaagatt atatctactg gacggactgg agccgacgca gcattgagcg tgccaacaaa    2580
accagtggcc aaaaccgcac catcattcag ggccatttgg attatgtgat ggacatcctc    2640
gtctttcact catctcgaca gtcagggtgg aatgaatgtg cttccagcaa tgggcactgc    2700
tcccacctct gcttggctgt gccagttggg ggttttgttt gtggatgccc tgcccactac    2760
tctcttaatg ctgacaacag gacttgtagt gctcctacga cttttcctgct cttcagtcaa    2820 aagagtgcca tcaaccgcat ggtgattgat gaacaacaga gccccgacat catccttccc    2880
atccacagcc ttcggaatgt ccgggccatt gactatgacc cactggacaa gcaactctat    2940
tggattgact cacgacaaaa catgatccga aaggcacaag aagatggcag ccagggcttt    3000
actgtggttg tgagctcagt tccgagtcag aacctggaaa tacaacccta tgacctcagc    3060
attgatattt acagccgcta catctactgg acttgtgagg ctaccaatgt cattaatgtg    3120
acaagattag atgggagatc agttggagtg gtgctgaaag gcgagcagga cagacctcga    3180
gccattgtgg taaacccaga gaagggtat atgtattta ccaatcttca ggaaaggtct    3240
cctaaaattg aacgggctgc tttggatggg acagaacggg aggtcctctt tttcagtggc    3300
ttaagtaaac caattgcttt agcccttgat agcaggctgg gcaagctctt tgggctgat    3360 tcagatctcc ggcgaattga aagcagtgat ctctcaggtg ctaaccggat agtattagaa    3420
gactccaata tcttgcagcc tgtgggactt actgtgtttg aaaactggct ctattggat    3480 gataaacagc agcaaatgat tgaaaaaatt gacatgacag gtcgagaggg tagaaccaaa    3540
gtccaagctc gaattgccca gcttagtgac attcatgcag taaaggagct gaaccttcaa    3600
gaatacagac agcaccctg tgctcaggat aatggtggct gttcacatat ttgtcttgta    3660 aaggggatg gtactacaag gtgttcttgc cccatgcacc tggttctact tcaagatgag    3720
ctatcatgtg gagaacctcc aacatgttct cctcagcagt ttacttgttt cacggggaa    3780 attgactgta tcctgtggc ttggcggtgc gatgggttta ctgaatgtga agaccacagt    3840
gatgaactca attgtcctgt atgctcagag tcccagttcc agtgtgccag tgggcagtgt    3900
attgatggtg ccctccgatg caatggagat gcaaactgcc aggacaaatc agatgagaag    3960
aactgtgaag tgctttgttt aattgatcag ttccgctgtg ccaatggtca gtgcattgga    4020
```

```
                                  -continued aagcacaaga agtgtgatca taatgtggat tgcagtgaca agtcagatga actggattgt    4080
tatccgactg aagaaccagc accacaggcc accaatacag ttggttctgt t             4131

<210> SEQ ID NO 2
<211> LENGTH: 1377
<212> TYPE: PRT
<213> ORGANISM: Human

<400> SEQUENCE: 2

Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
                20                  25                  30

Leu Val Asp Ala Thr Asn Gly Lys Glu Asn Ala Thr Ile Val Val Gly
            35                  40                  45

Gly Leu Glu Asp Ala Ala Ala Val Asp Phe Val Phe Ser His Gly Leu
        50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Ser Gly Leu Leu Ser
                85                  90                  95

Pro Asp Gly Leu Ala Cys Asp Trp Leu Gly Glu Lys Leu Tyr Trp Thr
            100                 105                 110

Asp Ser Glu Thr Asn Arg Ile Glu Val Ser Asn Leu Asp Gly Ser Leu
        115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175

Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
    210                 215                 220

Pro His Pro Phe Ala Leu Thr Leu Phe Glu Asp Ile Leu Tyr Trp Thr
225                 230                 235                 240

Asp Trp Ser Thr His Ser Ile Leu Ala Cys Asn Lys Tyr Thr Gly Glu
                245                 250                 255

Gly Leu Arg Glu Ile His Ser Asp Ile Phe Ser Pro Met Asp Ile His
            260                 265                 270

Ala Phe Ser Gln Gln Arg Gln Pro Asn Ala Thr Asn Pro Cys Gly Ile
        275                 280                 285

Asp Asn Gly Gly Cys Ser His Leu Cys Leu Met Ser Pro Val Lys Pro
    290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Leu Ala Arg Arg
                325                 330                 335

Thr Asp Leu Arg Arg Ile Ser Leu Asp Thr Pro Asp Phe Thr Asp Ile
            340                 345                 350
```

```
Val Leu Gln Leu Glu Asp Ile Arg His Ala Ile Ala Ile Asp Tyr Asp
            355                 360                 365

Pro Val Glu Gly Tyr Ile Tyr Trp Thr Asp Asp Glu Val Arg Ala Ile
370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
            420                 425                 430

Asn Gly Thr Met Arg Lys Ile Leu Ile Ser Glu Asp Leu Glu Glu Pro
            435                 440                 445

Arg Ala Ile Val Leu Asp Pro Met Val Gly Tyr Met Tyr Trp Thr Asp
            450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Lys Ile Tyr Trp Gly Asp Ala Lys Thr Asp
            500                 505                 510

Lys Ile Glu Val Met Asn Thr Asp Gly Thr Gly Arg Arg Val Leu Val
            515                 520                 525

Glu Asp Lys Ile Pro His Ile Phe Gly Phe Thr Leu Leu Gly Asp Tyr
            530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Asn Val His Arg Val Ile Gly Ser Asn Pro Cys
            580                 585                 590

Ala Glu Glu Asn Gly Gly Cys Ser His Leu Cys Leu Tyr Arg Pro Gln
            595                 600                 605

Gly Leu Arg Cys Ala Cys Pro Ile Gly Phe Glu Leu Ile Ser Asp Met
610                 615                 620

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Val Ala Ile
                645                 650                 655

Pro Leu Thr Gly Val Lys Glu Ala Ser Ala Leu Asp Phe Asp Val Thr
            660                 665                 670

Asp Asn Arg Ile Tyr Trp Thr Asp Ile Ser Leu Lys Thr Ile Ser Arg
                675                 680                 685

Ala Phe Met Asn Gly Ser Ala Leu Glu His Val Val Glu Phe Gly Leu
690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
            740                 745                 750

Leu Ala Leu Asp Pro Ala Glu Gly Phe Met Tyr Trp Thr Glu Trp Gly
            755                 760                 765

Gly Lys Pro Lys Ile Asp Arg Ala Ala Met Asp Gly Ser Glu Arg Thr
```

```
                770             775             780
Thr Leu Val Pro Asn Val Gly Arg Ala Asn Gly Leu Thr Ile Asp Tyr
785             790             795             800

Ala Lys Arg Arg Leu Tyr Trp Thr Asp Leu Asp Thr Asn Leu Ile Glu
            805             810             815

Ser Ser Asn Met Leu Gly Leu Asn Arg Glu Val Ile Ala Asp Asp Leu
            820             825             830

Pro His Pro Phe Gly Leu Thr Gln Tyr Gln Asp Tyr Ile Tyr Trp Thr
            835             840             845

Asp Trp Ser Arg Arg Ser Ile Glu Arg Ala Asn Lys Thr Ser Gly Gln
            850             855             860

Asn Arg Thr Ile Ile Gln Gly His Leu Asp Tyr Val Met Asp Ile Leu
865             870             875             880

Val Phe His Ser Ser Arg Gln Ser Gly Trp Asn Glu Cys Ala Ser Ser
            885             890             895

Asn Gly His Cys Ser His Leu Cys Leu Ala Val Pro Val Gly Gly Phe
            900             905             910

Val Cys Gly Cys Pro Ala His Tyr Ser Leu Asn Ala Asp Asn Arg Thr
            915             920             925

Cys Ser Ala Pro Thr Thr Phe Leu Leu Phe Ser Gln Lys Ser Ala Ile
            930             935             940

Asn Arg Met Val Ile Asp Glu Gln Gln Ser Pro Asp Ile Ile Leu Pro
945             950             955             960

Ile His Ser Leu Arg Asn Val Arg Ala Ile Asp Tyr Asp Pro Leu Asp
            965             970             975

Lys Gln Leu Tyr Trp Ile Asp Ser Arg Gln Asn Met Ile Arg Lys Ala
            980             985             990

Gln Glu Asp Gly Ser Gln Gly Phe Thr Val Val Val Ser Ser Val Pro
            995             1000            1005

Ser Gln Asn Leu Glu Ile Gln Pro Tyr Asp Leu Ser Ile Asp Ile
            1010            1015            1020

Tyr Ser Arg Tyr Ile Tyr Trp Thr Cys Glu Ala Thr Asn Val Ile
            1025            1030            1035

Asn Val Thr Arg Leu Asp Gly Arg Ser Val Gly Val Val Leu Lys
            1040            1045            1050

Gly Glu Gln Asp Arg Pro Arg Ala Ile Val Val Asn Pro Glu Lys
            1055            1060            1065

Gly Tyr Met Tyr Phe Thr Asn Leu Gln Glu Arg Ser Pro Lys Ile
            1070            1075            1080

Glu Arg Ala Ala Leu Asp Gly Thr Glu Arg Glu Val Leu Phe Phe
            1085            1090            1095

Ser Gly Leu Ser Lys Pro Ile Ala Leu Ala Leu Asp Ser Arg Leu
            1100            1105            1110

Gly Lys Leu Phe Trp Ala Asp Ser Asp Leu Arg Arg Ile Glu Ser
            1115            1120            1125

Ser Asp Leu Ser Gly Ala Asn Arg Ile Val Leu Glu Asp Ser Asn
            1130            1135            1140

Ile Leu Gln Pro Val Gly Leu Thr Val Phe Glu Asn Trp Leu Tyr
            1145            1150            1155

Trp Ile Asp Lys Gln Gln Gln Met Ile Glu Lys Ile Asp Met Thr
            1160            1165            1170

Gly Arg Glu Gly Arg Thr Lys Val Gln Ala Arg Ile Ala Gln Leu
            1175            1180            1185
```

| Ser | Asp | Ile | His | Ala | Val | Lys | Glu | Leu | Asn | Leu | Gln | Glu | Tyr | Arg |
|---|---|---|---|---|---|---|---|---|---|---|---|---|---|---|
| 1190 | | | | | 1195 | | | | 1200 | | | | | |

Gln His Pro Cys Ala Gln Asp Asn Gly Gly Cys Ser His Ile Cys
     1205            1210                1215

Leu Val Lys Gly Asp Gly Thr Thr Arg Cys Ser Cys Pro Met His
     1220            1225                1230

Leu Val Leu Leu Gln Asp Glu Leu Ser Cys Gly Glu Pro Pro Thr
     1235            1240                1245

Cys Ser Pro Gln Gln Phe Thr Cys Phe Thr Gly Glu Ile Asp Cys
     1250            1255                1260

Ile Pro Val Ala Trp Arg Cys Asp Gly Phe Thr Glu Cys Glu Asp
     1265            1270                1275

His Ser Asp Glu Leu Asn Cys Pro Val Cys Ser Glu Ser Gln Phe
     1280            1285                1290

Gln Cys Ala Ser Gly Gln Cys Ile Asp Gly Ala Leu Arg Cys Asn
     1295            1300                1305

Gly Asp Ala Asn Cys Gln Asp Lys Ser Asp Glu Lys Asn Cys Glu
     1310            1315                1320

Val Leu Cys Leu Ile Asp Gln Phe Arg Cys Ala Asn Gly Gln Cys
     1325            1330                1335

Ile Gly Lys His Lys Lys Cys Asp His Asn Val Asp Cys Ser Asp
     1340            1345                1350

Lys Ser Asp Glu Leu Asp Cys Tyr Pro Thr Glu Glu Pro Ala Pro
     1355            1360                1365

Gln Ala Thr Asn Thr Val Gly Ser Val
     1370            1375

<210> SEQ ID NO 3
<211> LENGTH: 4842
<212> TYPE: DNA
<213> ORGANISM: Human

<400> SEQUENCE: 3

```
atggggggccg tcctgaggag cctcctggcc tgcagcttct gtgtgctcct gagagcggcc    60
cctttgttgc tttatgcaaa cagacgggac ttgcgattgg ttgatgctac aaatggcaaa   120
gagaatgcta cgattgtagt tggaggcttg gaggatgcag ctgcggtgga ctttgtgttt   180
agtcatggct tgatatactg gagtgatgtc agcgaagaag ccattaaacg aacagaattt   240
aacaaaactg agagtgtgca gaatgttgtt gtttctggat tattgtcccc cgatgggctg   300
gcatgtgatt ggcttggaga aaaattgtac tggacagatt ctgaaactaa tcggattgaa   360
gtttctaatt tagatggatc tttacgaaaa gttttatttt ggcaagagtt ggatcaaccc   420
agagctattg ccttagatcc ttcaagtggg ttcatgtact ggacagactg gggagaagtg   480
ccaaagatag aacgtgctgg aatggatggt tcaagtcgct tcattataat aaacagtgaa   540
atttactggc caaatggact gactttggat tatgaagaac aaaagcttta ttgggcagat   600
gcaaaactta atttcatcca caatcaaat ctggatggaa caaatcggca ggcagtggtt   660
aaaggttccc ttccacatcc ttttgccttg acgttatttg aggacatatt gtactggact   720
gactggagca cacactccat tttggcttgc aacaagtata ctggtgaggg tctgcgtgaa   780
atccattctg acatcttctc tcccatggat atacatgcct tcagccaaca gaggcagcca   840
aatgccacaa atccatgtgg aattgacaat ggggggttgtt cccatttgtg tttgatgtct   900
ccagtcaagc cttttttatca gtgtgcttgc cccactgggg tcaaactcct ggagaatgga   960
```

```
aaaacctgca aagatggtgc cacagaatta ttgcttttag ctcgaaggac agacttgaga    1020
cgcatttctt tggatacacc agattttaca gacattgttc tgcagttaga agacatccgt    1080
catgccattg ccatagatta cgatcctgtg aaggctaca tctactggac tgatgatgaa     1140
gtgagggcca tacgccgttc atttatagat ggatctggca gtcagtttgt ggtcactgct    1200
caaattgccc atcctgatgg tattgctgtg gactggttg cacgaaatct ttattggaca     1260
gacactggca ctgatcgaat agaagtgaca aggctcaatg ggaccatgag gaagatcttg    1320
atttcagagg acttagagga accccgggct attgtgttag atcccatggt tgggtacatg    1380
tattggactg actggggaga aattccgaaa attgagcgag cagctctgga tggttctgac    1440
cgtgtagtat tggttaacac ttctcttggt tggccaaatg gtttagcctt ggattatgat    1500
gaaggcaaaa tatactgggg agatgccaaa acagacaaga ttgaggttat gaatactgat    1560
ggcactggga gacgagtact agtggaagac aaaattcctc acatatttgg atttactttg    1620
ttgggtgact atgtttactg gactgactgg cagaggcgta gcattgaaag agttcataaa    1680
cgaagtgcag agagggaagt gatcatagat cagctgcctg acctcatggg cctaaaggct    1740
acaaatgttc atcgagtgat tggttccaac ccctgtgctg aggaaaacgg gggatgtagc    1800
catctctgcc tctatagacc tcagggcctt cgctgtgctt gccctattgg ctttgaactc    1860
atcagtgaca tgaagacctg cattgtccca gaggctttcc ttttgttttc acggagagca    1920
gatatcagac gaatttctct ggaaacaaac aataataatg tggctattcc actcactggt    1980
gtcaaagaag cttctgcttt ggatttgat gtgacagaca accgaattta ttggactgat    2040
atatcactca agaccatcag cagagccttt atgaatggca gtgcactgga acatgtggta    2100
gaattcggct tagattatcc agaaggcatg cagtagact ggcttgggaa gaacttgtac     2160
tgggcagaca caggaacgaa tcgaattgag gtgtcaaagt tggatgggca gcaccgacaa    2220
gttttggtgt ggaaagacct agatagtccc agagctctcg cgttggaccc tgccgaagga    2280
tttatgtatt ggactgaatg gggtggaaaa cctaagatag acagagctgc aatggatgga    2340
agtgaacgta ctaccttagt tccaaatgtg gggcgggcaa acggcctaac tattgattat    2400
gctaaaagga ggctttattg gacagacctg gacaccaact aatagaatc ttcaaatatg      2460 cttgggctca accgtgaagt tatagcagat gacttgcctc atccttttgg cttaactcag    2520
taccaagatt atatctactg gacggactgg agccgacgca gcattgagcg tgccaacaaa    2580
accagtggcc aaaaccgcac catcattcag ggccatttgg attatgtgat ggacatcctc    2640
gtctttcact catctcgaca gtcagggtgg aatgaatgtg cttccagcaa tgggcactgc    2700
tcccacctct gcttggctgt gccagttggg ggttttgttt gtggatgccc tgcccactac    2760
tctcttaatg ctgacaacag gacttgtagt gctcctacga cttcctgct cttcagtcaa     2820 aagagtgcca tcaaccgcat ggtgattgat gaacaacaga gccccgacat catccttccc    2880
atccacagcc ttcggaatgt ccgggccatt gactatgacc cactggacaa gcaactctat    2940
tggattgact cacgacaaaa catgatccga aaggcacaag aagatggcag ccagggcttt    3000
actgtggttg tgagctcagt tccgagtcag aacctggaaa tacaacccta tgacctcagc    3060
attgatattt acagccgcta catctactgg acttgtgagg ctaccaatgt cattaatgtg    3120
acaagattag atggagagatc agttggagtg gtgctgaaag gcgagcagga cagacctcga    3180
gccattgtgg taaacccaga gaagggtat atgtattta ccaatcttca ggaaaggtct       3240
cctaaaattg aacgggctgc tttggatggg acagaacggg aggtcctctt tttcagtggc    3300
```

-continued

```
ttaagtaaac caattgcttt agcccttgat agcaggctgg gcaagctctt ttgggctgat      3360
tcagatctcc ggcgaattga aagcagtgat ctctcaggtg ctaaccggat agtattagaa      3420
gactccaata tcttgcagcc tgtgggactt actgtgtttg aaaactggct ctattggatt      3480
gataaacagc agcaaatgat tgaaaaaatt gacatgacag gtcgagaggg tagaaccaaa      3540
gtccaagctc gaattgccca gcttagtgac attcatgcag taaggagct gaaccttcaa       3600
gaatacagac agcacccttg tgctcaggat aatggtggct gttcacatat ttgtcttgta      3660
aagggggatg gtactacaag gtgttcttgc cccatgcacc tggttctact tcaagatgag      3720
ctatcatgtg gagaacctcc aacatgttct cctcagcagt ttacttgttt cacggggggaa     3780
attgactgta tccctgtggc ttggcggtgc gatgggttta ctgaatgtga agaccacagt      3840
gatgaactca attgtcctgt atgctcagag tcccagttcc agtgtgccag tgggcagtgt      3900
attgatggtg ccctccgatg caatggagat gcaaactgcc aggacaaatc agatgagaag      3960
aactgtgaag tgctttgttt aattgatcag ttccgctgtg ccaatggtca gtgcattgga      4020
aagcacaaga agtgtgatca taatgtggat tgcagtgaca agtcagatga actggattgt      4080
tatccgactg aagaaccagc accacaggcc accaatacag ttggttctgt tattggcgta     4140
attgtcacca ttttttgtgtc tggaactgta tactttatct gccagaggat gttgtgtcca    4200
cgtatgaagg gagatgggga aactatgact aatgactatg tagttcatgg accagcttct     4260
gtgcctcttg gttatgtgcc acacccaagt tctttgtcag gatctcttcc aggaatgtct     4320
cgaggtaaat caatgatcag ctccctcagt atcatggggg gaagcagtgg acccccctat      4380
gaccgagccc atgttacagg agcatcatca agtagttctt caagcaccaa aggcacttac      4440
ttccctgcaa ttttgaaccc tccaccatcc ccagccacag agcgatcaca ttacactatg      4500
gaatttggat attcttcaaa cagtccttcc actcataggt catacagcta caggccatat     4560
agctaccggc actttgcacc ccccaccaca ccctgcagca cagatgtttg tgacagtgac     4620
tatgctccta gtcggagaat gacctcagtg gcaacagcca aggctatac cagtgacttg    4680
aactatgatt cagaacctgt gccccacct cccacacccc gaagccaata cttgtcagca     4740
gaggagaact atgaaagctg cccaccttct ccatacacag agaggagcta ttctcatcac   4800
ctctacccac cgccacccct ccctgtaca gactcctcct ga                        4842
```

<210> SEQ ID NO 4
<211> LENGTH: 1613
<212> TYPE: PRT
<213> ORGANISM: Human

<400> SEQUENCE: 4

```
Met Gly Ala Val Leu Arg Ser Leu Leu Ala Cys Ser Phe Cys Val Leu
 1               5                  10                  15

Leu Arg Ala Ala Pro Leu Leu Leu Tyr Ala Asn Arg Arg Asp Leu Arg
                20                  25                  30

Leu Val Asp Ala Thr Asn Gly Lys Glu Asn Ala Thr Ile Val Val Gly
             35                  40                  45

Gly Leu Glu Asp Ala Ala Ala Val Asp Phe Val Phe Ser His Gly Leu
         50                  55                  60

Ile Tyr Trp Ser Asp Val Ser Glu Glu Ala Ile Lys Arg Thr Glu Phe
 65                  70                  75                  80

Asn Lys Thr Glu Ser Val Gln Asn Val Val Val Ser Gly Leu Leu Ser
                 85                  90                  95

Pro Asp Gly Leu Ala Cys Asp Trp Leu Gly Glu Lys Leu Tyr Trp Thr
```

-continued

```
                100                 105                 110
Asp Ser Glu Thr Asn Arg Ile Glu Val Ser Asn Leu Asp Gly Ser Leu
            115                 120                 125
Arg Lys Val Leu Phe Trp Gln Glu Leu Asp Gln Pro Arg Ala Ile Ala
    130                 135                 140
Leu Asp Pro Ser Ser Gly Phe Met Tyr Trp Thr Asp Trp Gly Glu Val
145                 150                 155                 160
Pro Lys Ile Glu Arg Ala Gly Met Asp Gly Ser Ser Arg Phe Ile Ile
                165                 170                 175
Ile Asn Ser Glu Ile Tyr Trp Pro Asn Gly Leu Thr Leu Asp Tyr Glu
            180                 185                 190
Glu Gln Lys Leu Tyr Trp Ala Asp Ala Lys Leu Asn Phe Ile His Lys
    195                 200                 205
Ser Asn Leu Asp Gly Thr Asn Arg Gln Ala Val Val Lys Gly Ser Leu
210                 215                 220
Pro His Pro Phe Ala Leu Thr Leu Phe Glu Asp Ile Leu Tyr Trp Thr
225                 230                 235                 240
Asp Trp Ser Thr His Ser Ile Leu Ala Cys Asn Lys Tyr Thr Gly Glu
                245                 250                 255
Gly Leu Arg Glu Ile His Ser Asp Ile Phe Ser Pro Met Asp Ile His
            260                 265                 270
Ala Phe Ser Gln Gln Arg Gln Pro Asn Ala Thr Asn Pro Cys Gly Ile
    275                 280                 285
Asp Asn Gly Gly Cys Ser His Leu Cys Leu Met Ser Pro Val Lys Pro
290                 295                 300
Phe Tyr Gln Cys Ala Cys Pro Thr Gly Val Lys Leu Leu Glu Asn Gly
305                 310                 315                 320
Lys Thr Cys Lys Asp Gly Ala Thr Glu Leu Leu Leu Ala Arg Arg
                325                 330                 335
Thr Asp Leu Arg Arg Ile Ser Leu Asp Thr Pro Asp Phe Thr Asp Ile
            340                 345                 350
Val Leu Gln Leu Glu Asp Ile Arg His Ala Ile Ala Ile Asp Tyr Asp
    355                 360                 365
Pro Val Glu Gly Tyr Ile Tyr Trp Thr Asp Asp Glu Val Arg Ala Ile
370                 375                 380
Arg Arg Ser Phe Ile Asp Gly Ser Gly Ser Gln Phe Val Val Thr Ala
385                 390                 395                 400
Gln Ile Ala His Pro Asp Gly Ile Ala Val Asp Trp Val Ala Arg Asn
                405                 410                 415
Leu Tyr Trp Thr Asp Thr Gly Thr Asp Arg Ile Glu Val Thr Arg Leu
            420                 425                 430
Asn Gly Thr Met Arg Lys Ile Leu Ile Ser Glu Asp Leu Glu Glu Pro
    435                 440                 445
Arg Ala Ile Val Leu Asp Pro Met Val Gly Tyr Met Tyr Trp Thr Asp
450                 455                 460
Trp Gly Glu Ile Pro Lys Ile Glu Arg Ala Ala Leu Asp Gly Ser Asp
465                 470                 475                 480
Arg Val Val Leu Val Asn Thr Ser Leu Gly Trp Pro Asn Gly Leu Ala
                485                 490                 495
Leu Asp Tyr Asp Glu Gly Lys Ile Tyr Trp Gly Asp Ala Lys Thr Asp
            500                 505                 510
Lys Ile Glu Val Met Asn Thr Asp Gly Thr Gly Arg Arg Val Leu Val
    515                 520                 525
```

```
Glu Asp Lys Ile Pro His Ile Phe Gly Phe Thr Leu Leu Gly Asp Tyr
    530                 535                 540
Val Tyr Trp Thr Asp Trp Gln Arg Arg Ser Ile Glu Arg Val His Lys
545                 550                 555                 560
Arg Ser Ala Glu Arg Glu Val Ile Ile Asp Gln Leu Pro Asp Leu Met
                565                 570                 575
Gly Leu Lys Ala Thr Asn Val His Arg Val Ile Gly Ser Asn Pro Cys
            580                 585                 590
Ala Glu Glu Asn Gly Gly Cys Ser His Leu Cys Leu Tyr Arg Pro Gln
        595                 600                 605
Gly Leu Arg Cys Ala Cys Pro Ile Gly Phe Glu Leu Ile Ser Asp Met
    610                 615                 620
Lys Thr Cys Ile Val Pro Glu Ala Phe Leu Leu Phe Ser Arg Arg Ala
625                 630                 635                 640
Asp Ile Arg Arg Ile Ser Leu Glu Thr Asn Asn Asn Asn Val Ala Ile
                645                 650                 655
Pro Leu Thr Gly Val Lys Glu Ala Ser Ala Leu Asp Phe Asp Val Thr
            660                 665                 670
Asp Asn Arg Ile Tyr Trp Thr Asp Ile Ser Leu Lys Thr Ile Ser Arg
        675                 680                 685
Ala Phe Met Asn Gly Ser Ala Leu Glu His Val Val Glu Phe Gly Leu
    690                 695                 700
Asp Tyr Pro Glu Gly Met Ala Val Asp Trp Leu Gly Lys Asn Leu Tyr
705                 710                 715                 720
Trp Ala Asp Thr Gly Thr Asn Arg Ile Glu Val Ser Lys Leu Asp Gly
                725                 730                 735
Gln His Arg Gln Val Leu Val Trp Lys Asp Leu Asp Ser Pro Arg Ala
            740                 745                 750
Leu Ala Leu Asp Pro Ala Glu Gly Phe Met Tyr Trp Thr Glu Trp Gly
        755                 760                 765
Gly Lys Pro Lys Ile Asp Arg Ala Ala Met Asp Gly Ser Glu Arg Thr
    770                 775                 780
Thr Leu Val Pro Asn Val Gly Arg Ala Asn Gly Leu Thr Ile Asp Tyr
785                 790                 795                 800
Ala Lys Arg Arg Leu Tyr Trp Thr Asp Leu Asp Thr Asn Leu Ile Glu
                805                 810                 815
Ser Ser Asn Met Leu Gly Leu Asn Arg Glu Val Ile Ala Asp Asp Leu
            820                 825                 830
Pro His Pro Phe Gly Leu Thr Gln Tyr Gln Asp Tyr Ile Tyr Trp Thr
        835                 840                 845
Asp Trp Ser Arg Arg Ser Ile Glu Arg Ala Asn Lys Thr Ser Gly Gln
    850                 855                 860
Asn Arg Thr Ile Ile Gln Gly His Leu Asp Tyr Val Met Asp Ile Leu
865                 870                 875                 880
Val Phe His Ser Ser Arg Gln Ser Gly Trp Asn Glu Cys Ala Ser Ser
                885                 890                 895
Asn Gly His Cys Ser His Leu Cys Leu Ala Val Pro Val Gly Gly Phe
            900                 905                 910
Val Cys Gly Cys Pro Ala His Tyr Ser Leu Asn Ala Asp Asn Arg Thr
        915                 920                 925
Cys Ser Ala Pro Thr Thr Phe Leu Leu Phe Ser Gln Lys Ser Ala Ile
    930                 935                 940
```

-continued

Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
            965                 970                 975

Lys Gln Leu Tyr Trp Ile Asp Ser Arg Gln Asn Met Ile Arg Lys Ala
            980                 985                 990

Gln Glu Asp Gly Ser Gln Gly Phe Thr Val Val Ser Ser Val Pro
        995                 1000                1005

Ser Gln Asn Leu Glu Ile Gln Pro Tyr Asp Leu Ser Ile Asp Ile
    1010                1015                1020

Tyr Ser Arg Tyr Ile Tyr Trp Thr Cys Glu Ala Thr Asn Val Ile
    1025                1030                1035

Asn Val Thr Arg Leu Asp Gly Arg Ser Val Gly Val Val Leu Lys
    1040                1045                1050

Gly Glu Gln Asp Arg Pro Arg Ala Ile Val Val Asn Pro Glu Lys
    1055                1060                1065

Gly Tyr Met Tyr Phe Thr Asn Leu Gln Glu Arg Ser Pro Lys Ile
    1070                1075                1080

Glu Arg Ala Ala Leu Asp Gly Thr Glu Arg Glu Val Leu Phe Phe
    1085                1090                1095

Ser Gly Leu Ser Lys Pro Ile Ala Leu Ala Leu Asp Ser Arg Leu
    1100                1105                1110

Gly Lys Leu Phe Trp Ala Asp Ser Asp Leu Arg Arg Ile Glu Ser
    1115                1120                1125

Ser Asp Leu Ser Gly Ala Asn Arg Ile Val Leu Glu Asp Ser Asn
    1130                1135                1140

Ile Leu Gln Pro Val Gly Leu Thr Val Phe Glu Asn Trp Leu Tyr
    1145                1150                1155

Trp Ile Asp Lys Gln Gln Gln Met Ile Glu Lys Ile Asp Met Thr
    1160                1165                1170

Gly Arg Glu Gly Arg Thr Lys Val Gln Ala Arg Ile Ala Gln Leu
    1175                1180                1185

Ser Asp Ile His Ala Val Lys Glu Leu Asn Leu Gln Glu Tyr Arg
    1190                1195                1200

Gln His Pro Cys Ala Gln Asp Asn Gly Gly Cys Ser His Ile Cys
    1205                1210                1215

Leu Val Lys Gly Asp Gly Thr Thr Arg Cys Ser Cys Pro Met His
    1220                1225                1230

Leu Val Leu Leu Gln Asp Glu Leu Ser Cys Gly Glu Pro Pro Thr
    1235                1240                1245

Cys Ser Pro Gln Gln Phe Thr Cys Phe Thr Gly Glu Ile Asp Cys
    1250                1255                1260

Ile Pro Val Ala Trp Arg Cys Asp Gly Phe Thr Glu Cys Glu Asp
    1265                1270                1275

His Ser Asp Glu Leu Asn Cys Pro Val Cys Ser Glu Ser Gln Phe
    1280                1285                1290

Gln Cys Ala Ser Gly Gln Cys Ile Asp Gly Ala Leu Arg Cys Asn
    1295                1300                1305

Gly Asp Ala Asn Cys Gln Asp Lys Ser Asp Glu Lys Asn Cys Glu
    1310                1315                1320

Val Leu Cys Leu Ile Asp Gln Phe Arg Cys Ala Asn Gly Gln Cys
    1325                1330                1335

Ile Gly Lys His Lys Lys Cys Asp His Asn Val Asp Cys Ser Asp

| | | | | | | | | |
|---|---|---|---|---|---|---|---|---|
| | 1340 | | | 1345 | | | 1350 | |
| Lys | Ser | Asp | Glu | Leu | Asp | Cys | Tyr | Pro | Thr | Glu | Glu | Pro | Ala | Pro |
| | 1355 | | | | 1360 | | | | 1365 | |

Gln Ala Thr Asn Thr Val Gly Ser Val Ile Gly Val Ile Val Thr
    1370                1375                1380

Ile Phe Val Ser Gly Thr Val Tyr Phe Ile Cys Gln Arg Met Leu
    1385                1390                1395

Cys Pro Arg Met Lys Gly Asp Gly Glu Thr Met Thr Asn Asp Tyr
    1400                1405                1410

Val Val His Gly Pro Ala Ser Val Pro Leu Gly Tyr Val Pro His
    1415                1420                1425

Pro Ser Ser Leu Ser Gly Ser Leu Pro Gly Met Ser Arg Gly Lys
    1430                1435                1440

Ser Met Ile Ser Ser Leu Ser Ile Met Gly Gly Ser Ser Gly Pro
    1445                1450                1455

Pro Tyr Asp Arg Ala His Val Thr Gly Ala Ser Ser Ser Ser Ser
    1460                1465                1470

Ser Ser Thr Lys Gly Thr Tyr Phe Pro Ala Ile Leu Asn Pro Pro
    1475                1480                1485

Pro Ser Pro Ala Thr Glu Arg Ser His Tyr Thr Met Glu Phe Gly
    1490                1495                1500

Tyr Ser Ser Asn Ser Pro Ser Thr His Arg Ser Tyr Ser Tyr Arg
    1505                1510                1515

Pro Tyr Ser Tyr Arg His Phe Ala Pro Pro Thr Thr Pro Cys Ser
    1520                1525                1530

Thr Asp Val Cys Asp Ser Asp Tyr Ala Pro Ser Arg Arg Met Thr
    1535                1540                1545

Ser Val Ala Thr Ala Lys Gly Tyr Thr Ser Asp Leu Asn Tyr Asp
    1550                1555                1560

Ser Glu Pro Val Pro Pro Pro Thr Pro Arg Ser Gln Tyr Leu
    1565                1570                1575

Ser Ala Glu Glu Asn Tyr Glu Ser Cys Pro Pro Ser Pro Tyr Thr
    1580                1585                1590

Glu Arg Ser Tyr Ser His His Leu Tyr Pro Pro Pro Ser Pro
    1595                1600                1605

Cys Thr Asp Ser Ser
    1610

```
<210> SEQ ID NO 5
<211> LENGTH: 4161
<212> TYPE: DNA
<213> ORGANISM: Human

<400> SEQUENCE: 5
atggaggcag cgccgcccgg gccgccgtgg ccgctgctgc tgctgctgct gctgctgctg      60
gcgctgtgcg gctgcccggc ccccgccgcg gcctcgccgc tcctgctatt tgccaaccgc     120
cgggacgtac ggctggtgga cgccggcgga gtcaagctgg agtccaccat cgtggtcagc     180
ggcctggagg atgcggccgc agtggacttc cagttttcca agggagccgt gtactggaca     240
gacgtgagcg aggaggccat caagcagacc tacctgaacc agacggggggc cgccgtgcag     300 aacgtggtca tctccggcct ggtctctccc gacggcctcg cctgcgactg ggtgggcaag     360
aagctgtact ggacggactc agagaccaac cgcatcgagg tggccaacct caatggcaca     420
tcccggaagg tgctcttctg gcaggacctt gaccagccga gggccatcgc cttggacccc     480
```

-continued

```
gctcacgggt acatgtactg gacagactgg ggtgagacgc cccgattga gcgggcaggg    540 atggatggca gcacccggaa gatcattgtg gactcggaca tttactggcc caatggactg    600
accatcgacc tggaggagca gaagctctac tgggctgacg ccaagctcag cttcatccac    660
cgtgccaacc tggacggctc gttccggcag aaggtggtgg agggcagcct gacgcacccc    720
ttcgccctga cgctctccgg ggacactctg tactggacag actggcagac ccgctccatc    780
catgcctgca caagcgcac tgggggaag aggaaggaga tcctgagtgc cctctactca    840
cccatggaca tccaggtgct gagccaggag cggcagcctt tcttccacac tcgctgtgag    900
gaggacaatg gcgctgctc ccacctgtgc ctgctgtccc caagcgagcc tttctacaca    960
tgcgcctgcc ccacgggtgt gcagctgcag gacaacggca ggacgtgtaa ggcaggagcc   1020
gaggaggtgc tgctgctggc ccggcggacg gacctacgga ggatctcgct ggacacgccg   1080
gactttaccg acatcgtgct gcaggtggac gacatccggc acgccattgc catcgactac   1140
gacccgctag agggctatgt ctactggaca gatgacgagg tgcgggccat ccgcagggcg   1200
tacctggacg ggtctggggc gcagacgctg gtcaacaccg agatcaacga ccccgatggc   1260
atcgcggtcg actgggtggc ccgaaacctc tactggaccg acacgggcac ggaccgcatc   1320
gaggtgacgc gcctcaacgg cacctcccgc aagatcctgg tgtcggagga cctggacgag   1380
ccccgagcca tcgcactgca ccccgtgatg ggcctcatgt actggacaga ctggggagag   1440
aaccctaaaa tcgagtgtgc caacttggat gggcaggagc ggcgtgtgct ggtcaatgcc   1500
tccctcgggt ggcccaacgg cctggccctg gacctgcagg aggggaagct ctactgggga   1560
gacgccaaga cagacaagat cgaggtgatc aatgttgatg ggacgaagag gcggaccctc   1620
ctggaggaca agctcccgca cattttcggg ttcacgctgc tgggggactt catctactgg   1680
actgactggc agcgccgcag catcgagcgg gtgcacaagg tcaaggccag ccgggacgtc   1740
atcattgacc agctgcccga cctgatgggg ctcaaagctg tgaatgtggc caaggtcgtc   1800
ggaaccaacc cgtgtgcgga caggaacggg gggtgcagcc acctgtgctt cttcacaccc   1860
cacgcaaccc ggtgtggctg ccccatcggc ctggagctgc tgagtgacat gaagacctgc   1920
atcgtgcctg aggccttctt ggtcttcacc agcagagccg ccatccacag gatctccctc   1980
gagaccaata caacgacgt ggccatcccg ctcacgggcg tcaaggaggc ctcagccctg   2040
gactttgatg tgtccaacaa ccacatctac tggacagacg tcagcctgaa gaccatcagc   2100
cgcgccttca tgaacgggag ctcggtggag cacgtggtgg agtttggcct tgactacccc   2160
gagggcatgc ccgttgactg gatgggcaag aacctctact gggccgacac tgggaccaac   2220
agaatcgaag tggcgcggct ggacgggcag ttccggcaag tcctcgtgtg gagggacttg   2280
gacaacccga ggtcgctggc cctggatccc accaagggct acatctactg gaccgagtgg   2340
ggcggcaagc cgaggatcgt gcgggccttc atggacggga ccaactgcat gacgctggtg   2400
gacaaggtgg gccgggccaa cgacctcacc attgactacg ctgaccagcg cctctactgg   2460
accgacctgg acaccaacat gatcgagtcg tccaacatgc tgggtcagga gcgggtcgtg   2520
attgccgacg atctcccgca cccgttcggt ctgacgcagt acagcgatta tatctactgg   2580
acagactgga atctgcacag cattgagcgg gccgacaaga ctagcggccg gaaccgcacc   2640
ctcatccagg gccacctgga cttcgtgatg gacatcctgg tgttccactc ctcccgccag   2700
gatggcctca atgactgtat gcacaacaac gggcagtgtg gcagctgtg ccttgccatc   2760 cccggcggcc accgctgcgg ctgcgcctca cactacaccc tggaccccag cagccgcaac   2820
```

```
tgcagcccgc ccaccacctt cttgctgttc agccagaaat ctgccatcag tcggatgatc    2880
ccggacgacc agcacagccc ggatctcatc ctgcccctgc atggactgag aacgtcaaa    2940 gccatcgact atgacccact ggacaagttc atctactggg tggatgggcg ccagaacatc    3000
aagcgagcca aggacgacgg gacccagccc tttgttttga cctctctgag ccaaggccaa    3060
aacccagaca ggcagcccca cgacctcagc atcgacatct acagccggac actgttctgg    3120
acgtgcgagg ccaccaatac catcaacgtc acaggctga gcggggaagc catgggggtg    3180
gtgctgcgtg gggaccgcga caagcccagg gccatcgtcg tcaacgcgga gcgagggtac    3240
ctgtacttca ccaacatgca ggaccgggca gccaagatcg aacgcgcagc cctggacggc    3300
accgagcgcg aggtcctctt caccaccggc ctcatccgcc ctgtggccct ggtggtagac    3360
aacacactgg gcaagctgtt ctgggtggac gcggacctga gcgcattga gctgtgac    3420 ctgtcagggg ccaaccgcct gaccctggag gacgccaaca tcgtgcagcc tctgggcctg    3480
accatccttg gcaagcatct ctactggatc gaccgccagc agcagatgat cgagcgtgtg    3540
gagaagacca ccggggacaa gcggactcgc atccaggggc cgtgtcgccca cctcactggc    3600 atccatgcag tggaggaagt cagcctggag gagttctcag cccacccatg tgcccgtgac    3660
aatggtggct gctcccacat ctgtattgcc aagggtgatg ggacaccacg gtgctcatgc    3720
ccagtccacc tcgtgctcct gcagaacctg ctgacctgtg agagccgcc cacctgctcc    3780 ccggaccagt ttgcatgtgc cacaggggag atcgactgta tccccggggc ctggcgctgt    3840
gacggctttc ccgagtgcga tgaccagagc gacgaggagg gctgccccgt gtgctccgcc    3900
gcccagttcc cctgcgcgcg gggtcagtgt gtggacctgc cctgcgctg cgacggcgag    3960 gcagactgtc aggaccgctc agacgaggcg gactgtgacg ccatctgcct gcccaaccag    4020
ttccggtgtg cgagcggcca gtgtgtcctc atcaaacagc agtgcgactc cttccccgac    4080
tgtatcgacg gctccgacga gctcatgtgt gaaatcacca gccgcccctc agacgacagc    4140
ccggcccaca gcagtgccat c                                              4161
```

<210> SEQ ID NO 6
<211> LENGTH: 1383
<212> TYPE: PRT
<213> ORGANISM: Human

<400> SEQUENCE: 6

```
Met Glu Ala Ala Pro Gly Pro Pro Trp Pro Leu Leu Leu Leu Leu
1               5                   10                  15

Leu Leu Leu Leu Ala Leu Cys Gly Cys Pro Ala Pro Ala Ala Ala Ser
                20                  25                  30

Pro Leu Leu Leu Phe Ala Asn Arg Arg Asp Val Arg Leu Val Asp Ala
            35                  40                  45

Gly Gly Val Lys Leu Glu Ser Thr Ile Val Val Ser Gly Leu Glu Asp
        50                  55                  60

Ala Ala Ala Val Asp Phe Gln Phe Ser Lys Gly Ala Val Tyr Trp Thr
65                  70                  75                  80

Asp Val Ser Glu Glu Ala Ile Lys Gln Thr Tyr Leu Asn Gln Thr Gly
                85                  90                  95

Ala Ala Val Gln Asn Val Val Ile Ser Gly Leu Val Ser Pro Asp Gly
            100                 105                 110

Leu Ala Cys Asp Trp Val Gly Lys Lys Leu Tyr Trp Thr Asp Ser Glu
        115                 120                 125

Thr Asn Arg Ile Glu Val Ala Asn Leu Asn Gly Thr Ser Arg Lys Val
```

```
                130             135             140
Leu Phe Trp Gln Asp Leu Asp Gln Pro Arg Ala Ile Ala Leu Asp Pro
145                 150                 155                 160

Ala His Gly Tyr Met Tyr Trp Thr Asp Trp Gly Glu Thr Pro Arg Ile
                165                 170                 175

Glu Arg Ala Gly Met Asp Gly Ser Thr Arg Lys Ile Ile Val Asp Ser
            180                 185                 190

Asp Ile Tyr Trp Pro Asn Gly Leu Thr Ile Asp Leu Glu Glu Gln Lys
        195                 200                 205

Leu Tyr Trp Ala Asp Ala Lys Leu Ser Phe Ile His Arg Ala Asn Leu
    210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                245                 250                 255

Thr Arg Ser Ile His Ala Cys Asn Lys Arg Thr Gly Gly Lys Arg Lys
            260                 265                 270

Glu Ile Leu Ser Ala Leu Tyr Ser Pro Met Asp Ile Gln Val Leu Ser
        275                 280                 285

Gln Glu Arg Gln Pro Phe Phe His Thr Arg Cys Glu Glu Asp Asn Gly
    290                 295                 300

Gly Cys Ser His Leu Cys Leu Leu Ser Pro Ser Glu Pro Phe Tyr Thr
305                 310                 315                 320

Cys Ala Cys Pro Thr Gly Val Gln Leu Gln Asp Asn Gly Arg Thr Cys
                325                 330                 335

Lys Ala Gly Ala Glu Glu Val Leu Leu Leu Ala Arg Arg Thr Asp Leu
            340                 345                 350

Arg Arg Ile Ser Leu Asp Thr Pro Asp Phe Thr Asp Ile Val Leu Gln
        355                 360                 365

Val Asp Asp Ile Arg His Ala Ile Ala Ile Asp Tyr Asp Pro Leu Glu
    370                 375                 380

Gly Tyr Val Tyr Trp Thr Asp Asp Glu Val Arg Ala Ile Arg Arg Ala
385                 390                 395                 400

Tyr Leu Asp Gly Ser Gly Ala Gln Thr Leu Val Asn Thr Glu Ile Asn
                405                 410                 415

Asp Pro Asp Gly Ile Ala Val Asp Trp Val Ala Arg Asn Leu Tyr Trp
            420                 425                 430

Thr Asp Thr Gly Thr Asp Arg Ile Glu Val Thr Arg Leu Asn Gly Thr
        435                 440                 445

Ser Arg Lys Ile Leu Val Ser Glu Asp Leu Asp Glu Pro Arg Ala Ile
    450                 455                 460

Ala Leu His Pro Val Met Gly Leu Met Tyr Trp Thr Asp Trp Gly Glu
465                 470                 475                 480

Asn Pro Lys Ile Glu Cys Ala Asn Leu Asp Gly Gln Glu Arg Arg Val
                485                 490                 495

Leu Val Asn Ala Ser Leu Gly Trp Pro Asn Gly Leu Ala Leu Asp Leu
            500                 505                 510

Gln Glu Gly Lys Leu Tyr Trp Gly Asp Ala Lys Thr Asp Lys Ile Glu
        515                 520                 525

Val Ile Asn Val Asp Gly Thr Lys Arg Arg Thr Leu Leu Glu Asp Lys
    530                 535                 540

Leu Pro His Ile Phe Gly Phe Thr Leu Leu Gly Asp Phe Ile Tyr Trp
545                 550                 555                 560
```

```
Thr Asp Trp Gln Arg Arg Ser Ile Glu Arg Val His Lys Val Lys Ala
                565                 570                 575
Ser Arg Asp Val Ile Ile Asp Gln Leu Pro Asp Leu Met Gly Leu Lys
            580                 585                 590
Ala Val Asn Val Ala Lys Val Val Gly Thr Asn Pro Cys Ala Asp Arg
        595                 600                 605
Asn Gly Gly Cys Ser His Leu Cys Phe Phe Thr Pro His Ala Thr Arg
    610                 615                 620
Cys Gly Cys Pro Ile Gly Leu Glu Leu Leu Ser Asp Met Lys Thr Cys
625                 630                 635                 640
Ile Val Pro Glu Ala Phe Leu Val Phe Thr Ser Arg Ala Ala Ile His
                645                 650                 655
Arg Ile Ser Leu Glu Thr Asn Asn Asn Asp Val Ala Ile Pro Leu Thr
            660                 665                 670
Gly Val Lys Glu Ala Ser Ala Leu Asp Phe Asp Val Ser Asn Asn His
        675                 680                 685
Ile Tyr Trp Thr Asp Val Ser Leu Lys Thr Ile Ser Arg Ala Phe Met
    690                 695                 700
Asn Gly Ser Ser Val Glu His Val Val Glu Phe Gly Leu Asp Tyr Pro
705                 710                 715                 720
Glu Gly Met Ala Val Asp Trp Met Gly Lys Asn Leu Tyr Trp Ala Asp
                725                 730                 735
Thr Gly Thr Asn Arg Ile Glu Val Ala Arg Leu Asp Gly Gln Phe Arg
            740                 745                 750
Gln Val Leu Val Trp Arg Asp Leu Asp Asn Pro Arg Ser Leu Ala Leu
        755                 760                 765
Asp Pro Thr Lys Gly Tyr Ile Tyr Trp Thr Glu Trp Gly Gly Lys Pro
    770                 775                 780
Arg Ile Val Arg Ala Phe Met Asp Gly Thr Asn Cys Met Thr Leu Val
785                 790                 795                 800
Asp Lys Val Gly Arg Ala Asn Asp Leu Thr Ile Asp Tyr Ala Asp Gln
                805                 810                 815
Arg Leu Tyr Trp Thr Asp Leu Asp Thr Asn Met Ile Glu Ser Ser Asn
            820                 825                 830
Met Leu Gly Gln Glu Arg Val Val Ile Ala Asp Asp Leu Pro His Pro
        835                 840                 845
Phe Gly Leu Thr Gln Tyr Ser Asp Tyr Ile Tyr Trp Thr Asp Trp Asn
    850                 855                 860
Leu His Ser Ile Glu Arg Ala Asp Lys Thr Ser Gly Arg Asn Arg Thr
865                 870                 875                 880
Leu Ile Gln Gly His Leu Asp Phe Val Met Asp Ile Leu Val Phe His
                885                 890                 895
Ser Ser Arg Gln Asp Gly Leu Asn Asp Cys Met His Asn Asn Gly Gln
            900                 905                 910
Cys Gly Gln Leu Cys Leu Ala Ile Pro Gly Gly His Arg Cys Gly Cys
        915                 920                 925
Ala Ser His Tyr Thr Leu Asp Pro Ser Ser Arg Asn Cys Ser Pro Pro
    930                 935                 940
Thr Thr Phe Leu Leu Phe Ser Gln Lys Ser Ala Ile Ser Arg Met Ile
945                 950                 955                 960
Pro Asp Asp Gln His Ser Pro Asp Leu Ile Leu Pro Leu His Gly Leu
                965                 970                 975
```

-continued

Arg Asn Val Lys Ala Ile Asp Tyr Asp Pro Leu Asp Lys Phe Ile Tyr
            980                 985                 990

Trp Val Asp Gly Arg Gln Asn Ile Lys Arg Ala Lys Asp Asp Gly Thr
            995                 1000                1005

Gln Pro Phe Val Leu Thr Ser Leu Ser Gln Gly Gln Asn Pro Asp
    1010                1015                1020

Arg Gln Pro His Asp Leu Ser Ile Asp Ile Tyr Ser Arg Thr Leu
    1025                1030                1035

Phe Trp Thr Cys Glu Ala Thr Asn Thr Ile Asn Val His Arg Leu
    1040                1045                1050

Ser Gly Glu Ala Met Gly Val Val Leu Arg Gly Asp Arg Asp Lys
    1055                1060                1065

Pro Arg Ala Ile Val Val Asn Ala Glu Arg Gly Tyr Leu Tyr Phe
    1070                1075                1080

Thr Asn Met Gln Asp Arg Ala Ala Lys Ile Glu Arg Ala Ala Leu
    1085                1090                1095

Asp Gly Thr Glu Arg Glu Val Leu Phe Thr Thr Gly Leu Ile Arg
    1100                1105                1110

Pro Val Ala Leu Val Val Asp Asn Thr Leu Gly Lys Leu Phe Trp
    1115                1120                1125

Val Asp Ala Asp Leu Lys Arg Ile Glu Ser Cys Asp Leu Ser Gly
    1130                1135                1140

Ala Asn Arg Leu Thr Leu Glu Asp Ala Asn Ile Val Gln Pro Leu
    1145                1150                1155

Gly Leu Thr Ile Leu Gly Lys His Leu Tyr Trp Ile Asp Arg Gln
    1160                1165                1170

Gln Gln Met Ile Glu Arg Val Glu Lys Thr Thr Gly Asp Lys Arg
    1175                1180                1185

Thr Arg Ile Gln Gly Arg Val Ala His Leu Thr Gly Ile His Ala
    1190                1195                1200

Val Glu Glu Val Ser Leu Glu Glu Phe Ser Ala His Pro Cys Ala
    1205                1210                1215

Arg Asp Asn Gly Gly Cys Ser His Ile Cys Ile Ala Lys Gly Asp
    1220                1225                1230

Gly Thr Pro Arg Cys Ser Cys Pro Val His Leu Val Leu Leu Gln
    1235                1240                1245

Asn Leu Leu Thr Cys Gly Glu Pro Pro Thr Cys Ser Pro Asp Gln
    1250                1255                1260

Phe Ala Cys Ala Thr Gly Glu Ile Asp Cys Ile Pro Gly Ala Trp
    1265                1270                1275

Arg Cys Asp Gly Phe Pro Glu Cys Asp Asp Gln Ser Asp Glu Glu
    1280                1285                1290

Gly Cys Pro Val Cys Ser Ala Ala Gln Phe Pro Cys Ala Arg Gly
    1295                1300                1305

Gln Cys Val Asp Leu Arg Leu Arg Cys Asp Gly Glu Ala Asp Cys
    1310                1315                1320

Gln Asp Arg Ser Asp Glu Ala Asp Cys Asp Ala Ile Cys Leu Pro
    1325                1330                1335

Asn Gln Phe Arg Cys Ala Ser Gly Gln Cys Val Leu Ile Lys Gln
    1340                1345                1350

Gln Cys Asp Ser Phe Pro Cys Ile Asp Gly Ser Asp Glu Leu
    1355                1360                1365

Met Cys Glu Ile Thr Lys Pro Pro Ser Asp Ser Pro Ala His 1370        1375        1380

<210> SEQ ID NO 7
<211> LENGTH: 4161
<212> TYPE: DNA
<213> ORGANISM: Mouse

<400> SEQUENCE: 7

| | | | | | |
|---|---|---|---|---|---|
| atggaggcag | cgccgcccgg | gccgccgtgg | ccgctgctgc | tgctgctgct | gctgctgctg | 60 |
| gcgctgtgcg | gctgcccggc | cccgccgcg | gcctcgccgc | tcctgctatt | tgccaaccgc | 120 |
| cgggacgtac | ggctggtgga | cgccggcgga | gtcaagctgg | agtccaccat | cgtggtcagc | 180 |
| ggcctggagg | atgcggccgc | agtggacttc | cagtttttcca | aggagccgt | gtactggaca | 240 |
| gacgtgagcg | aggaggccat | caagcagacc | tacctgaacc | agacggggc | cgccgtgcag | 300 |
| aacgtggtca | tctccggcct | ggtctctccc | gacggcctcg | cctgcgactg | ggtgggcaag | 360 |
| aagctgtact | ggacggactc | agagaccaac | cgcatcgagg | tggccaacct | caatggcaca | 420 |
| tcccggaagg | tgctcttctg | gcaggacctt | gaccagccga | gggccatcgc | cttgacccc | 480 |
| gctcacgggt | acatgtactg | gacagactgg | ggtgagacgc | cccggattga | gcgggcaggg | 540 |
| atggatggca | gcacccggaa | gatcattgtg | gactcggaca | tttactggcc | caatggactg | 600 |
| accatcgacc | tggaggagca | gaagctctac | tgggctgacg | ccaagctcag | cttcatccac | 660 |
| cgtgccaacc | tggacggctc | gttccggcag | aaggtggtgg | agggcagcct | gacgcacccc | 720 |
| ttcgccctga | cgctctccgg | ggacactctg | tactggacag | actggcagac | ccgctccatc | 780 |
| catgcctgca | caagcgcac | tgggggggaag | aggaaggaga | tcctgagtgc | cctctactca | 840 |
| cccatggaca | tccaggtgct | gagccaggag | cggcagcctt | tcttccacac | tcgctgtgag | 900 |
| gaggacaatg | gcggctgctc | ccacctgtgc | ctgctgtccc | caagcgagcc | tttctacaca | 960 |
| tgcgcctgcc | ccacgggtgt | gcagctgcag | acaacggca | ggacgtgtaa | ggcaggagcc | 1020 |
| gaggaggtgc | tgctgctggc | ccggcggacg | gacctacgga | ggatctcgct | ggacacgccg | 1080 |
| gactttaccg | acatcgtgct | gcaggtggac | gacatccggc | acgccattgc | catcgactac | 1140 |
| gacccgctag | agggctatgt | ctactggaca | gatgacgagg | tgcgggccat | ccgcagggcg | 1200 |
| tacctggacg | ggtctggggc | gcagacgctg | gtcaacaccg | agatcaacga | ccccgatggc | 1260 |
| atcgcggtcg | actgggtggc | ccgaaacctc | tactggaccg | cacgggcac | ggaccgcatc | 1320 |
| gaggtgacgc | gcctcaacgg | cacctcccgc | aagatcctgg | tgtcggagga | cctggacgag | 1380 |
| ccccgagcca | tcgcactgca | ccccgtgatg | ggcctcatgt | actggacaga | ctggggagag | 1440 |
| aaccctaaaa | tcgagtgtgc | caacttggat | gggcaggagc | ggcgtgtgct | ggtcaatgcc | 1500 |
| tccctcgggt | ggcccaacgg | cctggccctg | acctgcagg | aggggaagct | ctactgggga | 1560 |
| gacgccaaga | cagacaagat | cgaggtgatc | aatgttgatg | ggacgaagag | gcggaccctc | 1620 |
| ctggaggaca | agctcccgca | catttttcggg | ttcacgctgc | tggggacctt | catctactgg | 1680 |
| actgactggc | agccgcag | catcgagcgg | gtgcacaagg | tcaaggccag | ccgggacgtc | 1740 |
| atcattgacc | agctgcccga | cctgatgggg | ctcaaagctg | tgaatgtggc | caaggtcgtc | 1800 |
| ggaaccaacc | cgtgtgcgga | caggaacggg | gggtgcagcc | acctgtgctt | cttcacaccc | 1860 |
| cacgcaaccc | ggtgtggctg | ccccatcggc | ctggagctgc | tgagtgacat | gaagacctgc | 1920 |
| atcgtgcctg | aggccttctt | ggtcttcacc | agcagagccg | ccatccacag | gatctccctc | 1980 |
| gagaccaata | caacgacgt | ggccatcccg | ctcacgggcg | tcaaggaggc | ctcagccctg | 2040 |
| gactttgatg | tgtccaacaa | ccacatctac | tggacagacg | tcagcctgaa | gaccatcagc | 2100 |

```
cgcgccttca tgaacgggag ctcggtggag cacgtggtgg agtttggcct tgactacccc    2160
gagggcatgg ccgttgactg gatgggcaag aacctctact gggccgacac tgggaccaac    2220
agaatcgaag tggcgcggct ggacgggcag ttccggcaag tcctcgtgtg agggacttg     2280 gacaacccga ggtcgctggc cctggatccc accaagggct acatctactg gaccgagtgg    2340
ggcggcaagc cgaggatcgt gcgggccttc atggacggga ccaactgcat gacgctggtg    2400
gacaaggtgg gccgggccaa cgacctcacc attgactacg ctgaccagcg cctctactgg    2460
accgacctgg acaccaacat gatcgagtcg tccaacatgc tgggtcagga gcgggtcgtg    2520
attgccgacg atctcccgca cccgttcggt ctgacgcagt acagcgatta tatctactgg    2580
acagactgga atctgcacag cattgagcgg gccgacaaga ctagcggccg gaaccgcacc    2640
ctcatccagg gccacctgga cttcgtgatg gacatcctgg tgttccactc ctcccgccag    2700
gatggcctca atgactgtat gcacaacaac gggcagtgtg ggcagctgtg ccttgccatc    2760 cccgcggcc accgctgcgg ctgcgcctca cactacaccc tggacccag cagccgcaac      2820 tgcagcccgc ccaccacctt cttgctgttc agccagaaat ctgccatcag tcggatgatc    2880
ccggacgacc agcacagccc ggatctcatc ctgcccctgc atggactgag gaacgtcaaa    2940
gccatcgact atgacccact ggacaagttc atctactggg tggatgggcg ccagaacatc    3000
aagcgagcca aggacgacgg gacccagccc tttgttttga cctctctgag ccaaggccaa    3060
aacccagaca ggcagcccca cgacctcagc atcgacatct acagccggac actgttctgg    3120
acgtgcgagg ccaccaatac catcaacgtc acaggctga gcggggaagc catgggggtg     3180
gtgctgcgtg gggaccgcga caagcccagg gccatcgtcg tcaacgcgga gcgagggtac    3240
ctgtacttca ccaacatgca ggaccgggca gccaagatcg aacgcgcagc cctggacggc    3300
accgagcgcg aggtcctctt caccaccggc ctcatccgcc ctgtggccct ggtggtagac    3360
aacacactgg gcaagctgtt ctgggtggac gcggacctga gcgcattga gagctgtgac    3420 ctgtcagggg ccaaccgcct gaccctggag gacgccaaca tcgtgcagcc tctgggcctg    3480
accatccttg gcaagcatct ctactggatc gaccgccagc agcagatgat cgagcgtgtg    3540
gagaagacca ccggggacaa gcggactcgc atccagggcc gtgtcgccca cctcactggc    3600
atccatgcag tggaggaagt cagcctggag gagttctcag cccacccatg tgcccgtgac    3660
aatggtggct gctcccacat ctgtattgcc aagggtgatg gcaccacg gtgctcatgc      3720 ccagtccacc tcgtgctcct gcagaacctg ctgacctgtg agagccgcc cacctgctcc    3780 ccggaccagt ttgcatgtgc cacagggag atcgactgta tccccggggc ctggcgctgt    3840
gacggctttc ccgagtgcga tgaccagagc gacgaggagg ctgccccgt gtgctccgcc    3900 gcccagttcc cctgcgcgcg gggtcagtgt gtggacctgc cctgcgctg cgacggcgag    3960 gcagactgtc aggaccgctc agacgaggcg gactgtgacg ccatctgcct gcccaaccag    4020
ttccggtgtg cgacggcca gtgtgtcctc atcaaacagc agtgcgactc cttccccgac    4080
tgtatcgacg gctccgacga gctcatgtgt gaaatcacca agccgccctc agacgacagc    4140
ccggcccaca gcagtgccat c                                              4161
```

<210> SEQ ID NO 8
<211> LENGTH: 4842
<212> TYPE: PRT
<213> ORGANISM: Mouse

<400> SEQUENCE: 8

-continued

```
Ala Thr Gly Gly Gly Gly Gly Cys Cys Gly Thr Gly Cys Thr Gly Ala
1               5                   10                  15

Gly Gly Ala Gly Cys Cys Thr Cys Cys Thr Gly Gly Cys Cys Thr Gly
            20                  25                  30

Cys Ala Gly Cys Thr Thr Cys Thr Gly Cys Gly Thr Gly Cys Thr Gly
        35                  40                  45

Cys Thr Gly Ala Gly Ala Gly Cys Gly Gly Cys Cys Cys Cys Thr Thr
    50                  55                  60

Thr Gly Thr Thr Gly Cys Thr Thr Thr Ala Thr Gly Cys Ala Ala Ala
65                  70                  75                  80

Cys Ala Gly Ala Cys Gly Gly Gly Ala Cys Thr Thr Gly Ala Gly Ala
                85                  90                  95

Thr Thr Gly Gly Thr Thr Gly Ala Thr Gly Cys Thr Ala Cys Ala Ala
            100                 105                 110

Ala Thr Gly Gly Cys Ala Ala Ala Gly Ala Gly Ala Ala Thr Gly Cys
        115                 120                 125

Ala Ala Cys Gly Ala Thr Thr Gly Thr Ala Gly Thr Thr Gly Gly Ala
    130                 135                 140

Gly Gly Cys Thr Thr Gly Gly Ala Gly Gly Ala Thr Gly Cys Ala Gly
145                 150                 155                 160

Cys Thr Gly Cys Gly Gly Thr Gly Gly Ala Cys Thr Thr Thr Gly Thr
                165                 170                 175

Gly Thr Thr Thr Gly Gly Thr Cys Ala Thr Gly Gly Cys Thr Thr Gly
            180                 185                 190

Ala Thr Ala Thr Ala Cys Thr Gly Gly Ala Gly Thr Gly Ala Thr Gly
        195                 200                 205

Thr Cys Ala Gly Cys Gly Ala Ala Gly Ala Ala Gly Cys Cys Ala Thr
    210                 215                 220

Thr Ala Ala Ala Cys Gly Ala Ala Cys Ala Gly Ala Ala Thr Thr Thr
225                 230                 235                 240

Ala Ala Cys Ala Ala Ala Ala Gly Thr Gly Ala Ala Ala Gly Thr Gly
                245                 250                 255

Thr Ala Cys Ala Gly Ala Ala Thr Gly Thr Thr Gly Thr Thr Gly Thr
            260                 265                 270

Thr Thr Cys Thr Gly Gly Ala Thr Thr Ala Thr Thr Gly Thr Cys Cys
        275                 280                 285

Cys Cys Gly Gly Ala Thr Gly Gly Gly Cys Thr Gly Gly Cys Ala Thr
    290                 295                 300

Gly Thr Gly Ala Thr Thr Gly Gly Cys Thr Thr Gly Gly Ala Gly Ala
305                 310                 315                 320

Ala Ala Ala Ala Thr Thr Gly Thr Ala Cys Thr Gly Gly Ala Cys Ala
                325                 330                 335

Gly Ala Thr Thr Cys Thr Gly Ala Ala Ala Cys Thr Ala Ala Thr Cys
            340                 345                 350

Gly Thr Ala Thr Thr Gly Ala Ala Gly Thr Thr Thr Cys Thr Ala Ala
        355                 360                 365

Thr Thr Thr Ala Gly Ala Thr Gly Gly Ala Thr Cys Thr Thr Thr Ala
    370                 375                 380

Cys Gly Ala Ala Ala Ala Gly Thr Thr Thr Thr Ala Thr Thr Thr Thr
385                 390                 395                 400

Gly Gly Cys Ala Ala Gly Ala Gly Thr Thr Gly Gly Ala Thr Cys Ala
                405                 410                 415

Ala Cys Cys Cys Ala Gly Ala Gly Cys Thr Ala Thr Thr Gly Cys Cys
```

```
            420                 425                 430
Thr Thr Ala Gly Ala Thr Cys Cys Ala Thr Cys Ala Ala Gly Thr Gly
            435                 440                 445
Gly Gly Thr Thr Cys Ala Thr Gly Thr Ala Cys Thr Gly Gly Ala Cys
            450                 455                 460
Ala Gly Ala Cys Thr Gly Gly Gly Ala Gly Ala Ala Gly Thr Gly
465                 470                 475                 480
Cys Cys Ala Ala Ala Gly Ala Thr Ala Gly Ala Ala Cys Gly Gly Gly
                    485                 490                 495
Cys Thr Gly Gly Gly Ala Thr Gly Gly Ala Thr Gly Gly Cys Thr Cys
                    500                 505                 510
Ala Ala Gly Thr Cys Gly Cys Thr Thr Cys Gly Thr Ala Thr Ala
            515                 520                 525
Ala Thr Ala Ala Ala Cys Ala Cys Gly Gly Ala Gly Ala Thr Thr Thr
            530                 535                 540
Ala Cys Thr Gly Gly Cys Cys Ala Ala Ala Cys Gly Gly Ala Cys Thr
545                 550                 555                 560
Gly Ala Cys Thr Cys Thr Gly Gly Ala Thr Thr Ala Thr Cys Ala Gly
                    565                 570                 575
Gly Ala Gly Cys Gly Gly Ala Ala Gly Cys Thr Thr Thr Ala Cys Thr
                    580                 585                 590
Gly Gly Gly Cys Cys Gly Ala Thr Gly Cys Ala Ala Ala Cys Thr
            595                 600                 605
Thr Ala Ala Thr Thr Thr Cys Ala Thr Cys Cys Ala Thr Ala Ala Ala
            610                 615                 620
Thr Cys Ala Ala Ala Cys Cys Thr Gly Gly Ala Thr Gly Gly Ala Ala
625                 630                 635                 640
Cys Ala Ala Ala Cys Cys Gly Gly Cys Ala Gly Gly Cys Ala Gly Thr
                    645                 650                 655
Gly Gly Thr Thr Ala Ala Ala Gly Gly Thr Thr Cys Cys Cys Thr Thr
                    660                 665                 670
Cys Cys Ala Cys Ala Thr Cys Cys Thr Thr Thr Thr Gly Cys Cys Thr
            675                 680                 685
Thr Gly Ala Cys Gly Thr Thr Ala Thr Thr Thr Gly Ala Gly Gly Ala
            690                 695                 700
Cys Ala Cys Ala Thr Thr Gly Thr Ala Cys Thr Gly Gly Ala Cys Thr
705                 710                 715                 720
Gly Ala Cys Thr Gly Gly Ala Ala Thr Ala Cys Ala Cys Ala Cys Thr
                    725                 730                 735
Cys Thr Ala Thr Thr Thr Thr Gly Gly Cys Thr Thr Gly Cys Ala Ala
            740                 745                 750
Cys Ala Ala Ala Thr Ala Thr Ala Cys Thr Gly Gly Cys Gly Ala Gly
            755                 760                 765
Gly Gly Thr Cys Thr Gly Cys Gly Thr Gly Ala Ala Ala Thr Thr Cys
            770                 775                 780
Ala Thr Thr Cys Thr Ala Ala Cys Ala Thr Cys Thr Thr Cys Thr Cys
785                 790                 795                 800
Thr Cys Cys Cys Ala Thr Gly Gly Ala Thr Ala Thr Ala Cys Ala Thr
                    805                 810                 815
Gly Cys Thr Thr Thr Cys Ala Gly Cys Cys Ala Ala Cys Ala Gly Ala
            820                 825                 830
Gly Gly Cys Ala Gly Cys Cys Ala Ala Ala Thr Gly Cys Thr Ala Cys
            835                 840                 845
```

-continued

```
Ala Ala Ala Thr Cys Cys Ala Thr Gly Thr Gly Gly Ala Ala Thr Thr
    850                 855                 860

Gly Ala Thr Ala Ala Thr Gly Gly Thr Gly Gly Thr Thr Gly Thr Thr
865                 870                 875                 880

Cys Cys Cys Ala Thr Thr Thr Gly Thr Gly Thr Thr Thr Gly Ala Thr
                885                 890                 895
Gly Thr Cys Thr Cys Cys Ala Gly Thr Cys Ala Ala Gly Cys Cys Thr
            900                 905                 910

Thr Thr Thr Thr Ala Thr Cys Ala Gly Thr Gly Thr Gly Cys Thr Thr
        915                 920                 925

Gly Cys Cys Cys Ala Ala Cys Thr Gly Gly Gly Gly Thr Cys Ala Ala
    930                 935                 940

Gly Cys Thr Gly Ala Thr Gly Gly Ala Gly Ala Ala Thr Gly Gly Ala
945                 950                 955                 960
Ala Ala Gly Ala Cys Cys Thr Gly Cys Ala Ala Ala Gly Ala Thr Gly
                965                 970                 975
Gly Thr Gly Cys Cys Ala Cys Thr Gly Ala Ala Cys Thr Ala Thr Thr
            980                 985                 990

Gly Cys Thr Gly Thr Thr Ala Gly  Cys Cys Cys Gly Ala  Cys Gly Gly
        995                 1000                1005

Ala Cys  Ala Gly Ala Cys Thr  Thr Gly Ala Gly Gly  Cys Gly Ala
    1010                1015                1020

Ala Thr  Thr Thr Cys Thr Thr  Thr Gly Gly Ala Thr  Ala Cys Ala
    1025                1030                1035

Cys Cys  Cys Gly Ala Thr Thr  Thr Thr Ala Cys Thr  Gly Ala Cys
    1040                1045                1050

Ala Thr  Thr Gly Thr Thr Cys  Thr Gly Cys Ala Gly  Thr Thr Ala
    1055                1060                1065

Gly Ala  Ala Gly Ala Thr Ala  Thr Cys Cys Gly Gly  Cys Ala Thr
    1070                1075                1080

Gly Cys  Cys Ala Thr Thr Gly  Cys Cys Ala Thr Ala  Gly Ala Cys
    1085                1090                1095

Thr Ala  Thr Gly Ala Cys Cys  Cys Thr Gly Thr Ala  Gly Ala Ala
    1100                1105                1110

Gly Gly  Cys Thr Ala Cys Ala  Thr Ala Thr Ala Cys  Thr Gly Gly
    1115                1120                1125

Ala Cys  Ala Gly Ala Thr Gly  Ala Cys Gly Ala Ala  Gly Thr Gly
    1130                1135                1140

Ala Gly  Gly Gly Cys Thr Ala  Thr Cys Cys Gly Thr  Cys Gly Cys
    1145                1150                1155

Thr Cys  Cys Thr Thr Cys Ala  Thr Ala Gly Ala Thr  Gly Gly Ala
    1160                1165                1170

Thr Cys  Thr Gly Gly Cys Ala  Gly Thr Cys Ala Gly  Thr Thr Thr
    1175                1180                1185

Gly Thr  Gly Gly Thr Cys Ala  Cys Gly Gly Cys Cys  Cys Ala Gly
    1190                1195                1200

Ala Thr  Thr Gly Cys Thr Cys  Ala Thr Cys Cys Thr  Gly Ala Thr
    1205                1210                1215

Gly Gly  Thr Ala Thr Thr Gly  Cys Thr Gly Thr Thr  Gly Ala Cys
    1220                1225                1230

Thr Gly  Gly Gly Thr Thr Gly  Cys Ala Ala Gly Gly  Ala Ala Cys
    1235                1240                1245
```

-continued

Cys Thr Gly Thr Ala Cys Thr Gly Gly Ala Cys Ala Gly Ala Cys
1250 1255 1260

Ala Cys Thr Gly Gly Cys Ala Cys Gly Gly Ala Thr Cys Gly Thr
1265 1270 1275

Ala Thr Ala Gly Ala Ala Gly Thr Gly Ala Cys Ala Ala Gly Gly
1280 1285 1290

Cys Thr Cys Ala Ala Thr Gly Gly Gly Ala Cys Cys Ala Thr Gly
1295 1300 1305

Ala Gly Gly Ala Ala Gly Ala Thr Cys Thr Thr Gly Ala Thr Thr
1310 1315 1320

Thr Cys Ala Gly Ala Gly Gly Ala Cys Thr Thr Ala Gly Ala Gly
1325 1330 1335

Gly Ala Gly Cys Cys Cys Cys Gly Gly Gly Cys Thr Ala Thr Cys
1340 1345 1350

Gly Thr Gly Thr Thr Ala Gly Ala Thr Cys Cys Cys Ala Thr Gly
1355 1360 1365

Gly Thr Thr Gly Gly Gly Thr Ala Cys Ala Thr Gly Thr Ala Thr
1370 1375 1380

Thr Gly Gly Ala Cys Ala Gly Ala Cys Thr Gly Gly Gly Gly Ala
1385 1390 1395

Gly Ala Ala Ala Thr Cys Cys Cys Ala Ala Ala Ala Ala Thr Ala
1400 1405 1410

Gly Ala Gly Cys Gly Ala Gly Cys Thr Gly Cys Thr Cys Thr Gly
1415 1420 1425

Gly Ala Cys Gly Gly Ala Thr Cys Thr Gly Ala Cys Cys Gly Ala
1430 1435 1440

Gly Thr Ala Gly Thr Thr Cys Thr Thr Gly Thr Cys Ala Ala Cys
1445 1450 1455

Ala Cys Thr Thr Cys Cys Cys Thr Thr Gly Gly Thr Thr Gly Gly
1460 1465 1470

Cys Cys Ala Ala Ala Cys Gly Gly Cys Thr Thr Ala Gly Cys Cys
1475 1480 1485

Cys Thr Gly Gly Ala Thr Thr Ala Thr Gly Ala Thr Gly Ala Ala
1490 1495 1500

Gly Gly Cys Ala Cys Ala Ala Thr Ala Thr Ala Cys Thr Gly Gly
1505 1510 1515

Gly Gly Ala Gly Ala Thr Gly Cys Cys Ala Ala Ala Ala Cys Ala
1520 1525 1530

Gly Ala Cys Ala Ala Ala Ala Thr Thr Gly Ala Gly Gly Thr Thr
1535 1540 1545

Ala Thr Gly Ala Ala Thr Ala Cys Cys Gly Ala Thr Gly Gly Cys
1550 1555 1560

Ala Cys Cys Gly Gly Gly Ala Gly Gly Cys Gly Ala Gly Thr Gly
1565 1570 1575

Cys Thr Gly Gly Thr Gly Gly Ala Ala Gly Ala Cys Ala Ala Gly
1580 1585 1590

Ala Thr Cys Cys Cys Thr Cys Ala Cys Ala Thr Ala Thr Thr Thr
1595 1600 1605

Gly Gly Gly Thr Thr Thr Ala Cys Cys Thr Thr Gly Cys Thr Gly
1610 1615 1620

Gly Gly Thr Gly Ala Cys Thr Ala Thr Gly Thr Thr Thr Ala Cys
1625 1630 1635

Thr Gly Gly Ala Cys Thr Gly Ala Cys Thr Gly Gly Cys Ala Gly

-continued

```
                1640                1645                1650
Ala Gly Gly Cys Gly Gly Ala Gly Cys Ala Thr Cys Gly Ala Gly
    1655                1660                1665
Ala Gly Ala Gly Thr Ala Cys Ala Cys Ala Ala Ala Cys Gly Gly
    1670                1675                1680
Ala Gly Cys Gly Cys Ala Gly Ala Gly Ala Gly Gly Gly Ala Ala
    1685                1690                1695
Gly Thr Cys Ala Thr Cys Ala Thr Ala Gly Ala Cys Cys Ala Gly
    1700                1705                1710
Cys Thr Gly Cys Cys Ala Gly Ala Cys Cys Thr Cys Ala Thr Gly
    1715                1720                1725
Gly Gly Ala Cys Thr Gly Ala Ala Gly Gly Cys Cys Ala Cys Ala
    1730                1735                1740
Ala Gly Thr Gly Thr Thr Cys Ala Cys Ala Gly Ala Gly Thr Cys
    1745                1750                1755
Ala Thr Thr Gly Gly Thr Thr Cys Thr Ala Ala Cys Cys Cys Cys
    1760                1765                1770
Thr Gly Thr Gly Cys Thr Gly Ala Gly Gly Ala Cys Ala Ala Thr
    1775                1780                1785
Gly Gly Ala Gly Gly Ala Thr Gly Thr Ala Gly Cys Cys Ala Thr
    1790                1795                1800
Cys Thr Thr Thr Gly Cys Cys Thr Gly Thr Ala Cys Ala Gly Gly
    1805                1810                1815
Cys Cys Thr Cys Ala Gly Gly Gly Cys Thr Thr Cys Gly Ala
    1820                1825                1830
Thr Gly Cys Gly Cys Cys Thr Gly Thr Cys Cys Cys Ala Thr Thr
    1835                1840                1845
Gly Gly Cys Thr Thr Thr Gly Ala Gly Cys Thr Cys Ala Thr Cys
    1850                1855                1860
Gly Gly Thr Gly Ala Cys Ala Thr Gly Ala Ala Gly Ala Cys Ala
    1865                1870                1875
Thr Gly Cys Ala Thr Thr Gly Thr Cys Cys Cys Cys Gly Ala Gly
    1880                1885                1890
Gly Cys Thr Thr Thr Cys Cys Thr Thr Cys Thr Gly Thr Thr Cys
    1895                1900                1905
Thr Cys Gly Ala Gly Gly Ala Gly Ala Gly Cys Gly Gly Ala Thr
    1910                1915                1920
Ala Thr Cys Ala Gly Ala Cys Gly Cys Ala Thr Ala Thr Cys Thr
    1925                1930                1935
Thr Thr Gly Gly Ala Ala Ala Cys Ala Ala Ala Cys Ala Ala Cys
    1940                1945                1950
Ala Ala Cys Ala Ala Thr Gly Thr Gly Gly Cys Cys Ala Thr Thr
    1955                1960                1965
Cys Cys Thr Cys Thr Cys Ala Cys Thr Gly Gly Thr Gly Thr Cys
    1970                1975                1980
Ala Ala Ala Gly Ala Ala Gly Cys Cys Thr Cys Thr Gly Cys Thr
    1985                1990                1995
Thr Thr Gly Gly Ala Thr Thr Thr Thr Gly Ala Thr Gly Thr Cys
    2000                2005                2010
Ala Cys Ala Gly Ala Cys Ala Cys Ala Gly Gly Ala Thr Thr
    2015                2020                2025
Thr Ala Cys Thr Gly Gly Ala Cys Thr Gly Ala Thr Ala Thr Ala
    2030                2035                2040
```

Thr Cys Ala Cys Thr Gly Ala Ala Gly Ala Cys Thr Ala Thr Thr
2045 2050 2055

Ala Gly Cys Ala Gly Ala Gly Cys Cys Thr Thr Thr Ala Thr Gly
2060 2065 2070

Ala Ala Thr Gly Gly Cys Ala Gly Thr Gly Cys Ala Cys Thr Gly
2075 2080 2085

Gly Ala Ala Cys Ala Thr Gly Thr Gly Gly Thr Ala Gly Ala Gly
2090 2095 2100

Thr Thr Thr Gly Gly Cys Thr Thr Ala Gly Ala Thr Thr Ala Thr
2105 2110 2115

Cys Cys Ala Gly Ala Ala Gly Gly Cys Ala Thr Gly Gly Cys Ala
2120 2125 2130

Gly Thr Gly Gly Ala Cys Thr Gly Gly Cys Thr Thr Gly Gly Gly
2135 2140 2145

Ala Ala Gly Ala Ala Cys Thr Thr Ala Thr Ala Cys Thr Gly Gly
2150 2155 2160

Gly Cys Ala Gly Ala Cys Ala Cys Ala Gly Gly Ala Ala Cys Ala
2165 2170 2175

Ala Ala Thr Cys Gly Cys Ala Thr Thr Gly Ala Gly Gly Thr Ala
2180 2185 2190

Thr Cys Ala Ala Ala Gly Thr Thr Gly Gly Ala Cys Gly Gly Ala
2195 2200 2205

Cys Ala Gly Cys Ala Cys Cys Gly Ala Cys Ala Gly Gly Thr Thr
2210 2215 2220

Thr Thr Gly Gly Thr Ala Thr Gly Gly Ala Ala Ala Gly Ala Cys
2225 2230 2235

Cys Thr Thr Gly Ala Cys Ala Gly Thr Cys Cys Thr Cys Gly Ala
2240 2245 2250

Gly Cys Thr Cys Thr Gly Gly Cys Ala Cys Thr Gly Gly Ala Thr
2255 2260 2265

Cys Cys Thr Gly Cys Thr Gly Ala Ala Gly Gly Gly Thr Thr Thr
2270 2275 2280

Ala Thr Gly Thr Ala Thr Thr Gly Gly Ala Cys Thr Gly Ala Gly
2285 2290 2295

Thr Gly Gly Gly Gly Ala Gly Gly Cys Ala Ala Gly Cys Cys Thr
2300 2305 2310

Ala Ala Gly Ala Thr Thr Gly Ala Cys Ala Gly Gly Gly Cys Thr
2315 2320 2325

Gly Cys Thr Ala Thr Gly Gly Ala Thr Gly Gly Ala Ala Gly Thr
2330 2335 2340

Gly Ala Ala Cys Gly Cys Ala Cys Thr Ala Cys Ala Thr Thr Ala
2345 2350 2355

Gly Thr Thr Cys Cys Ala Ala Ala Thr Gly Thr Ala Gly Gly Cys
2360 2365 2370

Cys Gly Ala Gly Cys Ala Ala Ala Thr Gly Gly Thr Cys Thr Cys
2375 2380 2385

Ala Cys Cys Ala Thr Cys Gly Ala Cys Thr Ala Thr Gly Cys Thr
2390 2395 2400

Ala Ala Ala Ala Gly Gly Cys Gly Gly Cys Thr Thr Thr Ala Cys
2405 2410 2415

Thr Gly Gly Ala Cys Ala Gly Ala Cys Cys Thr Gly Gly Ala Cys
2420 2425 2430

```
Ala Cys Thr Ala Ala Cys Cys Thr Ala Ala Thr Ala Gly Ala Ala
    2435            2440            2445

Thr Cys Cys Thr Cys Ala Gly Ala Thr Ala Thr Gly Cys Thr Cys
    2450            2455            2460

Gly Gly Ala Cys Thr Cys Ala Ala Cys Cys Gly Thr Gly Ala Ala
    2465            2470            2475

Gly Thr Thr Ala Thr Ala Gly Cys Ala Gly Ala Thr Gly Ala Cys
    2480            2485            2490

Thr Thr Gly Cys Cys Thr Cys Ala Thr Cys Cys Thr Thr Thr Thr
    2495            2500            2505

Gly Gly Cys Thr Thr Ala Ala Cys Thr Cys Ala Gly Thr Ala Cys
    2510            2515            2520

Cys Ala Ala Gly Ala Thr Thr Ala Cys Ala Thr Cys Thr Ala Cys
    2525            2530            2535

Thr Gly Gly Ala Cys Ala Gly Ala Cys Thr Gly Gly Ala Gly Cys
    2540            2545            2550

Cys Gly Ala Cys Gly Cys Ala Gly Cys Ala Thr Thr Gly Ala Ala
    2555            2560            2565

Cys Gly Thr Gly Cys Cys Ala Ala Cys Ala Ala Ala Ala Cys Cys
    2570            2575            2580

Ala Gly Thr Gly Gly Cys Cys Ala Ala Ala Ala Cys Cys Gly Cys
    2585            2590            2595

Ala Cys Cys Ala Thr Cys Ala Thr Cys Cys Ala Gly Gly Gly Cys
    2600            2605            2610

Cys Ala Thr Thr Thr Gly Gly Ala Cys Thr Ala Thr Gly Thr Gly
    2615            2620            2625

Ala Thr Gly Gly Ala Cys Ala Thr Cys Cys Thr Gly Gly Thr Cys
    2630            2635            2640

Thr Thr Cys Cys Ala Cys Thr Cys Thr Thr Cys Cys Cys Gly Gly
    2645            2650            2655

Cys Ala Gly Gly Cys Ala Gly Gly Thr Gly Gly Ala Ala Thr
    2660            2665            2670

Gly Ala Gly Thr Gly Thr Gly Cys Cys Thr Cys Cys Ala Gly Cys
    2675            2680            2685

Ala Ala Cys Gly Gly Gly Cys Ala Cys Thr Gly Cys Thr Cys Cys
    2690            2695            2700

Cys Ala Cys Cys Thr Cys Thr Gly Cys Thr Thr Gly Gly Cys Thr
    2705            2710            2715

Gly Thr Gly Cys Cys Cys Gly Thr Cys Gly Gly Ala Gly Gly Thr
    2720            2725            2730

Thr Thr Thr Gly Thr Gly Thr Gly Thr Gly Gly Ala Thr Gly Cys
    2735            2740            2745

Cys Cys Thr Gly Cys Cys Cys Ala Cys Thr Ala Cys Thr Cys Cys
    2750            2755            2760

Cys Thr Gly Ala Ala Thr Gly Cys Thr Gly Ala Cys Ala Ala Cys
    2765            2770            2775

Ala Gly Gly Ala Cys Cys Thr Gly Cys Ala Gly Thr Gly Cys Thr
    2780            2785            2790

Cys Cys Cys Ala Gly Cys Ala Cys Cys Thr Cys Cys Thr Gly
    2795            2800            2805

Cys Thr Cys Thr Thr Cys Ala Gly Thr Cys Ala Gly Ala Ala Gly
    2810            2815            2820

Ala Gly Cys Gly Cys Cys Ala Thr Cys Ala Ala Cys Cys Gly Cys
```

2825 2830 2835

Ala Thr Gly Gly Thr Gly Ala Thr Thr Gly Ala Thr Gly Ala Ala
2840 2845 2850

Cys Ala Ala Cys Ala Gly Ala Gly Cys Cys Cys Thr Gly Ala Cys
2855 2860 2865

Ala Thr Cys Ala Thr Cys Cys Thr Thr Cys Cys Thr Ala Thr Cys
2870 2875 2880

Cys Ala Cys Ala Gly Cys Cys Thr Thr Cys Gly Gly Ala Ala Cys
2885 2890 2895

Gly Thr Cys Cys Gly Gly Gly Cys Cys Ala Thr Thr Gly Ala Cys
2900 2905 2910

Thr Ala Thr Gly Ala Cys Cys Cys Thr Thr Thr Gly Gly Ala Cys
2915 2920 2925

Ala Ala Gly Cys Ala Gly Cys Thr Cys Thr Ala Cys Thr Gly Gly
2930 2935 2940

Ala Thr Thr Gly Ala Cys Thr Cys Thr Cys Gly Ala Cys Ala Ala
2945 2950 2955

Ala Ala Cys Thr Cys Cys Ala Thr Ala Cys Gly Ala Ala Ala Gly
2960 2965 2970

Gly Cys Ala Cys Ala Thr Gly Ala Ala Gly Ala Thr Gly Gly Thr
2975 2980 2985

Gly Gly Cys Cys Ala Gly Gly Gly Thr Thr Thr Thr Ala Ala Thr
2990 2995 3000

Gly Thr Ala Gly Thr Thr Gly Cys Ala Ala Ala Cys Thr Cys Gly
3005 3010 3015

Gly Thr Cys Gly Cys Ala Ala Ala Thr Cys Ala Gly Ala Ala Cys
3020 3025 3030

Cys Thr Thr Gly Ala Ala Ala Thr Ala Cys Ala Gly Cys Cys Cys
3035 3040 3045

Thr Ala Thr Gly Ala Thr Cys Thr Cys Ala Gly Cys Ala Thr Thr
3050 3055 3060

Gly Ala Thr Ala Thr Thr Thr Ala Thr Ala Gly Cys Cys Gly Thr
3065 3070 3075

Thr Ala Cys Ala Thr Cys Thr Ala Cys Thr Gly Gly Ala Cys Cys
3080 3085 3090

Thr Gly Thr Gly Ala Ala Gly Cys Thr Ala Cys Cys Ala Ala Thr
3095 3100 3105

Gly Thr Cys Ala Thr Thr Gly Ala Thr Gly Thr Gly Ala Cys Gly
3110 3115 3120

Ala Gly Ala Thr Thr Ala Gly Ala Thr Gly Gly Ala Cys Gly Ala
3125 3130 3135

Thr Cys Ala Gly Thr Thr Gly Gly Ala Gly Thr Gly Gly Thr Thr
3140 3145 3150

Cys Thr Ala Ala Ala Ala Gly Gly Cys Gly Ala Gly Cys Ala Ala
3155 3160 3165

Gly Ala Cys Ala Gly Ala Cys Cys Thr Cys Gly Ala Gly Cys Cys
3170 3175 3180

Ala Thr Thr Gly Thr Gly Gly Thr Ala Ala Ala Cys Cys Cys Cys
3185 3190 3195

Gly Ala Gly Ala Ala Ala Gly Gly Gly Thr Ala Thr Ala Thr Gly
3200 3205 3210

Thr Ala Thr Thr Thr Thr Ala Cys Cys Ala Ala Thr Cys Thr Thr
3215 3220 3225

-continued

Cys Ala Gly Gly Ala Ala Ala Gly Ala Thr Cys Thr Cys Cys Thr
3230                3235                    3240

Ala Ala Ala Ala Thr Thr Gly Ala Ala Cys Gly Gly Gly Cys Thr
3245                3250                    3255

Gly Cys Ala Thr Thr Gly Gly Ala Thr Gly Gly Thr Ala Cys Ala
3260                3265                    3270

Gly Ala Ala Cys Gly Ala Gly Ala Gly Gly Thr Cys Cys Thr Cys
3275                3280                    3285

Thr Thr Thr Thr Thr Cys Ala Gly Thr Gly Gly Cys Thr Thr Ala
3290                3295                    3300

Ala Gly Thr Ala Ala Ala Cys Cys Ala Ala Thr Thr Gly Cys Thr
3305                3310                    3315

Thr Thr Gly Gly Cys Thr Cys Thr Thr Gly Ala Thr Ala Gly Cys
3320                3325                    3330

Ala Ala Gly Cys Thr Gly Gly Gly Cys Ala Ala Gly Cys Thr Cys
3335                3340                    3345

Thr Thr Cys Thr Gly Gly Gly Cys Thr Gly Ala Cys Thr Cys Ala
3350                3355                    3360

Gly Ala Thr Cys Thr Cys Cys Gly Gly Cys Gly Ala Ala Thr Thr
3365                3370                    3375

Gly Ala Ala Ala Gly Cys Ala Gly Thr Gly Ala Thr Cys Thr Cys
3380                3385                    3390

Thr Cys Ala Gly Gly Thr Gly Cys Cys Ala Ala Cys Ala Gly Gly
3395                3400                    3405

Ala Thr Cys Gly Thr Gly Cys Thr Ala Gly Ala Ala Gly Ala Cys
3410                3415                    3420

Thr Cys Thr Ala Ala Thr Ala Thr Ala Thr Thr Ala Cys Ala Gly
3425                3430                    3435

Cys Cys Thr Gly Thr Gly Gly Gly Cys Cys Thr Gly Ala Cys Cys
3440                3445                    3450

Gly Thr Gly Thr Thr Thr Gly Ala Ala Ala Ala Cys Thr Gly Gly
3455                3460                    3465

Cys Thr Cys Thr Ala Thr Thr Gly Gly Ala Thr Thr Gly Ala Thr
3470                3475                    3480

Ala Ala Ala Cys Ala Gly Cys Ala Gly Cys Ala Gly Ala Thr Gly
3485                3490                    3495

Ala Thr Thr Gly Ala Ala Ala Ala Ala Thr Thr Gly Ala Cys
3500                3505                    3510

Ala Thr Gly Ala Cys Thr Gly Gly Thr Cys Gly Ala Gly Ala Ala
3515                3520                    3525

Gly Gly Ala Ala Gly Ala Ala Cys Cys Ala Ala Gly Gly Thr Cys
3530                3535                    3540

Cys Ala Gly Gly Cys Thr Cys Gly Ala Ala Thr Thr Gly Cys Thr
3545                3550                    3555

Cys Ala Gly Cys Thr Gly Ala Gly Thr Gly Ala Cys Ala Thr Cys
3560                3565                    3570

Cys Ala Thr Gly Cys Ala Gly Thr Ala Ala Ala Gly Gly Ala Gly
3575                3580                    3585

Cys Thr Gly Ala Ala Cys Cys Thr Thr Cys Ala Gly Gly Ala Gly
3590                3595                    3600

Thr Ala Cys Ala Gly Ala Cys Ala Gly Cys Ala Cys Cys Cys Thr
3605                3610                    3615

-continued

```
Thr Gly  Thr Gly Cys Cys Cys  Ala Gly Gly Ala Thr  Ala Ala Thr
    3620                 3625                 3630

Gly Gly  Thr Gly Gly Cys Thr  Gly Thr Thr Cys Ala  Cys Ala Thr
    3635                 3640                 3645

Ala Thr  Cys Thr Gly Cys Cys  Thr Thr Gly Thr Ala  Ala Ala Ala
    3650                 3655                 3660

Gly Gly  Ala Gly Ala Thr Gly  Gly Thr Ala Cys Gly  Ala Cys Ala
    3665                 3670                 3675

Ala Gly  Ala Thr Gly Cys Thr  Cys Cys Thr Gly Cys  Cys Cys Cys
    3680                 3685                 3690

Ala Thr  Gly Cys Ala Cys Thr  Thr Ala Gly Thr Thr  Cys Thr Gly
    3695                 3700                 3705

Cys Thr  Thr Cys Ala Gly Gly  Ala Thr Gly Ala Gly  Cys Thr Gly
    3710                 3715                 3720

Thr Cys  Cys Thr Gly Thr Gly  Gly Ala Gly Ala Gly  Cys Cys Thr
    3725                 3730                 3735

Cys Cys  Ala Ala Cys Gly Thr  Gly Thr Thr Cys Thr  Cys Cys Thr
    3740                 3745                 3750

Cys Ala  Gly Cys Ala Gly Thr  Thr Thr Ala Cys Cys  Thr Gly Cys
    3755                 3760                 3765

Thr Thr  Cys Ala Cys Thr Gly  Gly Gly Gly Ala Cys  Ala Thr Thr
    3770                 3775                 3780

Gly Ala  Cys Thr Gly Cys Ala  Thr Cys Cys Cys Thr  Gly Thr Gly
    3785                 3790                 3795

Gly Cys  Thr Thr Gly Gly Cys  Gly Gly Thr Gly Thr  Gly Ala Thr
    3800                 3805                 3810

Gly Gly  Gly Thr Thr Cys Ala  Cys Thr Gly Ala Gly  Thr Gly Cys
    3815                 3820                 3825

Gly Ala  Ala Gly Ala Cys Cys  Ala Cys Ala Gly Cys  Gly Ala Thr
    3830                 3835                 3840

Gly Ala  Ala Cys Thr Cys Ala  Ala Thr Thr Gly Thr  Cys Cys Cys
    3845                 3850                 3855

Gly Thr  Gly Thr Gly Cys Thr  Cys Ala Gly Ala Gly  Thr Cys Thr
    3860                 3865                 3870

Cys Ala  Gly Thr Thr Cys Cys  Ala Gly Thr Gly Thr  Gly Cys Cys
    3875                 3880                 3885

Ala Gly  Cys Gly Gly Gly Cys  Ala Gly Thr Gly Cys  Ala Thr Thr
    3890                 3895                 3900

Gly Ala  Thr Gly Gly Thr Gly  Cys Cys Cys Thr Thr  Cys Gly Ala
    3905                 3910                 3915

Thr Gly  Cys Ala Ala Thr Gly  Gly Cys Gly Ala Thr  Gly Cys Gly
    3920                 3925                 3930

Ala Ala  Cys Thr Gly Cys Cys  Ala Gly Gly Ala Cys  Ala Ala Ala
    3935                 3940                 3945

Thr Cys  Ala Gly Ala Thr Gly  Ala Gly Ala Ala Gly  Ala Ala Cys
    3950                 3955                 3960

Thr Gly  Thr Gly Ala Ala Gly  Thr Gly Cys Thr Thr  Thr Gly Thr
    3965                 3970                 3975

Thr Thr  Ala Ala Thr Thr Gly  Ala Thr Cys Ala Gly  Thr Thr Cys
    3980                 3985                 3990

Cys Gly  Cys Thr Gly Thr Gly  Cys Cys Ala Ala Thr  Gly Gly Thr
    3995                 4000                 4005

Cys Ala  Gly Thr Gly Cys Gly  Thr Thr Gly Gly Ala  Ala Ala Gly
```

-continued

```
    4010                4015                4020

Cys Ala  Cys Ala Ala Gly Ala  Ala Ala Thr Gly Thr  Gly Ala Cys
    4025                4030                4035

Cys Ala  Cys Ala Gly Thr Gly  Thr Gly Gly Ala Cys  Thr Gly Cys
    4040                4045                4050

Ala Gly  Thr Gly Ala Cys Ala  Gly Ala Thr Cys Thr  Gly Ala Cys
    4055                4060                4065

Gly Ala  Gly Cys Thr Gly Gly  Ala Cys Thr Gly Thr  Thr Ala Thr
    4070                4075                4080

Cys Cys  Ala Ala Cys Thr Gly  Ala Gly Gly Ala Gly  Cys Cys Ala
    4085                4090                4095

Gly Cys  Ala Cys Cys Ala Cys  Ala Ala Gly Cys Cys  Ala Cys Cys
    4100                4105                4110

Ala Ala  Cys Ala Cys Ala Gly  Thr Thr Gly Gly Thr  Thr Cys Cys
    4115                4120                4125

Gly Thr  Thr Ala Thr Thr Gly  Gly Ala Gly Thr Ala  Ala Thr Thr
    4130                4135                4140

Gly Thr  Cys Ala Cys Cys Ala  Thr Thr Thr Thr Thr  Gly Thr Gly
    4145                4150                4155

Thr Cys  Thr Gly Gly Ala Ala  Cys Cys Ala Thr Ala  Thr Ala Cys
    4160                4165                4170

Thr Thr  Thr Ala Thr Cys Thr  Gly Cys Cys Ala Gly  Ala Gly Gly
    4175                4180                4185

Ala Thr  Gly Cys Thr Gly Thr  Gly Thr Cys Cys Thr  Cys Gly Thr
    4190                4195                4200

Ala Thr  Gly Ala Ala Gly Gly  Gly Ala Gly Ala Cys  Gly Gly Gly
    4205                4210                4215

Gly Ala  Gly Ala Cys Cys Ala  Thr Gly Ala Cys Thr  Ala Ala Cys
    4220                4225                4230

Gly Ala  Cys Thr Ala Thr Gly  Thr Gly Gly Thr Thr  Cys Ala Cys
    4235                4240                4245

Ala Gly  Cys Cys Cys Gly Gly  Cys Gly Thr Cys Thr  Gly Thr Gly
    4250                4255                4260

Cys Cys  Cys Cys Thr Thr Gly  Gly Thr Thr Ala Thr  Gly Thr Thr
    4265                4270                4275

Cys Cys  Thr Cys Ala Cys Cys  Cys Ala Ala Gly Cys  Thr Cys Thr
    4280                4285                4290

Cys Thr  Cys Thr Cys Thr Gly  Gly Ala Thr Cys Thr  Cys Thr Thr
    4295                4300                4305

Cys Cys  Ala Gly Gly Ala Ala  Thr Gly Thr Cys Thr  Cys Gly Ala
    4310                4315                4320

Gly Gly  Cys Ala Ala Ala Thr  Cys Ala Ala Thr Gly  Ala Thr Cys
    4325                4330                4335

Ala Gly  Thr Thr Cys Cys Cys  Thr Cys Ala Gly Thr  Ala Thr Cys
    4340                4345                4350

Ala Thr  Gly Gly Gly Gly Gly  Gly Ala Ala Gly Cys  Ala Gly Thr
    4355                4360                4365

Gly Gly  Gly Cys Cys Cys Cys  Cys Cys Thr Ala Thr  Gly Ala Thr
    4370                4375                4380

Cys Gly  Ala Gly Cys Gly Cys  Ala Cys Gly Thr Cys  Ala Cys Gly
    4385                4390                4395

Gly Gly  Ala Gly Cys Cys Thr  Cys Cys Thr Cys Ala  Ala Gly Cys
    4400                4405                4410
```

-continued

```
Ala Gly  Thr Thr Cys Thr Thr  Cys Cys Ala Gly Thr  Ala Cys Cys
    4415                 4420                 4425

Ala Ala  Ala Gly Gly Cys Ala  Cys Thr Thr Ala Thr  Thr Thr Cys
    4430                 4435                 4440

Cys Cys  Thr Gly Cys Ala Ala  Thr Thr Thr Thr Gly  Ala Ala Cys
    4445                 4450                 4455

Cys Cys  Ala Cys Cys Ala Cys  Cys Ala Thr Cys Cys  Cys Cys Thr
    4460                 4465                 4470

Gly Cys  Cys Ala Cys Ala Gly  Ala Ala Ala Gly Ala  Thr Cys Cys
    4475                 4480                 4485

Cys Ala  Thr Thr Ala Thr Ala  Cys Cys Ala Thr Gly  Gly Ala Ala
    4490                 4495                 4500

Thr Thr  Thr Gly Gly Thr Thr  Ala Thr Thr Cys Thr  Thr Cys Cys
    4505                 4510                 4515

Ala Ala  Cys Ala Gly Thr Cys  Cys Thr Thr Cys Cys  Ala Cys Ala
    4520                 4525                 4530

Cys Ala  Thr Ala Gly Gly Thr  Cys Cys Thr Ala Cys  Ala Gly Cys
    4535                 4540                 4545

Thr Ala  Thr Ala Gly Gly Cys  Cys Gly Thr Ala Cys  Ala Gly Cys
    4550                 4555                 4560

Thr Ala  Cys Cys Gly Gly Cys  Ala Cys Thr Thr Thr  Gly Cys Ala
    4565                 4570                 4575

Cys Cys  Gly Cys Cys Cys Ala  Cys Cys Ala Cys Ala  Cys Cys Cys
    4580                 4585                 4590

Thr Gly  Cys Ala Gly Cys Ala  Cys Thr Gly Ala Thr  Gly Thr Cys
    4595                 4600                 4605

Thr Gly  Thr Gly Ala Cys Ala  Gly Thr Gly Ala Cys  Thr Ala Thr
    4610                 4615                 4620

Gly Cys  Thr Cys Cys Thr Ala  Gly Cys Cys Gly Gly  Ala Gly Gly
    4625                 4630                 4635

Ala Thr  Gly Ala Cys Cys Thr  Cys Gly Gly Thr Gly  Gly Cys Ala
    4640                 4645                 4650

Ala Cys  Ala Gly Cys Cys Ala  Ala Gly Gly Gly Cys  Thr Ala Cys
    4655                 4660                 4665

Ala Cys  Cys Ala Gly Thr Gly  Ala Cys Gly Thr Gly  Ala Ala Cys
    4670                 4675                 4680

Thr Ala  Thr Gly Ala Cys Thr  Cys Ala Gly Ala Ala  Cys Cys Thr
    4685                 4690                 4695

Gly Thr  Gly Cys Cys Cys Cys  Cys Ala Cys Cys Gly  Cys Cys Cys
    4700                 4705                 4710

Ala Cys  Ala Cys Cys Cys Cys  Gly Ala Ala Gly Cys  Cys Ala Gly
    4715                 4720                 4725

Thr Ala  Cys Thr Thr Gly Thr  Cys Ala Gly Cys Gly  Gly Ala Gly
    4730                 4735                 4740

Gly Ala  Gly Ala Ala Cys Thr  Ala Thr Gly Ala Ala  Ala Gly Cys
    4745                 4750                 4755

Thr Gly  Cys Cys Cys Cys Cys  Cys Thr Thr Cys Cys  Cys Cys Ala
    4760                 4765                 4770

Thr Ala  Cys Ala Cys Gly Gly  Ala Gly Ala Gly Gly  Ala Gly Thr
    4775                 4780                 4785

Thr Ala  Cys Thr Cys Cys Cys  Ala Cys Cys Ala Cys  Cys Thr Cys
    4790                 4795                 4800
```

```
Thr Ala  Cys Cys Cys Gly Cys  Cys Ala Cys Cys Ala  Cys Cys Cys
    4805             4810              4815

Thr Cys  Cys Cys Cys Cys Thr  Gly Cys Ala Cys Gly  Gly Ala Cys
    4820             4825              4830

Thr Cys  Cys Thr Cys Cys Thr  Gly Ala
    4835             4840

<210> SEQ ID NO 9
<211> LENGTH: 4842
<212> TYPE: DNA
<213> ORGANISM: Mouse

<400> SEQUENCE: 9
```

| | | | | | |
|---|---|---|---|---|---|
| atgggggccg | tgctgaggag | cctcctggcc | tgcagcttct | gcgtgctgct | gagagcggcc | 60 |
| cctttgttgc | tttatgcaaa | cagacgggac | ttgagattgg | ttgatgctac | aaatggcaaa | 120 |
| gagaatgcaa | cgattgtagt | tggaggcttg | gaggatgcag | ctgcggtgga | ctttgtgttt | 180 |
| ggtcatggct | tgatatactg | gagtgatgtc | agcgaagaag | ccattaaacg | aacagaattt | 240 |
| aacaaaagtg | aaagtgtaca | gaatgttgtt | gtttctggat | tattgtcccc | ggatgggctg | 300 |
| gcatgtgatt | ggcttggaga | aaaattgtac | tggacagatt | ctgaaactaa | tcgtattgaa | 360 |
| gtttctaatt | tagatggatc | tttacgaaaa | gttttatttt | ggcaagagtt | ggatcaaccc | 420 |
| agagctattg | cctagatcc | atcaagtggg | ttcatgtact | ggacagactg | gggagaagtg | 480 |
| ccaaagatag | aacgggctgg | gatggatggc | tcaagtcgct | tcgttataat | aaacacggag | 540 |
| atttactggc | caaacggact | gactctggat | tatcaggagc | ggaagcttta | ctgggccgat | 600 |
| gcaaaactta | atttcatcca | taaatcaaac | ctggatggaa | caaaccggca | ggcagtggtt | 660 |
| aaaggttccc | ttccacatcc | ttttgccttg | acgttatttg | aggacacatt | gtactggact | 720 |
| gactggaata | cacactctat | tttggcttgc | aacaaatata | ctggcgaggg | tctgcgtgaa | 780 |
| attcattcta | acatcttctc | tcccatggat | atacatgctt | tcagccaaca | gaggcagcca | 840 |
| aatgctacaa | atccatgtgg | aattgataat | ggtggttgtt | cccatttgtg | tttgatgtct | 900 |
| ccagtcaagc | cttttatca | gtgtgcttgc | ccaactgggg | tcaagctgat | ggagaatgga | 960 |
| aagacctgca | aagatggtgc | cactgaacta | ttgctgttag | cccgacggac | agacttgagg | 1020 |
| cgaatttctt | tggatacacc | cgattttact | gacattgttc | tgcagttaga | agatatccgg | 1080 |
| catgccattg | cctagacta | tgaccctgta | gaaggctaca | tactggacag | atgacgaa | 1140 |
| gtgagggcta | tccgtcgctc | cttcatagat | ggatctggca | gtcagtttgt | ggtcacggcc | 1200 |
| cagattgctc | atcctgatgg | tattgctgtt | gactgggttg | caaggaacct | gtactggaca | 1260 |
| gacactggca | cggatcgtat | agaagtgaca | aggctcaatg | ggaccatgag | gaagatcttg | 1320 |
| atttcagagg | acttagagga | gcccccgggct | atcgtgttag | atcccatggt | tgggtacatg | 1380 |
| tattggacag | actggggaga | aatcccaaaa | atagagcgag | ctgctctgga | cggatctgac | 1440 |
| cgagtagttc | ttgtcaacac | ttcccttggt | tggccaaacg | gcttagccct | ggattatgat | 1500 |
| gaaggcacaa | tatactgggg | agatgccaaa | acagacaaaa | ttgaggttat | gaataccgat | 1560 |
| ggcaccggga | ggcgagtgct | ggtggaagac | aagatccctc | acatatttgg | gtttaccttg | 1620 |
| ctgggtgact | atgtttactg | gactgactgg | cagaggcgga | gcatcgagag | agtacacaaa | 1680 |
| cggagcgcag | agagggaagt | catcatagac | cagctgccag | acctcatggg | actgaaggcc | 1740 |
| acaagtgttc | acagagtcat | tggttctaac | ccctgtgctg | aggacaatgg | aggatgtagc | 1800 |
| catctttgcc | tgtacaggcc | tcaggggctt | cgatgcgcct | gtcccattgg | ctttgagctc | 1860 |

```
atcggtgaca tgaagacatg cattgtcccc gaggctttcc ttctgttctc gaggagagcg   1920
gatatcagac gcatatcttt ggaaacaaac aacaacaatg tggccattcc tctcactggt   1980
gtcaaagaag cctctgcttt ggattttgat gtcacagaca acaggattta ctggactgat   2040
atatcactga agactattag cagagccttt atgaatggca gtgcactgga acatgtggta   2100
gagtttggct tagattatcc agaaggcatg gcagtggact ggcttgggaa gaacttatac   2160
tgggcagaca caggaacaaa tcgcattgag gtatcaaagt tggacggaca gcaccgacag   2220
gttttggtat ggaaagacct tgacagtcct cgagctctgg cactggatcc tgctgaaggg   2280
tttatgtatt ggactgagtg gggaggcaag cctaagattg acagggctgc tatggatgga   2340
agtgaacgca ctacattagt tccaaatgta ggccgagcaa atggtctcac catcgactat   2400
gctaaaaggc ggctttactg gacagacctg gacactaacc taatagaatc ctcagatatg   2460
ctcggactca accgtgaagt tatagcagat gacttgcctc atccttttgg cttaactcag   2520
taccaagatt acatctactg gacagactgg agccgacgca gcattgaacg tgccaacaaa   2580
accagtggcc aaaaccgcac catcatccag ggccatttgg actatgtgat ggacatcctg   2640
gtcttccact cttcccggca ggcagggtgg aatgagtgtg cctccagcaa cgggcactgc   2700
tcccacctct gcttggctgt gcccgtcgga ggttttgtgt gtggatgccc tgcccactac   2760
tccctgaatg ctgacaacag gacctgcagt gctcccagca ccttcctgct cttcagtcag   2820
aagagcgcca tcaaccgcat ggtgattgat gaacaacaga gccctgacat catccttcct   2880
atccacagcc ttcggaacgt ccgggccatt gactatgacc ctttggacaa gcagctctac   2940
tggattgact ctcgacaaaa ctccatacga aaggcacatg aagatggtgg ccagggtttt   3000
aatgtagttg caaactcggt cgcaaatcag aaccttgaaa tacagcccta tgatctcagc   3060
attgatattt atagccgtta catctactgg acctgtgaag ctaccaatgt cattgatgtg   3120
acgagattag atggacgatc agttggagtg gttctaaaag gcgagcaaga cagacctcga   3180
gccattgtgg taaccccga gaagggtat atgtatttta ccaatcttca ggaaagatct   3240
cctaaaattg aacgggctgc attggatggt acagaacgag aggtcctctt tttcagtggc   3300
ttaagtaaac caattgcttt ggctcttgat agcaagctgg gcaagctctt ctgggctgac   3360
tcagatctcc ggcgaattga aagcagtgat ctctcaggtg ccaacaggat cgtgctagaa   3420
gactctaata tattacagcc tgtgggcctg accgtgtttg aaaactggct ctattggatt   3480
gataaacagc agcagatgat tgaaaaaatt gacatgactg gtcgagaagg aagaaccaag   3540
gtccaggctc gaattgctca gctgagtgac atccatgcag taaaggagct gaaccttcag   3600
gagtacagac agcacccttg tgcccaggat aatggtggct gttcacatat ctgccttgta   3660
aaaggagatg gtacgacaag atgctcctgc cccatgcact agttctgct tcaggatgag   3720 ctgtcctgtg gagagcctcc aacgtgttct cctcagcagt ttacctgctt cactggggac   3780
attgactgca tccctgtggc ttggcggtgt gatgggttca ctgagtgcga agaccacagc   3840
gatgaactca attgtcccgt gtgctcagag tctcagttcc agtgtgccag cgggcagtgc   3900
attgatggtg cccttcgatg caatggcgat gcgaactgcc aggacaaatc agatgagaag   3960
aactgtgaag tgctttgttt aattgatcag ttccgctgtg ccaatggtca gtgcgttgga   4020
aagcacaaga atgtgaccca gtgtggac tgcagtgaca gatctgacga gctggactgt   4080
tatccaactg aggagccagc accacaagcc accaacacag ttggttccgt tattggagta   4140
attgtcacca ttttgtgtc tggaaccata tactttatct gccagaggat gctgtgtcct   4200
cgtatgaagg gagacgggga gaccatgact aacgactatg tggttcacag cccggcgtct   4260
```

-continued

```
gtgcccctt gttatgttcc tcacccaagc tctctctctg gatctcttcc aggaatgtct      4320
cgaggcaaat caatgatcag ttccctcagt atcatggggg gaagcagtgg gccccctat      4380 gatcgagcgc acgtcacggg agcctcctca agcagttctt ccagtaccaa aggcacttat      4440
ttccctgcaa ttttgaaccc accaccatcc cctgccacag aaagatccca ttataccatg      4500
gaatttggtt attcttccaa cagtccttcc acacataggt cctacagcta taggccgtac      4560
agctaccggc actttgcacc gcccaccaca ccctgcagca ctgatgtctg tgacagtgac      4620
tatgctccta gccggaggat gacctcggtg gcaacagcca agggctacac cagtgacgtg      4680
aactatgact cagaacctgt gcccccaccg cccacacccc gaagccagta cttgtcagcg      4740
gaggagaact atgaaagctg ccccccttcc ccatacacgg agaggagtta ctcccaccac      4800
ctctacccgc caccaccctc cccctgcacg gactcctcct ga                        4842
```

<210> SEQ ID NO 10
<211> LENGTH: 1613
<212> TYPE: PRT
<213> ORGANISM: Mouse

<400> SEQUENCE: 10

```
Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
            20                  25                  30

Leu Val Asp Ala Thr Asn Gly Lys Glu Asn Ala Thr Ile Val Val Gly
        35                  40                  45

Gly Leu Glu Asp Ala Ala Ala Val Asp Phe Val Phe Gly His Gly Leu
    50                  55                  60

Ile Tyr Trp Ser Asp Val Ser Glu Glu Ala Ile Lys Arg Thr Glu Phe
65                  70                  75                  80

Asn Lys Ser Glu Ser Val Gln Asn Val Val Ser Gly Leu Leu Ser
            85                  90                  95

Pro Asp Gly Leu Ala Cys Asp Trp Leu Gly Glu Lys Leu Tyr Trp Thr
            100                 105                 110

Asp Ser Glu Thr Asn Arg Ile Glu Val Ser Asn Leu Asp Gly Ser Leu
            115                 120                 125

Arg Lys Val Leu Phe Trp Gln Glu Leu Asp Gln Pro Arg Ala Ile Ala
        130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Val Ile
            165                 170                 175

Ile Asn Thr Glu Ile Tyr Trp Pro Asn Gly Leu Thr Leu Asp Tyr Gln
            180                 185                 190

Glu Arg Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
    210                 215                 220

Pro His Pro Phe Ala Leu Thr Leu Phe Glu Asp Thr Leu Tyr Trp Thr
225                 230                 235                 240

Asp Trp Asn Thr His Ser Ile Leu Ala Cys Asn Lys Tyr Thr Gly Glu
            245                 250                 255

Gly Leu Arg Glu Ile His Ser Asn Ile Phe Ser Pro Met Asp Ile His
            260                 265                 270
```

```
Ala Phe Ser Gln Gln Arg Gln Pro Asn Ala Thr Asn Pro Cys Gly Ile
            275                 280                 285

Asp Asn Gly Gly Cys Ser His Leu Cys Leu Met Ser Pro Val Lys Pro
    290                 295                 300

Phe Tyr Gln Cys Ala Cys Pro Thr Gly Val Lys Leu Met Glu Asn Gly
305                 310                 315                 320

Lys Thr Cys Lys Asp Gly Ala Thr Glu Leu Leu Leu Ala Arg Arg
                325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
            355                 360                 365

Pro Val Glu Gly Tyr Ile Tyr Trp Thr Asp Asp Glu Val Arg Ala Ile
    370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
            420                 425                 430

Asn Gly Thr Met Arg Lys Ile Leu Ile Ser Glu Asp Leu Glu Glu Pro
            435                 440                 445

Arg Ala Ile Val Leu Asp Pro Met Val Gly Tyr Met Tyr Trp Thr Asp
    450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Thr Ile Tyr Trp Gly Asp Ala Lys Thr Asp
            500                 505                 510

Lys Ile Glu Val Met Asn Thr Asp Gly Thr Gly Arg Arg Val Leu Val
            515                 520                 525

Glu Asp Lys Ile Pro His Ile Phe Gly Phe Thr Leu Leu Gly Asp Tyr
    530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Ser Val His Arg Val Ile Gly Ser Asn Pro Cys
            580                 585                 590

Ala Glu Asp Asn Gly Gly Cys Ser His Leu Cys Leu Tyr Arg Pro Gln
            595                 600                 605

Gly Leu Arg Cys Ala Cys Pro Ile Gly Phe Glu Leu Ile Gly Asp Met
    610                 615                 620

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Asn Val Ala Ile
                645                 650                 655

Pro Leu Thr Gly Val Lys Glu Ala Ser Ala Leu Asp Phe Asp Val Thr
            660                 665                 670

Asp Asn Arg Ile Tyr Trp Thr Asp Ile Ser Leu Lys Thr Ile Ser Arg
            675                 680                 685
```

-continued

```
Ala Phe Met Asn Gly Ser Ala Leu Glu His Val Val Glu Phe Gly Leu
    690                 695                 700
Asp Tyr Pro Glu Gly Met Ala Val Asp Trp Leu Gly Lys Asn Leu Tyr
705                 710                 715                 720
Trp Ala Asp Thr Gly Thr Asn Arg Ile Glu Val Ser Lys Leu Asp Gly
                725                 730                 735
Gln His Arg Gln Val Leu Val Trp Lys Asp Leu Asp Ser Pro Arg Ala
            740                 745                 750
Leu Ala Leu Asp Pro Ala Glu Gly Phe Met Tyr Trp Thr Glu Trp Gly
        755                 760                 765
Gly Lys Pro Lys Ile Asp Arg Ala Ala Met Asp Gly Ser Glu Arg Thr
770                 775                 780
Thr Leu Val Pro Asn Val Gly Arg Ala Asn Gly Leu Thr Ile Asp Tyr
785                 790                 795                 800
Ala Lys Arg Arg Leu Tyr Trp Thr Asp Leu Asp Thr Asn Leu Ile Glu
                805                 810                 815
Ser Ser Asp Met Leu Gly Leu Asn Arg Glu Val Ile Ala Asp Asp Leu
            820                 825                 830
Pro His Pro Phe Gly Leu Thr Gln Tyr Gln Asp Tyr Ile Tyr Trp Thr
        835                 840                 845
Asp Trp Ser Arg Arg Ser Ile Glu Arg Ala Asn Lys Thr Ser Gly Gln
850                 855                 860
Asn Arg Thr Ile Ile Gln Gly His Leu Asp Tyr Val Met Asp Ile Leu
865                 870                 875                 880
Val Phe His Ser Ser Arg Gln Ala Gly Trp Asn Glu Cys Ala Ser Ser
                885                 890                 895
Asn Gly His Cys Ser His Leu Cys Leu Ala Val Pro Val Gly Gly Phe
            900                 905                 910
Val Cys Gly Cys Pro Ala His Tyr Ser Leu Asn Ala Asp Asn Arg Thr
        915                 920                 925
Cys Ser Ala Pro Ser Thr Phe Leu Leu Phe Ser Gln Lys Ser Ala Ile
930                 935                 940
Asn Arg Met Val Ile Asp Glu Gln Gln Ser Pro Asp Ile Ile Leu Pro
945                 950                 955                 960
Ile His Ser Leu Arg Asn Val Arg Ala Ile Asp Tyr Asp Pro Leu Asp
                965                 970                 975
Lys Gln Leu Tyr Trp Ile Asp Ser Arg Gln Asn Ser Ile Arg Lys Ala
            980                 985                 990
His Glu Asp Gly Gly Gln Gly Phe Asn Val Val Ala Asn Ser Val Ala
        995                 1000                1005
Asn Gln Asn Leu Glu Ile Gln Pro Tyr Asp Leu Ser Ile Asp Ile
    1010                1015                1020
Tyr Ser Arg Tyr Ile Tyr Trp Thr Cys Glu Ala Thr Asn Val Ile
    1025                1030                1035
Asp Val Thr Arg Leu Asp Gly Arg Ser Val Gly Val Val Leu Lys
    1040                1045                1050
Gly Glu Gln Asp Arg Pro Arg Ala Ile Val Val Asn Pro Glu Lys
    1055                1060                1065
Gly Tyr Met Tyr Phe Thr Asn Leu Gln Glu Arg Ser Pro Lys Ile
    1070                1075                1080
Glu Arg Ala Ala Leu Asp Gly Thr Glu Arg Glu Val Leu Phe Phe
    1085                1090                1095
Ser Gly Leu Ser Lys Pro Ile Ala Leu Ala Leu Asp Ser Lys Leu
```

```
                    1100              1105              1110
Gly Lys Leu Phe Trp Ala Asp Ser Asp Leu Arg Arg Ile Glu Ser
        1115              1120              1125

Ser Asp Leu Ser Gly Ala Asn Arg Ile Val Leu Glu Asp Ser Asn
        1130              1135              1140

Ile Leu Gln Pro Val Gly Leu Thr Val Phe Glu Asn Trp Leu Tyr
        1145              1150              1155

Trp Ile Asp Lys Gln Gln Gln Met Ile Glu Lys Ile Asp Met Thr
        1160              1165              1170

Gly Arg Glu Gly Arg Thr Lys Val Gln Ala Arg Ile Ala Gln Leu
        1175              1180              1185

Ser Asp Ile His Ala Val Lys Glu Leu Asn Leu Gln Glu Tyr Arg
        1190              1195              1200

Gln His Pro Cys Ala Gln Asp Asn Gly Gly Cys Ser His Ile Cys
        1205              1210              1215

Leu Val Lys Gly Asp Gly Thr Thr Arg Cys Ser Cys Pro Met His
        1220              1225              1230

Leu Val Leu Leu Gln Asp Glu Leu Ser Cys Gly Glu Pro Pro Thr
        1235              1240              1245

Cys Ser Pro Gln Gln Phe Thr Cys Phe Thr Gly Asp Ile Asp Cys
        1250              1255              1260

Ile Pro Val Ala Trp Arg Cys Asp Gly Phe Thr Glu Cys Glu Asp
        1265              1270              1275

His Ser Asp Glu Leu Asn Cys Pro Val Cys Ser Glu Ser Gln Phe
        1280              1285              1290

Gln Cys Ala Ser Gly Gln Cys Ile Asp Gly Ala Leu Arg Cys Asn
        1295              1300              1305

Gly Asp Ala Asn Cys Gln Asp Lys Ser Asp Glu Lys Asn Cys Glu
        1310              1315              1320

Val Leu Cys Leu Ile Asp Gln Phe Arg Cys Ala Asn Gly Gln Cys
        1325              1330              1335

Val Gly Lys His Lys Lys Cys Asp His Ser Val Asp Cys Ser Asp
        1340              1345              1350

Arg Ser Asp Glu Leu Asp Cys Tyr Pro Thr Glu Glu Pro Ala Pro
        1355              1360              1365

Gln Ala Thr Asn Thr Val Gly Ser Val Ile Gly Val Ile Val Thr
        1370              1375              1380

Ile Phe Val Ser Gly Thr Ile Tyr Phe Ile Cys Gln Arg Met Leu
        1385              1390              1395

Cys Pro Arg Met Lys Gly Asp Gly Glu Thr Met Thr Asn Asp Tyr
        1400              1405              1410

Val Val His Ser Pro Ala Ser Val Pro Leu Gly Tyr Val Pro His
        1415              1420              1425

Pro Ser Ser Leu Ser Gly Ser Leu Pro Gly Met Ser Arg Gly Lys
        1430              1435              1440

Ser Met Ile Ser Ser Leu Ser Ile Met Gly Gly Ser Ser Gly Pro
        1445              1450              1455

Pro Tyr Asp Arg Ala His Val Thr Gly Ala Ser Ser Ser Ser Ser
        1460              1465              1470

Ser Ser Thr Lys Gly Thr Tyr Phe Pro Ala Ile Leu Asn Pro Pro
        1475              1480              1485

Pro Ser Pro Ala Thr Glu Arg Ser His Tyr Thr Met Glu Phe Gly
        1490              1495              1500
```

```
Tyr Ser Ser Asn Ser Pro Ser Thr His Arg Ser Tyr Ser Tyr Arg
            1505                1510                1515

Pro Tyr Ser Tyr Arg His Phe Ala Pro Thr Thr Pro Cys Ser
    1520                1525                1530

Thr Asp Val Cys Asp Ser Asp Tyr Ala Pro Ser Arg Arg Met Thr
    1535                1540                1545

Ser Val Ala Thr Ala Lys Gly Tyr Thr Ser Asp Val Asn Tyr Asp
    1550                1555                1560

Ser Glu Pro Val Pro Pro Pro Thr Pro Arg Ser Gln Tyr Leu
    1565                1570                1575

Ser Ala Glu Glu Asn Tyr Glu Ser Cys Pro Pro Ser Pro Tyr Thr
    1580                1585                1590

Glu Arg Ser Tyr Ser His His Leu Tyr Pro Pro Pro Ser Pro
    1595                1600                1605

Cys Thr Asp Ser Ser
    1610

<210> SEQ ID NO 11
<211> LENGTH: 4161
<212> TYPE: DNA
<213> ORGANISM: Mouse

<400> SEQUENCE: 11
atggaaacgg cgccgacccg ggcccctccg ccgccgccgc cgccgctgct gctgctggtg      60
ctgtactgca gcttggtccc cgccgcggcc tcaccgctcc tgttgtttgc caaccgccgg     120
gatgtgcggc tagtggatgc cggcggagtg aagctggagt ccaccattgt ggccagtggc     180
ctggaggatg cagctgctgt agacttccag ttctccaagg gtgctgtgta ctggacagat     240
gtgagcgagg aggccatcaa acagacctac ctgaaccaga ctggagctgc tgcacagaac     300
attgtcatct cgggcctcgt gtcacctgat ggcctggcct gtgactgggt ggcaagaag      360 ctgtactgga cggactccga gaccaaccgc attgaggttg ccaacctcaa tgggacgtcc     420
cgtaaggttc tcttctggca ggacctggac cagccaaggg ccattgccct ggatcctgca     480
catgggtaca tgtactggac tgactggggg gaagcacccc ggatcgagcg ggcagggatg     540
gatggcagta cccggaagat cattgtagac tccgacattt actggccaa tgggctgacc     600 atcgacctgg aggaacagaa gctgtactgg gccgatgcca gctcagctt catccaccgt     660 gccaacctgg acggctcctt ccggcagaag gtggtggagg cagcctcac tcacccttt      720 gccctgacac tctctgggga cacactctac tggacagact ggcagacccg ctccatccac     780
gcctgcaaca gtggacaggg gagcagagg aaggagatcc ttagtgctct gtactcaccc     840
atggacatcc aagtgctgag ccaggagcgg cagcctccct ccacacacc atgcgaggag     900 gacaacggtg gctgttccca cctgtgcctg ctgtccccga gggagccttt ctactcctgt     960
gcctgcccca ctggtgtgca gttgcaggac aatggcaaga cgtgcaagac aggggctgag    1020
gaagtgctgc tgctggctcg gaggacagac ctgaggagga tctctctgga cacccctgac    1080
ttcacagaca tagtgctgca ggtgggcgac atccggcatg ccattgccat tgactacgat    1140
cccctggagg gctacgtgta ctggaccgat gatgaggtgc gggctatccg cagggcgtac    1200
ctagatggct caggtgcgca gacacttgtg aacactgaga tcaatgaccc cgatggcatt    1260
gctgtggact gggtcgcccg gaacctctac tggacagata caggcactga cagaattgag    1320
gtgactcgcc tcaacggcac ctcccgaaag atcctggtat ctgaggacct ggacgaaccg    1380
```

```
cgagccattg tgttgcaccc tgtgatgggc ctcatgtact ggacagactg gggggagaac    1440
cccaaaatcg aatgcgccaa cctagatggg agagatcggc atgtcctggt gaacacctcc    1500
cttgggtggc ccaatggact ggccctggac ctgcaggagg gcaagctgta ctgggggat     1560 gccaaaactg ataaaatcga ggtgatcaac atagacggga caaagcggaa gaccctgctt    1620
gaggacaagc tcccacacat ttttgggttc acactgctgg gggacttcat ctactggacc    1680
gactggcaga gacgcagtat tgaaagggtc acaaggtca aggccagccg ggatgtcatc     1740
attgatcaac tccccgacct gatgggactc aaagccgtga atgtggccaa ggttgtcgga    1800
accaacccat gtgcggatgg aaatggaggg tgcagccatc tgtgcttctt cacccacgt     1860 gccaccaagt gtggctgccc cattggcctg gagctgttga gtgacatgaa gacctgcata    1920
atccccgagg ccttcctggt attcaccagc agagccacca tccacaggat ctccctggag    1980
actaacaaca acgatgtggc tatcccactc acgggtgtca agaggcctc tgcactggac     2040 tttgatgtgt ccaacaatca catctactgg actgatgtta gcctcaagac gatcagccga    2100
gccttcatga atgggagctc agtggagcac gtgattgagt ttggcctcga ctaccctgaa    2160
ggaatggctg tggactggat gggcaagaac ctctattggg cggacacagg accaacagg    2220 attgaggtgg cccggctgga tgggcagttc cggcaggtgc ttgtgtggag gaccttgac     2280 aaccccaggt ctctggctct ggatcctact aaaggctaca tctactggac tgagtggggt    2340
ggcaagccaa ggattgtgcg ggccttcatg gatgggacca attgtatgac actggtagac    2400
aaggtgggcc gggccaacga cctcaccatt gattatgccg accagcgact gtactggact    2460
gacctggaca ccaacatgat tgagtcttcc aacatgctgg gtcaggagcg catggtgata    2520
gctgacgatc tgccctaccc gtttggcctg actcaatata gcgattacat ctactggact    2580
gactggaacc tgcatagcat tgaacgggcg gacaagacca gtgggcggaa ccgcacccctc    2640 atccagggtc acctggactt cgtcatggac atcctggtgt tccactcctc ccgtcaggat    2700
ggcctcaacg actgcgtgca cagcaatggc cagtgtgggc agctgtgcct cgccatcccc    2760
ggaggccacc gctgtggctg tgcttcacac tacacgctgg accccagcag ccgcaactgc    2820
agcccgccct ccaccttctt gctgttcagc cagaaatttg ccatcagccg gatgatcccc    2880
gatgaccagc tcagcccgga ccttgtccta ccccttcatg ggctgaggaa cgtcaaagcc    2940
atcaactatg acccgctgga caagttcatc tactgggtgg acgggcgcca gaacatcaag    3000
agggccaagg acgacggtac ccagccctcc atgctgacct ctcccagcca aagcctgagc    3060
ccagacagac agccacacga cctcagcatt gacatctaca gccggacact gttctggacc    3120
tgtgaggcca ccaacactat caatgtccac cggctggatg gggatgccat gggagtggtg    3180
cttcgagggg accgtgacaa gccaagggcc attgctgtca atgctgagcg agggtacatg    3240
tactttacca acatgcagga ccatgctgcc aagatcgagc gagcctccct ggatggcaca    3300
gagcgggagg tcctcttcac cacaggcctc atccgtcccg tggcccttgt ggtggacaat    3360
gctctgggca agctcttctg ggtggatgcc gacctaaagc gaatcgaaag ctgtgacctc    3420
tctggggcca accgcctgac cctggaagat gccaacatcg tacagccagt aggtctgaca    3480 gtgctggca ggcacctcta ctggatcgac cgccagcagc agatgatcga gcgcgtggag    3540
aagaccactg ggacaagcg gactagggtt cagggccgtg tcacccacct gacaggcatc    3600
catgccgtgg aggaagtcag cctggaggag ttctcagccc atccttgtgc ccgagacaat    3660
ggcggctgct cccacatctg tatcgccaag ggtgatggaa caccgcgctg ctcgtgcccc    3720
gtccacctgg tgctcctgca gaacctgctg acttgtggtg agcctcctac ctgctcccct    3780
```

```
gatcagtttg catgtaccac tggtgagatc gactgcatcc ccggagcctg gcgctgtgac    3840
ggcttccctg agtgtgctga ccagagtgat gaagaaggct gcccagtgtg ctccgcctct    3900
cagttcccct gcgctcgagg ccagtgtgtg gacctgcggt tacgctgcga cggtgaggcc    3960
gactgccagg atcgctctga tgaagctaac tgcgatgctg tctgtctgcc caatcagttc    4020
cggtgcacca gcggccagtg tgtcctcatc aagcaacagt gtgactcctt ccccgactgt    4080
gctgatgggt ctgatgagct catgtgtgaa atcaacaagc caccctctga tgacatccca    4140
gcccacagca gtgccattgg g                                              4161
```

<210> SEQ ID NO 12
<211> LENGTH: 1384
<212> TYPE: PRT
<213> ORGANISM: Mouse

<400> SEQUENCE: 12

Met Glu Thr Ala Pro Thr Arg Ala Pro Pro Pro Pro Pro Pro Leu
1               5                   10                  15

Leu Leu Leu Val Leu Tyr Cys Ser Leu Val Pro Ala Ala Ala Ser Pro
            20                  25                  30

Leu Leu Leu Phe Ala Asn Arg Arg Asp Val Arg Leu Val Asp Ala Gly
            35                  40                  45

Gly Val Lys Leu Glu Ser Thr Ile Val Ala Ser Gly Leu Glu Asp Ala
50                  55                  60

Ala Ala Val Asp Phe Gln Phe Ser Lys Gly Ala Val Tyr Trp Thr Asp
65                  70                  75                  80

Val Ser Glu Glu Ala Ile Lys Gln Thr Tyr Leu Asn Gln Thr Gly Ala
                85                  90                  95

Ala Ala Gln Asn Ile Val Ile Ser Gly Leu Val Ser Pro Asp Gly Leu
            100                 105                 110

Ala Cys Asp Trp Val Gly Lys Lys Leu Tyr Trp Thr Asp Ser Glu Thr
            115                 120                 125

Asn Arg Ile Glu Val Ala Asn Leu Asn Gly Thr Ser Arg Lys Val Leu
            130                 135                 140

Phe Trp Gln Asp Leu Asp Gln Pro Arg Ala Ile Ala Leu Asp Pro Ala
145                 150                 155                 160

His Gly Tyr Met Tyr Trp Thr Asp Trp Gly Glu Ala Pro Arg Ile Glu
                165                 170                 175

Arg Ala Gly Met Asp Gly Ser Thr Arg Lys Ile Ile Val Asp Ser Asp
            180                 185                 190

Ile Tyr Trp Pro Asn Gly Leu Thr Ile Asp Leu Glu Glu Gln Lys Leu
            195                 200                 205

Tyr Trp Ala Asp Ala Lys Leu Ser Phe Ile His Arg Ala Asn Leu Asp
            210                 215                 220

Gly Ser Phe Arg Gln Lys Val Val Glu Gly Ser Leu Thr His Pro Phe
225                 230                 235                 240

Ala Leu Thr Leu Ser Gly Asp Thr Leu Tyr Trp Thr Asp Trp Gln Thr
                245                 250                 255

Arg Ser Ile His Ala Cys Asn Lys Trp Thr Gly Glu Gln Arg Lys Glu
            260                 265                 270

Ile Leu Ser Ala Leu Tyr Ser Pro Met Asp Ile Gln Val Leu Ser Gln
            275                 280                 285

Glu Arg Gln Pro Pro Phe His Thr Pro Cys Glu Glu Asp Asn Gly Gly
            290                 295                 300

-continued

```
Cys Ser His Leu Cys Leu Leu Ser Pro Arg Glu Pro Phe Tyr Ser Cys
305                 310                 315                 320

Ala Cys Pro Thr Gly Val Gln Leu Gln Asp Asn Gly Lys Thr Cys Lys
                325                 330                 335

Thr Gly Ala Glu Glu Val Leu Leu Leu Ala Arg Arg Thr Asp Leu Arg
            340                 345                 350

Arg Ile Ser Leu Asp Thr Pro Asp Phe Thr Asp Ile Val Leu Gln Val
        355                 360                 365

Gly Asp Ile Arg His Ala Ile Ala Ile Asp Tyr Asp Pro Leu Glu Gly
    370                 375                 380

Tyr Val Tyr Trp Thr Asp Glu Val Arg Ala Ile Arg Arg Ala Tyr
385                 390                 395                 400

Leu Asp Gly Ser Gly Ala Gln Thr Leu Val Asn Thr Glu Ile Asn Asp
                405                 410                 415

Pro Asp Gly Ile Ala Val Asp Trp Val Ala Arg Asn Leu Tyr Trp Thr
            420                 425                 430

Asp Thr Gly Thr Asp Arg Ile Glu Val Thr Arg Leu Asn Gly Thr Ser
        435                 440                 445

Arg Lys Ile Leu Val Ser Glu Asp Leu Asp Glu Pro Arg Ala Ile Val
    450                 455                 460

Leu His Pro Val Met Gly Leu Met Tyr Trp Thr Asp Trp Gly Glu Asn
465                 470                 475                 480

Pro Lys Ile Glu Cys Ala Asn Leu Asp Gly Arg Asp Arg His Val Leu
                485                 490                 495

Val Asn Thr Ser Leu Gly Trp Pro Asn Gly Leu Ala Leu Asp Leu Gln
            500                 505                 510

Glu Gly Lys Leu Tyr Trp Gly Asp Ala Lys Thr Asp Lys Ile Glu Val
        515                 520                 525

Ile Asn Ile Asp Gly Thr Lys Arg Lys Thr Leu Leu Glu Asp Lys Leu
    530                 535                 540

Pro His Ile Phe Gly Phe Thr Leu Leu Gly Asp Phe Ile Tyr Trp Thr
545                 550                 555                 560

Asp Trp Gln Arg Arg Ser Ile Glu Arg Val His Lys Val Lys Ala Ser
                565                 570                 575

Arg Asp Val Ile Ile Asp Gln Leu Pro Asp Leu Met Gly Leu Lys Ala
            580                 585                 590

Val Asn Val Ala Lys Val Val Gly Thr Asn Pro Cys Ala Asp Gly Asn
        595                 600                 605

Gly Gly Cys Ser His Leu Cys Phe Phe Thr Pro Arg Ala Thr Lys Cys
    610                 615                 620

Gly Cys Pro Ile Gly Leu Glu Leu Leu Ser Asp Met Lys Thr Cys Ile
625                 630                 635                 640

Ile Pro Glu Ala Phe Leu Val Phe Thr Ser Arg Ala Thr Ile His Arg
                645                 650                 655

Ile Ser Leu Glu Thr Asn Asn Asn Asp Val Ala Ile Pro Leu Thr Gly
            660                 665                 670

Val Lys Glu Ala Ser Ala Leu Asp Phe Asp Val Ser Asn Asn His Ile
        675                 680                 685

Tyr Trp Thr Asp Val Ser Leu Lys Thr Ile Ser Arg Ala Phe Met Asn
    690                 695                 700

Gly Ser Ser Val Glu His Val Ile Glu Phe Gly Leu Asp Tyr Pro Glu
705                 710                 715                 720
```

Gly Met Ala Val Asp Trp Met Gly Lys Asn Leu Tyr Trp Ala Asp Thr
                725                 730                 735

Gly Thr Asn Arg Ile Glu Val Ala Arg Leu Asp Gly Gln Phe Arg Gln
            740                 745                 750

Val Leu Val Trp Arg Asp Leu Asp Asn Pro Arg Ser Leu Ala Leu Asp
        755                 760                 765

Pro Thr Lys Gly Tyr Ile Tyr Trp Thr Glu Trp Gly Gly Lys Pro Arg
    770                 775                 780

Ile Val Arg Ala Phe Met Asp Gly Thr Asn Cys Met Thr Leu Val Asp
785                 790                 795                 800

Lys Val Gly Arg Ala Asn Asp Leu Thr Ile Asp Tyr Ala Asp Gln Arg
            805                 810                 815

Leu Tyr Trp Thr Asp Leu Asp Thr Asn Met Ile Glu Ser Ser Asn Met
        820                 825                 830

Leu Gly Gln Glu Arg Met Val Ile Ala Asp Asp Leu Pro Tyr Pro Phe
    835                 840                 845

Gly Leu Thr Gln Tyr Ser Asp Tyr Ile Tyr Trp Thr Asp Trp Asn Leu
            850                 855                 860

His Ser Ile Glu Arg Ala Asp Lys Thr Ser Gly Arg Asn Arg Thr Leu
865                 870                 875                 880

Ile Gln Gly His Leu Asp Phe Val Met Asp Ile Leu Val Phe His Ser
            885                 890                 895

Ser Arg Gln Asp Gly Leu Asn Asp Cys Val His Ser Asn Gly Gln Cys
        900                 905                 910

Gly Gln Leu Cys Leu Ala Ile Pro Gly Gly His Arg Cys Gly Cys Ala
    915                 920                 925

Ser His Tyr Thr Leu Asp Pro Ser Ser Arg Asn Cys Ser Pro Pro Ser
930                 935                 940

Thr Phe Leu Leu Phe Ser Gln Lys Phe Ala Ile Ser Arg Met Ile Pro
945                 950                 955                 960

Asp Asp Gln Leu Ser Pro Asp Leu Val Leu Pro Leu His Gly Leu Arg
            965                 970                 975

Asn Val Lys Ala Ile Asn Tyr Asp Pro Leu Asp Lys Phe Ile Tyr Trp
        980                 985                 990

Val Asp Gly Arg Gln Asn Ile Lys Arg Ala Lys Asp Asp Gly Thr Gln
    995                 1000                1005

Pro Ser Met Leu Thr Ser Pro Ser Gln Ser Leu Ser Pro Asp Arg
    1010                1015                1020

Gln Pro His Asp Leu Ser Ile Asp Ile Tyr Ser Arg Thr Leu Phe
    1025                1030                1035

Trp Thr Cys Glu Ala Thr Asn Thr Ile Asn Val His Arg Leu Asp
    1040                1045                1050

Gly Asp Ala Met Gly Val Val Leu Arg Gly Asp Arg Asp Lys Pro
    1055                1060                1065

Arg Ala Ile Ala Val Asn Ala Glu Arg Gly Tyr Met Tyr Phe Thr
    1070                1075                1080

Asn Met Gln Asp His Ala Ala Lys Ile Glu Arg Ala Ser Leu Asp
    1085                1090                1095

Gly Thr Glu Arg Glu Val Leu Phe Thr Thr Gly Leu Ile Arg Pro
    1100                1105                1110

Val Ala Leu Val Val Asp Asn Ala Leu Gly Lys Leu Phe Trp Val
    1115                1120                1125

Asp Ala Asp Leu Lys Arg Ile Glu Ser Cys Asp Leu Ser Gly Ala

| | | | | | | | | | | |
|---|---|---|---|---|---|---|---|---|---|---|
| | | 1130 | | | 1135 | | | | 1140 | |
| Asn | Arg | Leu | Thr | Leu | Glu | Asp | Ala | Asn | Ile | Val | Gln | Pro | Val | Gly |
| | | 1145 | | | | 1150 | | | | 1155 | |
| Leu | Thr | Val | Leu | Gly | Arg | His | Leu | Tyr | Trp | Ile | Asp | Arg | Gln | Gln |
| | 1160 | | | | | 1165 | | | | 1170 | |
| Gln | Met | Ile | Glu | Arg | Val | Glu | Lys | Thr | Thr | Gly | Asp | Lys | Arg | Thr |
| 1175 | | | | | 1180 | | | | | 1185 | |
| Arg | Val | Gln | Gly | Arg | Val | Thr | His | Leu | Thr | Gly | Ile | His | Ala | Val |
| | 1190 | | | | | 1195 | | | | 1200 | |
| Glu | Glu | Val | Ser | Leu | Glu | Glu | Phe | Ser | Ala | His | Pro | Cys | Ala | Arg |
| 1205 | | | | | 1210 | | | | | 1215 | |
| Asp | Asn | Gly | Gly | Cys | Ser | His | Ile | Cys | Ile | Ala | Lys | Gly | Asp | Gly |
| 1220 | | | | | 1225 | | | | | 1230 | |
| Thr | Pro | Arg | Cys | Ser | Cys | Pro | Val | His | Leu | Val | Leu | Leu | Gln | Asn |
| 1235 | | | | | 1240 | | | | | 1245 | |
| Leu | Leu | Thr | Cys | Gly | Glu | Pro | Pro | Thr | Cys | Ser | Pro | Asp | Gln | Phe |
| | 1250 | | | | | 1255 | | | | 1260 | |
| Ala | Cys | Thr | Thr | Gly | Glu | Ile | Asp | Cys | Ile | Pro | Gly | Ala | Trp | Arg |
| 1265 | | | | | 1270 | | | | | 1275 | |
| Cys | Asp | Gly | Phe | Pro | Glu | Cys | Ala | Asp | Gln | Ser | Asp | Glu | Glu | Gly |
| 1280 | | | | | 1285 | | | | | 1290 | |
| Cys | Pro | Val | Cys | Ser | Ala | Ser | Gln | Phe | Pro | Cys | Ala | Arg | Gly | Gln |
| 1295 | | | | | 1300 | | | | | 1305 | |
| Cys | Val | Asp | Leu | Arg | Leu | Arg | Cys | Asp | Gly | Glu | Ala | Asp | Cys | Gln |
| 1310 | | | | | 1315 | | | | | 1320 | |
| Asp | Arg | Ser | Asp | Glu | Ala | Asn | Cys | Asp | Ala | Val | Cys | Leu | Pro | Asn |
| 1325 | | | | | 1330 | | | | | 1335 | |
| Gln | Phe | Arg | Cys | Thr | Ser | Gly | Gln | Cys | Val | Leu | Ile | Lys | Gln | Gln |
| 1340 | | | | | 1345 | | | | | 1350 | |
| Cys | Asp | Ser | Phe | Pro | Asp | Cys | Ala | Asp | Gly | Ser | Asp | Glu | Leu | Met |
| 1355 | | | | | 1360 | | | | | 1365 | |
| Cys | Glu | Ile | Asn | Lys | Pro | Pro | Ser | Asp | Asp | Ile | Pro | Ala | His | Ser |
| 1370 | | | | | 1375 | | | | | 1380 | |
| Ser | | | | | | | | | | | |

<210> SEQ ID NO 13
<211> LENGTH: 4845
<212> TYPE: DNA
<213> ORGANISM: Mouse

<400> SEQUENCE: 13

```
atggaaacgg cgccgacccg ggcccctccg ccgccgccgc cgccgctgct gctgctggtg      60
ctgtactgca gcttggtccc cgccgcggcc tcaccgctcc tgttgtttgc caaccgccgg     120
gatgtgcggc tagtggatgc cggcggagtg aagctggagt ccaccattgt ggccagtggc     180
ctggaggatg cagctgctgt agacttccag ttctccaagg gtgctgtgta ctggacagat     240
gtgagcgagg aggccatcaa acagacctac ctgaaccaga ctggagctgc tgcacagaac     300
attgtcatct cggcctcgt gtcacctgat ggcctggcct gtgactgggt tgcaagaag      360 ctgtactgga cggactccga gaccaaccgc attgaggttg ccaacctcaa tgggacgtcc     420
cgtaaggttc tcttctggca ggacctggac cagccaaggg ccattgccct ggatcctgca     480
catgggtaca tgtactggac tgactggggg gaagcacccc ggatcgagcg ggcagggatg     540
gatggcagta cccggaagat cattgtagac tccgacattt actggccaa tgggctgacc     600
```

```
atcgacctgg aggaacagaa gctgtactgg gccgatgcca agctcagctt catccaccgt    660
gccaacctgg acggctcctt ccggcagaag gtggtggagg gcagcctcac tcacccttt     720 gccctgacac tctctgggga cacactctac tggacagact ggcagacccg ctccatccac    780
gcctgcaaca agtggacagg ggagcagagg aaggagatcc ttagtgctct gtactcaccc    840
atggacatcc aagtgctgag ccaggagcgg cagcctccct tccacacacc atgcgaggag    900
gacaacggtg gctgttccca cctgtgcctg ctgtccccga gggagccttt ctactcctgt    960
gcctgcccca ctggtgtgca gttgcaggac aatggcaaga cgtgcaagac aggggctgag   1020
gaagtgctgc tgctggctcg gaggacagac ctgaggagga tctctctgga cacccctgac   1080
ttcacagaca tagtgctgca ggtgggcgac atccggcatg ccattgccat tgactacgat   1140
cccctggagg gctacgtgta ctggaccgat gatgaggtgc gggctatccg cagggcgtac   1200
ctagatggct caggtgcgca gacacttgtg aacactgaga tcaatgaccc cgatggcatt   1260
gctgtggact gggtcgcccg gaacctctac tggacagata caggcactga cagaattgag   1320
gtgactcgcc tcaacggcac ctcccgaaag atcctggtat ctgaggacct ggacgaaccg   1380
cgagccattg tgttgcaccc tgtgatgggc ctcatgtact ggacagactg ggggagaac    1440 cccaaaatcg aatgcgccaa cctagatggg agagatcggc atgtcctggt gaacacctcc   1500
cttgggtggc ccaatggact ggccctggac ctgcaggagg gcaagctgta ctgggggat    1560 gccaaaactg ataaaatcga ggtgatcaac atagacggga caaagcggaa gaccctgctt   1620
gaggacaagc tcccacacat ttttgggttc acactgctgg gggacttcat ctactggacc   1680
gactggcaga gacgcagtat tgaaagggtc cacaaggtca aggccagccg ggatgtcatc   1740
attgatcaac tccccgacct gatgggactc aaagccgtga atgtggccaa ggttgtcgga   1800
accaacccat gtgcggatgg aaatggaggg tgcagccatc tgtgcttctt caccccacgt   1860
gccaccaagt gtggctgccc cattggcctg agctgttgga gtgacatgaa gacctgcata   1920
atccccgagg ccttcctggt attcaccagc agagccacca tccacaggat ctccctggag   1980
actaacaaca cgatgtggc tatcccactc acgggtgtca agaggcctc tgcactggac     2040 tttgatgtgt ccaacaatca catctactgg actgatgtta gcctcaagac gatcagccga   2100
gccttcatga atgggagctc agtggagcac gtgattgagt ttggcctcga ctaccctgaa   2160
ggaatggctg tggactggat gggcaagaac ctctattggg cggacacagg gaccaacagg   2220
attgaggtgg cccggctgga tgggcagttc cggcaggtgc ttgtgtggag agaccttgac   2280
aaccccaggt ctctggctct ggatcctact aaaggctaca tctactggac tgagtggggt   2340
ggcaagccaa ggattgtgcg ggccttcatg gatgggacca attgtatgac actggtagac   2400
aaggtgggcc gggccaacga cctcaccatt gattatgccg accagcgact gtactggact   2460
gacctggaca ccaacatgat tgagtcttcc aacatgctgg gtcaggagcg catggtgata   2520 gctgacatc tgcctacc gtttggcctg actcaatata gcgattacat ctactggact       2580
gactggaacc tgcatagcat tgaacgggcg gacaagacca gtgggcggaa ccgcacccc    2640 atccagggtc acctggactt cgtcatggac atcctggtgt ccactcctc ccgtcaggat    2700 ggcctcaacg actgcgtgca cagcaatggc cagtgtgggc agctgtgcct cgccatcccc   2760
ggaggccacc gctgtggctg tgcttcacac tacacgctgg accccagcag ccgcaactgc   2820
agcccgccct ccaccttctt gctgttcagc cagaaatttg ccatcagccg gatgatcccc   2880
gatgaccagc tcagcccgga ccttgtccta ccccttcatg ggctgaggaa cgtcaaagcc   2940
```

| | | |
|---|---|---|
| atcaactatg acccgctgga caagttcatc tactgggtgg acgggcgcca gaacatcaag | 3000 | |
| agggccaagg acgacggtac ccagccctcc atgctgacct ctcccagcca aagcctgagc | 3060 | |
| ccagacagac agccacacga cctcagcatt gacatctaca gccggacact gttctggacc | 3120 | |
| tgtgaggcca ccaacactat caatgtccac cggctggatg gggatgccat gggagtggtg | 3180 | |
| cttcgagggg accgtgacaa gccaagggcc attgctgtca atgctgagcg agggtacatg | 3240 | |
| tactttacca acatgcagga ccatgctgcc aagatcgagc gagcctccct ggatggcaca | 3300 | |
| gagcgggagg tcctcttcac cacaggcctc atccgtcccg tggcccttgt ggtggacaat | 3360 | |
| gctctgggca agctcttctg ggtggatgcc gacctaaagc gaatcgaaag ctgtgacctc | 3420 | |
| tctggggcca accgcctgac cctggaagat gccaacatcg tacagccagt aggtctgaca | 3480 | |
| gtgctgggca gcaccctcta ctggatcgac cgccagcagc agatgatcga gcgcgtggag | 3540 | |
| aagaccactg gggacaagcg gactagggtt cagggccgtg tcacccacct gacaggcatc | 3600 | |
| catgccgtgg aggaagtcag cctggaggag ttctcagccc atccttgtgc ccgagacaat | 3660 | |
| ggcggctgct cccacatctg tatcgccaag ggtgatggaa caccgcgctg ctcgtgccct | 3720 | |
| gtccacctgg tgctcctgca gaacctgctg acttgtggtg agcctcctac ctgctcccct | 3780 | |
| gatcagtttg catgtaccac tggtgagatc gactgcatcc ccggagcctg cgctgtgac | 3840 | |
| ggcttccctg agtgtgctga ccagagtgat gaagaaggct gcccagtgtg ctccgcctct | 3900 | |
| cagttcccct cgctcgaggc cagtgtgtg acctgcgcgt tacgctgcga cggtgaggcc | 3960 | |
| gactgccagg atcgctctga tgaagctaac tgcgatgctg tctgtctgcc caatcagttc | 4020 | |
| cggtgcacca gcgccagtg tgtcctcatc aagcaacagt gtgactcctt ccccgactgt | 4080 | |
| gctgatgggt ctgatgagct catgtgtgaa atcaacaagc caccctctga tgacatccca | 4140 | |
| gcccacagca gtgccattgg gcccgtcatt ggtatcatcc tctccctctt cgtcatgggc | 4200 | |
| ggggtctact ttgtctgcca gcgtgtgatg tgccagcgct acacaggggc cagtgggccc | 4260 | |
| tttccccacg agtatgttgg tggagcccct catgtgcctc tcaacttcat agccccaggt | 4320 | |
| ggctcacagc acggtcccct cccaggcatc ccgtgcagca gtccgtgat gagctccatg | 4380 | |
| agcctggtgg gggggcgcgg cagcgtgccc ctctatgacc ggaatcacgt cactggggcc | 4440 | |
| tcatccagca gctcgtccag cacaaaggcc acactatatc gccgatcct gaacccaccc | 4500 | |
| ccgtccccgg ccacagaccc ctctctctac aacgtggacg tgttttattc ttcaggcatc | 4560 | |
| ccggccaccg ctagaccata caggccctac gtcattcgag gtatggcacc cccaacaaca | 4620 | |
| ccgtgcagca cagatgtgtg tgacagtgac tacagcatca gtcgctggaa gagcagcaaa | 4680 | |
| tactacctgg acttgaattc ggactcagac ccctaccccc cccgcccac cccccacagc | 4740 | |
| cagtacctat ctgcagagga cagctgccca ccctcaccag gcactgagag gagttactgc | 4800 | |
| cacctcttcc cgccccacc gtccccctgc acggactcgt cctga | 4845 | |

<210> SEQ ID NO 14
<211> LENGTH: 1614
<212> TYPE: PRT
<213> ORGANISM: Mouse

<400> SEQUENCE: 14

Met Glu Thr Ala Pro Thr Arg Ala Pro Pro Pro Pro Pro Pro Pro Leu
1               5                   10                  15

Leu Leu Leu Val Leu Tyr Cys Ser Leu Val Pro Ala Ala Ala Ser Pro
            20                  25                  30

Leu Leu Leu Phe Ala Asn Arg Arg Asp Val Arg Leu Val Asp Ala Gly

```
              35                  40                  45
Gly Val Lys Leu Glu Ser Thr Ile Val Ala Ser Gly Leu Glu Asp Ala
             50                  55                  60
Ala Ala Val Asp Phe Gln Phe Ser Lys Gly Ala Val Tyr Trp Thr Asp
 65                  70                  75                  80
Val Ser Glu Glu Ala Ile Lys Gln Thr Tyr Leu Asn Gln Thr Gly Ala
                 85                  90                  95
Ala Ala Gln Asn Ile Val Ile Ser Gly Leu Val Ser Pro Asp Gly Leu
            100                 105                 110
Ala Cys Asp Trp Val Gly Lys Lys Leu Tyr Trp Thr Asp Ser Glu Thr
            115                 120                 125
Asn Arg Ile Glu Val Ala Asn Leu Asn Gly Thr Ser Arg Lys Val Leu
            130                 135                 140
Phe Trp Gln Asp Leu Asp Gln Pro Arg Ala Ile Ala Leu Asp Pro Ala
145                 150                 155                 160
His Gly Tyr Met Tyr Trp Thr Asp Trp Gly Ala Pro Arg Ile Glu
                165                 170                 175
Arg Ala Gly Met Asp Gly Ser Thr Arg Lys Ile Ile Val Asp Ser Asp
                180                 185                 190
Ile Tyr Trp Pro Asn Gly Leu Thr Ile Asp Leu Glu Glu Gln Lys Leu
            195                 200                 205
Tyr Trp Ala Asp Ala Lys Leu Ser Phe Ile His Arg Ala Asn Leu Asp
210                 215                 220
Gly Ser Phe Arg Gln Lys Val Val Glu Gly Ser Leu Thr His Pro Phe
225                 230                 235                 240
Ala Leu Thr Leu Ser Gly Asp Thr Leu Tyr Trp Thr Asp Trp Gln Thr
                245                 250                 255
Arg Ser Ile His Ala Cys Asn Lys Trp Thr Gly Glu Gln Arg Lys Glu
                260                 265                 270
Ile Leu Ser Ala Leu Tyr Ser Pro Met Asp Ile Gln Val Leu Ser Gln
            275                 280                 285
Glu Arg Gln Pro Pro Phe His Thr Pro Cys Glu Glu Asp Asn Gly Gly
            290                 295                 300
Cys Ser His Leu Cys Leu Leu Ser Pro Arg Glu Pro Phe Tyr Ser Cys
305                 310                 315                 320
Ala Cys Pro Thr Gly Val Gln Leu Gln Asp Asn Gly Lys Thr Cys Lys
                325                 330                 335
Thr Gly Ala Glu Glu Val Leu Leu Leu Ala Arg Arg Thr Asp Leu Arg
                340                 345                 350
Arg Ile Ser Leu Asp Thr Pro Asp Phe Thr Asp Ile Val Leu Gln Val
            355                 360                 365
Gly Asp Ile Arg His Ala Ile Ala Ile Asp Tyr Asp Pro Leu Glu Gly
            370                 375                 380
Tyr Val Tyr Trp Thr Asp Asp Glu Val Arg Ala Ile Arg Arg Ala Tyr
385                 390                 395                 400
Leu Asp Gly Ser Gly Ala Gln Thr Leu Val Asn Thr Glu Ile Asn Asp
                405                 410                 415
Pro Asp Gly Ile Ala Val Asp Trp Val Ala Arg Asn Leu Tyr Trp Thr
                420                 425                 430
Asp Thr Gly Thr Asp Arg Ile Glu Val Thr Arg Leu Asn Gly Thr Ser
            435                 440                 445
Arg Lys Ile Leu Val Ser Glu Asp Leu Asp Glu Pro Arg Ala Ile Val
            450                 455                 460
```

```
Leu His Pro Val Met Gly Leu Met Tyr Trp Thr Asp Trp Gly Glu Asn
465                 470                 475                 480

Pro Lys Ile Glu Cys Ala Asn Leu Asp Gly Arg Asp Arg His Val Leu
            485                 490                 495

Val Asn Thr Ser Leu Gly Trp Pro Asn Gly Leu Ala Leu Asp Leu Gln
        500                 505                 510

Glu Gly Lys Leu Tyr Trp Gly Asp Ala Lys Thr Asp Lys Ile Glu Val
    515                 520                 525

Ile Asn Ile Asp Gly Thr Lys Arg Lys Thr Leu Leu Glu Asp Lys Leu
530                 535                 540

Pro His Ile Phe Gly Phe Thr Leu Leu Gly Asp Phe Ile Tyr Trp Thr
545                 550                 555                 560

Asp Trp Gln Arg Arg Ser Ile Glu Arg Val His Lys Val Lys Ala Ser
                565                 570                 575

Arg Asp Val Ile Ile Asp Gln Leu Pro Asp Leu Met Gly Leu Lys Ala
            580                 585                 590

Val Asn Val Ala Lys Val Val Gly Thr Asn Pro Cys Ala Asp Gly Asn
        595                 600                 605

Gly Gly Cys Ser His Leu Cys Phe Phe Thr Pro Arg Ala Thr Lys Cys
610                 615                 620

Gly Cys Pro Ile Gly Leu Glu Leu Leu Ser Asp Met Lys Thr Cys Ile
625                 630                 635                 640

Ile Pro Glu Ala Phe Leu Val Phe Thr Ser Arg Ala Thr Ile His Arg
                645                 650                 655

Ile Ser Leu Glu Thr Asn Asn Asn Asp Val Ala Ile Pro Leu Thr Gly
            660                 665                 670

Val Lys Glu Ala Ser Ala Leu Asp Phe Asp Val Ser Asn Asn His Ile
        675                 680                 685

Tyr Trp Thr Asp Val Ser Leu Lys Thr Ile Ser Arg Ala Phe Met Asn
690                 695                 700

Gly Ser Ser Val Glu His Val Ile Glu Phe Gly Leu Asp Tyr Pro Glu
705                 710                 715                 720

Gly Met Ala Val Asp Trp Met Gly Lys Asn Leu Tyr Trp Ala Asp Thr
                725                 730                 735

Gly Thr Asn Arg Ile Glu Val Ala Arg Leu Asp Gly Gln Phe Arg Gln
            740                 745                 750

Val Leu Val Trp Arg Asp Leu Asp Asn Pro Arg Ser Leu Ala Leu Asp
        755                 760                 765

Pro Thr Lys Gly Tyr Ile Tyr Trp Thr Glu Trp Gly Gly Lys Pro Arg
770                 775                 780

Ile Val Arg Ala Phe Met Asp Gly Thr Asn Cys Met Thr Leu Val Asp
785                 790                 795                 800

Lys Val Gly Arg Ala Asn Asp Leu Thr Ile Asp Tyr Ala Asp Gln Arg
                805                 810                 815

Leu Tyr Trp Thr Asp Leu Asp Thr Asn Met Ile Glu Ser Ser Asn Met
            820                 825                 830

Leu Gly Gln Glu Arg Met Val Ile Ala Asp Asp Leu Pro Tyr Pro Phe
        835                 840                 845

Gly Leu Thr Gln Tyr Ser Asp Tyr Ile Tyr Trp Thr Asp Trp Asn Leu
850                 855                 860

His Ser Ile Glu Arg Ala Asp Lys Thr Ser Gly Arg Asn Arg Thr Leu
865                 870                 875                 880
```

-continued

Ile Gln Gly His Leu Asp Phe Val Met Asp Ile Leu Val Phe His Ser
                885                 890                 895

Ser Arg Gln Asp Gly Leu Asn Asp Cys Val His Ser Asn Gly Gln Cys
            900                 905                 910

Gly Gln Leu Cys Leu Ala Ile Pro Gly Gly His Arg Cys Gly Cys Ala
            915                 920                 925

Ser His Tyr Thr Leu Asp Pro Ser Ser Arg Asn Cys Ser Pro Pro Ser
    930                 935                 940

Thr Phe Leu Leu Phe Ser Gln Lys Phe Ala Ile Ser Arg Met Ile Pro
945                 950                 955                 960

Asp Asp Gln Leu Ser Pro Asp Leu Val Leu Pro Leu His Gly Leu Arg
                965                 970                 975

Asn Val Lys Ala Ile Asn Tyr Asp Pro Leu Asp Lys Phe Ile Tyr Trp
            980                 985                 990

Val Asp Gly Arg Gln Asn Ile Lys Arg Ala Lys Asp Asp Gly Thr Gln
        995                 1000                1005

Pro Ser Met Leu Thr Ser Pro Gln Ser Leu Ser Pro Asp Arg
    1010                1015                1020

Gln Pro His Asp Leu Ser Ile Asp Ile Tyr Ser Arg Thr Leu Phe
    1025                1030                1035

Trp Thr Cys Glu Ala Thr Asn Thr Ile Asn Val His Arg Leu Asp
    1040                1045                1050

Gly Asp Ala Met Gly Val Val Leu Arg Gly Asp Arg Asp Lys Pro
    1055                1060                1065

Arg Ala Ile Ala Val Asn Ala Glu Arg Gly Tyr Met Tyr Phe Thr
    1070                1075                1080

Asn Met Gln Asp His Ala Ala Lys Ile Glu Arg Ala Ser Leu Asp
    1085                1090                1095

Gly Thr Glu Arg Glu Val Leu Phe Thr Thr Gly Leu Ile Arg Pro
    1100                1105                1110

Val Ala Leu Val Val Asp Asn Ala Leu Gly Lys Leu Phe Trp Val
    1115                1120                1125

Asp Ala Asp Leu Lys Arg Ile Glu Ser Cys Asp Leu Ser Gly Ala
    1130                1135                1140

Asn Arg Leu Thr Leu Glu Asp Ala Asn Ile Val Gln Pro Val Gly
    1145                1150                1155

Leu Thr Val Leu Gly Arg His Leu Tyr Trp Ile Asp Arg Gln Gln
    1160                1165                1170

Gln Met Ile Glu Arg Val Glu Lys Thr Thr Gly Asp Lys Arg Thr
    1175                1180                1185

Arg Val Gln Gly Arg Val Thr His Leu Thr Gly Ile His Ala Val
    1190                1195                1200

Glu Glu Val Ser Leu Glu Glu Phe Ser Ala His Pro Cys Ala Arg
    1205                1210                1215

Asp Asn Gly Gly Cys Ser His Ile Cys Ile Ala Lys Gly Asp Gly
    1220                1225                1230

Thr Pro Arg Cys Ser Cys Pro Val His Leu Val Leu Leu Gln Asn
    1235                1240                1245

Leu Leu Thr Cys Gly Glu Pro Pro Thr Cys Ser Pro Asp Gln Phe
    1250                1255                1260

Ala Cys Thr Thr Gly Glu Ile Asp Cys Ile Pro Gly Ala Trp Arg
    1265                1270                1275

Cys Asp Gly Phe Pro Glu Cys Ala Asp Gln Ser Asp Glu Glu Gly

```
                1280                1285                1290

Cys Pro Val Cys Ser Ala Ser Gln Phe Pro Cys Ala Arg Gly Gln
    1295                1300                1305

Cys Val Asp Leu Arg Leu Arg Cys Asp Gly Glu Ala Asp Cys Gln
    1310                1315                1320

Asp Arg Ser Asp Glu Ala Asn Cys Asp Ala Val Cys Leu Pro Asn
    1325                1330                1335

Gln Phe Arg Cys Thr Ser Gly Gln Cys Val Leu Ile Lys Gln Gln
    1340                1345                1350

Cys Asp Ser Phe Pro Asp Cys Ala Asp Gly Ser Asp Glu Leu Met
    1355                1360                1365

Cys Glu Ile Asn Lys Pro Pro Ser Asp Asp Ile Pro Ala His Ser
    1370                1375                1380

Ser Ala Ile Gly Pro Val Ile Gly Ile Ile Leu Ser Leu Phe Val
    1385                1390                1395

Met Gly Gly Val Tyr Phe Val Cys Gln Arg Val Met Cys Gln Arg
    1400                1405                1410

Tyr Thr Gly Ala Ser Gly Pro Phe Pro His Glu Tyr Val Gly Gly
    1415                1420                1425

Ala Pro His Val Pro Leu Asn Phe Ile Ala Pro Gly Gly Ser Gln
    1430                1435                1440

His Gly Pro Phe Pro Gly Ile Pro Cys Ser Lys Ser Val Met Ser
    1445                1450                1455

Ser Met Ser Leu Val Gly Gly Arg Gly Ser Val Pro Leu Tyr Asp
    1460                1465                1470

Arg Asn His Val Thr Gly Ala Ser Ser Ser Ser Ser Ser Ser Thr
    1475                1480                1485

Lys Ala Thr Leu Tyr Pro Pro Ile Leu Asn Pro Pro Pro Ser Pro
    1490                1495                1500

Ala Thr Asp Pro Ser Leu Tyr Asn Val Asp Val Phe Tyr Ser Ser
    1505                1510                1515

Gly Ile Pro Ala Thr Ala Arg Pro Tyr Arg Pro Tyr Val Ile Arg
    1520                1525                1530

Gly Met Ala Pro Pro Thr Thr Pro Cys Ser Thr Asp Val Cys Asp
    1535                1540                1545

Ser Asp Tyr Ser Ile Ser Arg Trp Lys Ser Ser Lys Tyr Tyr Leu
    1550                1555                1560

Asp Leu Asn Ser Asp Ser Asp Pro Tyr Pro Pro Pro Thr Pro
    1565                1570                1575

His Ser Gln Tyr Leu Ser Ala Glu Asp Ser Cys Pro Pro Ser Pro
    1580                1585                1590

Gly Thr Glu Arg Ser Tyr Cys His Leu Phe Pro Pro Pro Pro Ser
    1595                1600                1605

Pro Cys Thr Asp Ser Ser
    1610

<210> SEQ ID NO 15
<211> LENGTH: 14
<212> TYPE: PRT
<213> ORGANISM: Human

<400> SEQUENCE: 15

Glu Asn Asn Lys Thr Met Asn Arg Ala Glu Asn Gly Gly Arg
1               5                   10
```

<210> SEQ ID NO 16
<211> LENGTH: 16
<212> TYPE: PRT
<213> ORGANISM: Human

<400> SEQUENCE: 16

His Pro Phe Glu Thr Lys Asp Val Ser Glu Tyr Ser Cys Arg Glu Leu
1               5                   10                  15

<210> SEQ ID NO 17
<211> LENGTH: 17
<212> TYPE: PRT
<213> ORGANISM: Human

<400> SEQUENCE: 17

Arg Glu Leu His Phe Thr Arg Tyr Val Thr Asp Gly Pro Cys Arg Ser
1               5                   10                  15

Ala

<210> SEQ ID NO 18
<211> LENGTH: 12
<212> TYPE: PRT
<213> ORGANISM: Human

<400> SEQUENCE: 18

Leu Cys Pro Gly Gly Glu Ala Pro Arg Ala Arg Lys
1               5                   10

<210> SEQ ID NO 19
<211> LENGTH: 615
<212> TYPE: DNA
<213> ORGANISM: Mouse

<400> SEQUENCE: 19
atgcagccct cactagcccc gtgcctcatc tgcctacttg tgcacgctgc cttctgtgct     60
gtggagggcc aggggtggca agccttcagg aatgatgcca cagaggtcat cccagggctt    120
ggagagtacc ccgagcctac tcctgagaac aaccagacca tgaaccgggc ggagaatggt    180
ggcagacctc cccaccatcc ctatgacgcc aaagatgtgt ccgagtacag ctgccgcgag    240
ctgcactaca cccgcttcct gacagacggc ccatgccgca gcgccaagcc ggtcaccgag    300
ttggtgtgct ccggccagtg cggccccgcg cggctgctgc caacgccat cgggcgcgtg     360
aagtggtggc gcccgaacgg accggatttc gctgcatcc ggatcgcta ccgcgcgcag      420
cgggtgcagc tgctgtgccc cggggggcgcg gcgccacgct cgcgcaaggt gcgtctggtg   480
gcctcgtgca agtgcaagcg cccccaccccgc ttccacaacc agtcggagct caaggacttc  540
gggccggaga ccgcgcggcc gcagaagggt cgcaagccgc ggcccggcgc ccggggagcc   600
aaagccaacc aggcg                                                    615

<210> SEQ ID NO 20
<211> LENGTH: 203
<212> TYPE: PRT
<213> ORGANISM: Mouse

<400> SEQUENCE: 20

Met Gln Pro Ser Leu Ala Pro Cys Leu Ile Cys Leu Leu Val His Ala
1               5                   10                  15

Ala Phe Cys Ala Val Glu Gly Gln Gly Trp Gln Ala Phe Arg Asn Asp
                20                  25                  30

```
Ala Thr Glu Val Ile Pro Gly Leu Gly Glu Tyr Pro Glu Pro Pro Pro
         35                  40                  45

Glu Asn Asn Gln Thr Met Asn Arg Ala Glu Asn Gly Gly Arg Pro Pro
 50                      55                  60

His His Pro Tyr Asp Ala Lys Asp Val Ser Glu Tyr Ser Cys Arg Glu
 65                  70                  75                  80

Leu His Tyr Thr Arg Phe Leu Thr Asp Gly Pro Cys Arg Ser Ala Lys
                 85                  90                  95

Pro Val Thr Glu Leu Val Cys Ser Gly Gln Cys Gly Pro Ala Arg Leu
             100                 105                 110

Leu Pro Asn Ala Ile Gly Arg Val Lys Trp Trp Arg Pro Asn Gly Pro
             115                 120                 125

Asp Phe Arg Cys Ile Pro Asp Arg Tyr Arg Ala Gln Arg Val Gln Leu
             130                 135                 140

Leu Cys Pro Gly Gly Ala Ala Pro Arg Ser Arg Lys Val Arg Leu Val
145                 150                 155                 160

Ala Ser Cys Lys Cys Lys Arg Leu Thr Arg Phe His Asn Gln Ser Glu
                 165                 170                 175

Leu Lys Asp Phe Gly Pro Glu Thr Ala Arg Pro Gln Lys Gly Arg Lys
             180                 185                 190

Pro Arg Pro Gly Ala Arg Gly Ala Lys Ala Asn
             195                 200

<210> SEQ ID NO 21
<211> LENGTH: 203
<212> TYPE: PRT
<213> ORGANISM: Artificial
<220> FEATURE:
<223> OTHER INFORMATION: Wise/SOST Peptides

<400> SEQUENCE: 21

Met Gln Pro Ser Leu Ala Pro Cys Leu Ile Cys Leu Leu Val His Ala
 1               5                  10                  15

Ala Phe Cys Ala Val Glu Gly Gln Gly Trp Gln Ala Phe Arg Asn Asp
                 20                  25                  30

Ala Thr Glu Val Ile Pro Gly Leu Gly Glu Tyr Pro Glu Pro Pro Pro
         35                  40                  45

Glu Asn Asn Gln Thr Met Asn Arg Ala Glu Asn Gly Gly Arg Pro Pro
 50                      55                  60

His His Pro Tyr Asp Ala Lys Asp Val Ser Glu Tyr Ser Cys Arg Glu
 65                  70                  75                  80

Leu His Tyr Thr Arg Phe Leu Thr Asp Gly Pro Cys Arg Ser Ala Lys
                 85                  90                  95

Pro Val Thr Glu Leu Val Cys Ser Gly Gln Cys Gly Pro Ala Arg Leu
             100                 105                 110

Leu Pro Asn Ala Ile Gly Arg Val Lys Trp Trp Arg Pro Asn Gly Pro
             115                 120                 125

Asp Phe Arg Cys Ile Pro Asp Arg Tyr Arg Ala Gln Arg Val Gln Leu
             130                 135                 140

Leu Cys Pro Gly Gly Ala Ala Pro Arg Ser Arg Lys Val Arg Leu Val
145                 150                 155                 160

Ala Ser Cys Lys Cys Lys Arg Leu Thr Arg Phe His Asn Gln Ser Glu
                 165                 170                 175

Leu Lys Asp Phe Gly Pro Glu Thr Ala Arg Pro Gln Lys Gly Arg Lys
             180                 185                 190
```

```
Pro Arg Pro Gly Ala Arg Gly Ala Lys Ala Asn
        195                 200
```

<210> SEQ ID NO 22
<211> LENGTH: 14
<212> TYPE: PRT
<213> ORGANISM: Artificial
<220> FEATURE:
<223> OTHER INFORMATION: Wise/SOST Peptides

<400> SEQUENCE: 22

```
Leu Asn Asn Lys Thr Met Asn Arg Ala Glu Asn Gly Gly Arg
1               5                   10
```

<210> SEQ ID NO 23
<211> LENGTH: 14
<212> TYPE: PRT
<213> ORGANISM: Artificial
<220> FEATURE:
<223> OTHER INFORMATION: Wise/SOST Peptides

<400> SEQUENCE: 23

```
Ser Ser Asn Ser Thr Met Asn Gln Ala Arg Asn Gly Gly Arg
1               5                   10
```

<210> SEQ ID NO 24
<211> LENGTH: 14
<212> TYPE: PRT
<213> ORGANISM: Artificial
<220> FEATURE:
<223> OTHER INFORMATION: Wise/SOST Peptides

<400> SEQUENCE: 24

```
Ala Asn Ser Ser Ala Leu Asn Gln Ala Arg Asn Gly Gly Arg
1               5                   10
```

<210> SEQ ID NO 25
<211> LENGTH: 14
<212> TYPE: PRT
<213> ORGANISM: Artificial
<220> FEATURE:
<223> OTHER INFORMATION: Wise/SOST Peptides

<400> SEQUENCE: 25

```
Ala Asn Ser Ser Thr Leu Asn Gln Ala Arg Asn Gly Gly Arg
1               5                   10
```

<210> SEQ ID NO 26
<211> LENGTH: 14
<212> TYPE: PRT
<213> ORGANISM: Artificial
<220> FEATURE:
<223> OTHER INFORMATION: Wise/SOST Peptides

<400> SEQUENCE: 26

```
Ser Ser Ser Asn Gly Gly Asn Arg Ala Lys Ser Gly Gly Arg
1               5                   10
```

<210> SEQ ID NO 27
<211> LENGTH: 14
<212> TYPE: PRT
<213> ORGANISM: Artificial
<220> FEATURE:
<223> OTHER INFORMATION: Wise/SOST Peptides

<400> SEQUENCE: 27

```
Ala Ser Ser Asn Ala Gly Asn Arg Ala Lys Ser Gly Ala Arg
```

```
<210> SEQ ID NO 28
<211> LENGTH: 14
<212> TYPE: PRT
<213> ORGANISM: Artificial
<220> FEATURE:
<223> OTHER INFORMATION: Wise/SOST Peptides

<400> SEQUENCE: 28

Ser Asn Asn Asn Thr Met Asn Gln Ala Lys His Gly Gly Arg
1               5                   10

<210> SEQ ID NO 29
<211> LENGTH: 14
<212> TYPE: PRT
<213> ORGANISM: Artificial
<220> FEATURE:
<223> OTHER INFORMATION: Wise/SOST Peptides

<400> SEQUENCE: 29

Glu Asn Asn Gln Thr Met Asn Arg Ala Glu Asn Gly Gly Arg
1               5                   10

<210> SEQ ID NO 30
<211> LENGTH: 16
<212> TYPE: PRT
<213> ORGANISM: Artificial
<220> FEATURE:
<223> OTHER INFORMATION: Wise/SOST Peptides

<400> SEQUENCE: 30

His Pro Phe Glu Thr Lys Asp Ala Ser Glu Tyr Ser Cys Arg Glu Leu
1               5                   10                  15

<210> SEQ ID NO 31
<211> LENGTH: 16
<212> TYPE: PRT
<213> ORGANISM: Artificial
<220> FEATURE:
<223> OTHER INFORMATION: Wise/SOST Peptides

<400> SEQUENCE: 31

His Pro Tyr Asp Ala Lys Gly Val Ser Glu Tyr Ser Cys Arg Glu Leu
1               5                   10                  15

<210> SEQ ID NO 32
<211> LENGTH: 16
<212> TYPE: PRT
<213> ORGANISM: Artificial
<220> FEATURE:
<223> OTHER INFORMATION: Wise/SOST Peptides

<400> SEQUENCE: 32

His Pro Tyr Asp Thr Lys Asp Val Ser Glu Tyr Ser Cys Arg Glu Leu
1               5                   10                  15

<210> SEQ ID NO 33
<211> LENGTH: 16
<212> TYPE: PRT
<213> ORGANISM: Artificial
<220> FEATURE:
<223> OTHER INFORMATION: Wise/SOST Peptides

<400> SEQUENCE: 33

Gln Ala Pro Asp Pro Asn Asp Val Ser Asp Phe Ser Cys Arg Glu Met
1               5                   10                  15
```

```
<210> SEQ ID NO 34
<211> LENGTH: 16
<212> TYPE: PRT
<213> ORGANISM: Artificial
<220> FEATURE:
<223> OTHER INFORMATION: Wise/SOST Peptides

<400> SEQUENCE: 34

Thr Gly Leu Asp Arg Asn Thr Arg Val Gln Val Gly Cys Arg Glu Leu
1               5                   10                  15

<210> SEQ ID NO 35
<211> LENGTH: 16
<212> TYPE: PRT
<213> ORGANISM: Artificial
<220> FEATURE:
<223> OTHER INFORMATION: Wise/SOST Peptides

<400> SEQUENCE: 35

Thr Gly Leu Asp Arg Asn Ser Arg Val Gln Val Gly Cys Arg Glu Leu
1               5                   10                  15

<210> SEQ ID NO 36
<211> LENGTH: 16
<212> TYPE: PRT
<213> ORGANISM: Artificial
<220> FEATURE:
<223> OTHER INFORMATION: Wise/SOST Peptides

<400> SEQUENCE: 36

Thr Gly Ser Asp Arg Asn Asn Arg Val Gln Val Gly Cys Arg Glu Leu
1               5                   10                  15

<210> SEQ ID NO 37
<211> LENGTH: 16
<212> TYPE: PRT
<213> ORGANISM: Artificial
<220> FEATURE:
<223> OTHER INFORMATION: Wise/SOST Peptides

<400> SEQUENCE: 37

Ser Ala Met Asp Arg Thr Asn Pro His Gln Val Gly Cys Arg Glu Leu
1               5                   10                  15

<210> SEQ ID NO 38
<211> LENGTH: 16
<212> TYPE: PRT
<213> ORGANISM: Artificial
<220> FEATURE:
<223> OTHER INFORMATION: Wise/SOST Peptides

<400> SEQUENCE: 38

Ser Ala Leu Asp Arg Thr Asn His His Gln Val Gly Cys Arg Glu Leu
1               5                   10                  15

<210> SEQ ID NO 39
<211> LENGTH: 16
<212> TYPE: PRT
<213> ORGANISM: Artificial
<220> FEATURE:
<223> OTHER INFORMATION: Wise/SOST Peptides

<400> SEQUENCE: 39

Thr Ser Ser Val Thr Tyr Ser Ala Ser Glu Leu Ser Cys Arg Glu Leu
1               5                   10                  15
```

<210> SEQ ID NO 40
<211> LENGTH: 16
<212> TYPE: PRT
<213> ORGANISM: Artificial
<220> FEATURE:
<223> OTHER INFORMATION: Wise/SOST Peptides

<400> SEQUENCE: 40

Thr Ser Thr Val Ser Tyr Ser Ala Ser Glu Leu Ser Cys Arg Glu Leu
1               5                   10                  15

<210> SEQ ID NO 41
<211> LENGTH: 17
<212> TYPE: PRT
<213> ORGANISM: Artificial
<220> FEATURE:
<223> OTHER INFORMATION: Wise/SOST Peptides

<400> SEQUENCE: 41

Arg Glu Leu Arg Ser Thr Lys Tyr Ile Ser Asp Gly Gln Cys Thr Ser
1               5                   10                  15

Ile

<210> SEQ ID NO 42
<211> LENGTH: 16
<212> TYPE: PRT
<213> ORGANISM: Artificial
<220> FEATURE:
<223> OTHER INFORMATION: Wise/SOST Peptodes

<400> SEQUENCE: 42

Lys Thr Gln Pro Leu Lys Gln Thr Ile His Glu Asp Gly Cys Asn Ser
1               5                   10                  15

<210> SEQ ID NO 43
<211> LENGTH: 17
<212> TYPE: PRT
<213> ORGANISM: Artificial
<220> FEATURE:
<223> OTHER INFORMATION: Wise/SOST Peptides

<400> SEQUENCE: 43

Arg Glu Leu Arg Ser Thr Arg Tyr Val Thr Asp Gly Ser Cys Arg Ser
1               5                   10                  15

Ala

<210> SEQ ID NO 44
<211> LENGTH: 17
<212> TYPE: PRT
<213> ORGANISM: Artificial
<220> FEATURE:
<223> OTHER INFORMATION: Wise/SOST Peptides

<400> SEQUENCE: 44

Arg Glu Met Arg Ile Thr Arg Tyr Val Thr Glu Gly Pro Cys Arg Ser
1               5                   10                  15

Leu

<210> SEQ ID NO 45
<211> LENGTH: 17
<212> TYPE: PRT
<213> ORGANISM: Artificial
<220> FEATURE:
<223> OTHER INFORMATION: Wise/SOST Peptides

```
<400> SEQUENCE: 45

Arg Glu Leu His Tyr Thr Arg Phe Leu Thr Asp Gly Pro Cys Arg Ser
1               5                   10                  15

Ala

<210> SEQ ID NO 46
<211> LENGTH: 15
<212> TYPE: PRT
<213> ORGANISM: Artificial
<220> FEATURE:
<223> OTHER INFORMATION: Wise/SOST Peptides

<400> SEQUENCE: 46

Glu Leu Val Cys Ser Gly Gln Cys Gly Pro Ala Arg Leu Leu Pro
1               5                   10                  15

<210> SEQ ID NO 47
<211> LENGTH: 15
<212> TYPE: PRT
<213> ORGANISM: Artificial
<220> FEATURE:
<223> OTHER INFORMATION: Wise/SOST Peptides

<400> SEQUENCE: 47

Glu Leu Val Cys Ser Gly Gln Cys Val Pro Ser His Leu Leu Pro
1               5                   10                  15

<210> SEQ ID NO 48
<211> LENGTH: 15
<212> TYPE: PRT
<213> ORGANISM: Artificial
<220> FEATURE:
<223> OTHER INFORMATION: Wise/SOST Peptides

<400> SEQUENCE: 48

Glu Leu Val Cys Ser Gly Gln Cys Leu Pro Ala His Leu Met Pro
1               5                   10                  15

<210> SEQ ID NO 49
<211> LENGTH: 15
<212> TYPE: PRT
<213> ORGANISM: Artificial
<220> FEATURE:
<223> OTHER INFORMATION: Wise/SOST Peptides

<400> SEQUENCE: 49

Glu Leu Val Cys Thr Gly Gln Cys Leu Pro Ala Gln Met Leu Pro
1               5                   10                  15

<210> SEQ ID NO 50
<211> LENGTH: 15
<212> TYPE: PRT
<213> ORGANISM: Artificial
<220> FEATURE:
<223> OTHER INFORMATION: Wise/SOST Peptides

<400> SEQUENCE: 50

Glu Leu Val Cys Ala Gly Glu Cys Leu Pro Leu Pro Ile Leu Pro
1               5                   10                  15

<210> SEQ ID NO 51
<211> LENGTH: 15
<212> TYPE: PRT
<213> ORGANISM: Artificial
<220> FEATURE:
<223> OTHER INFORMATION: Wise/SOST Peptides
```

```
<400> SEQUENCE: 51

Glu Leu Val Cys Ala Gly Glu Cys Leu Pro Leu Pro Leu Leu Pro
1               5                   10                  15

<210> SEQ ID NO 52
<211> LENGTH: 15
<212> TYPE: PRT
<213> ORGANISM: Artificial
<220> FEATURE:
<223> OTHER INFORMATION: Wise/SOST Peptides

<400> SEQUENCE: 52

Glu Leu Val Cys Ala Gly Glu Cys Leu Pro Leu Pro Val Leu Pro
1               5                   10                  15

<210> SEQ ID NO 53
<211> LENGTH: 15
<212> TYPE: PRT
<213> ORGANISM: Artificial
<220> FEATURE:
<223> OTHER INFORMATION: Wise/SOST Peptides

<400> SEQUENCE: 53

Glu Leu Val Cys Ser Gly Gln Cys Gly Pro Ala Arg Leu Leu Pro
1               5                   10                  15

<210> SEQ ID NO 54
<211> LENGTH: 15
<212> TYPE: PRT
<213> ORGANISM: Artificial
<220> FEATURE:
<223> OTHER INFORMATION: Wise/SOST Peptides

<400> SEQUENCE: 54

Glu Leu Val Cys Ala Gly Glu Cys Leu Pro Leu Ser Val Leu Pro
1               5                   10                  15

<210> SEQ ID NO 55
<211> LENGTH: 15
<212> TYPE: PRT
<213> ORGANISM: Artificial
<220> FEATURE:
<223> OTHER INFORMATION: Wise/SOST Peptides

<400> SEQUENCE: 55

Glu Leu Val Cys Ser Gly Gln Cys Gly Pro Ala Arg Leu Leu Pro
1               5                   10                  15

<210> SEQ ID NO 56
<211> LENGTH: 21
<212> TYPE: PRT
<213> ORGANISM: Artificial
<220> FEATURE:
<223> OTHER INFORMATION: Wise/SOST Peptides

<400> SEQUENCE: 56

Asn Ala Ile Gly Arg Gly Lys Trp Trp Arg Pro Ser Gly Pro Asp Phe
1               5                   10                  15

Arg Cys Ile Pro Asp
            20

<210> SEQ ID NO 57
<211> LENGTH: 25
<212> TYPE: PRT
<213> ORGANISM: Artificial
```

```
<220> FEATURE:
<223> OTHER INFORMATION: Wise/SOST Peptides

<400> SEQUENCE: 57

Asn Trp Ile Gly Gly Gly Tyr Gly Thr Lys Tyr Trp Ser Arg Arg Ser
1               5                   10                  15

Ser Gln Glu Trp Arg Cys Val Asn Asp
            20                  25

<210> SEQ ID NO 58
<211> LENGTH: 25
<212> TYPE: PRT
<213> ORGANISM: Artificial
<220> FEATURE:
<223> OTHER INFORMATION: Wise Peptides

<400> SEQUENCE: 58

Asn Trp Ile Gly Gly Gly Tyr Gly Thr Lys Tyr Trp Ser Arg Arg Ser
1               5                   10                  15

Ser Gln Glu Trp Arg Cys Val Asn Asp
            20                  25

<210> SEQ ID NO 59
<211> LENGTH: 21
<212> TYPE: PRT
<213> ORGANISM: Artificial
<220> FEATURE:
<223> OTHER INFORMATION: Wise Peptides

<400> SEQUENCE: 59

Asn Ala Ile Gly Arg Gly Lys Trp Trp Arg Pro Ser Gly Pro Asp Phe
1               5                   10                  15

Arg Cys Ile Pro Asp
            20

<210> SEQ ID NO 60
<211> LENGTH: 25
<212> TYPE: PRT
<213> ORGANISM: Artificial
<220> FEATURE:
<223> OTHER INFORMATION: Wise Peptides

<400> SEQUENCE: 60

Asn Trp Ile Gly Gly Gly Tyr Gly Thr Lys Tyr Trp Ser Arg Arg Ser
1               5                   10                  15

Ser Gln Glu Trp Arg Cys Val Asn Asp
            20                  25

<210> SEQ ID NO 61
<211> LENGTH: 25
<212> TYPE: PRT
<213> ORGANISM: Artificial
<220> FEATURE:
<223> OTHER INFORMATION: Wise/SOST Peptides

<400> SEQUENCE: 61

Asn Trp Ile Gly Gly Gly Tyr Gly Thr Lys Tyr Trp Ser Arg Arg Gly
1               5                   10                  15

Ser Gln Glu Trp Arg Cys Val Asn Asp
            20                  25

<210> SEQ ID NO 62
<211> LENGTH: 24
<212> TYPE: PRT
```

<213> ORGANISM: Artificial
<220> FEATURE:
<223> OTHER INFORMATION: Wise/SOST Peptides

<400> SEQUENCE: 62

Asn Trp Ile Gly Gly Tyr Gly Lys Lys Ser Trp Asn Arg Arg Asn Ser
1               5                   10                  15

Gln Glu Trp Arg Cys Val Asn Asp
            20

<210> SEQ ID NO 63
<211> LENGTH: 21
<212> TYPE: PRT
<213> ORGANISM: Artificial
<220> FEATURE:
<223> OTHER INFORMATION: Wise/SOST Peptides

<400> SEQUENCE: 63

Asn Thr Ile Gly Arg Gly Lys Trp Trp Arg Ser Asn Thr Ser Glu Tyr
1               5                   10                  15

Arg Cys Ile Pro Ala
            20

<210> SEQ ID NO 64
<211> LENGTH: 21
<212> TYPE: PRT
<213> ORGANISM: Artificial
<220> FEATURE:
<223> OTHER INFORMATION: Wise/SOST Peptides

<400> SEQUENCE: 64

Asn Thr Ile Gly Arg Ala Lys Trp Trp Arg Ser Ser Thr Ser Glu Tyr
1               5                   10                  15

Arg Cys Val Pro Ala
            20

<210> SEQ ID NO 65
<211> LENGTH: 21
<212> TYPE: PRT
<213> ORGANISM: Artificial
<220> FEATURE:
<223> OTHER INFORMATION: Wise/SOST Peptides

<400> SEQUENCE: 65

Asn Ser Ile Gly Arg Gly Lys Trp Trp Arg Gln Asn Ser Pro Asp Tyr
1               5                   10                  15

Arg Cys Ile Pro Ala
            20

<210> SEQ ID NO 66
<211> LENGTH: 21
<212> TYPE: PRT
<213> ORGANISM: Artificial
<220> FEATURE:
<223> OTHER INFORMATION: Wise/SOST Peptides

<400> SEQUENCE: 66

Asn Ala Ile Gly Arg Val Lys Trp Trp Arg Pro Asn Gly Pro Asp Phe
1               5                   10                  15

Arg Cys Ile Pro Asp
            20

<210> SEQ ID NO 67
<211> LENGTH: 21

```
<212> TYPE: PRT
<213> ORGANISM: Artificial
<220> FEATURE:
<223> OTHER INFORMATION: Wise/SOST Peptides

<400> SEQUENCE: 67

Asn Ala Ile Gly Arg Gly Lys Trp Trp Arg Pro Ser Gly Pro Asp Phe
1               5                   10                  15
Arg Cys Ile Pro Asp
            20

<210> SEQ ID NO 68
<211> LENGTH: 13
<212> TYPE: PRT
<213> ORGANISM: Artificial
<220> FEATURE:
<223> OTHER INFORMATION: Wise/SOST Peptides

<400> SEQUENCE: 68

Leu Leu Cys Pro Gly Gly Ala Ala Pro Arg Ala Arg Lys
1               5                   10

<210> SEQ ID NO 69
<211> LENGTH: 13
<212> TYPE: PRT
<213> ORGANISM: Artificial
<220> FEATURE:
<223> OTHER INFORMATION: Wise/SOST Peptides

<400> SEQUENCE: 69

Leu Leu Cys Pro Gly Gly Glu Ala Pro Arg Ala Arg Lys
1               5                   10

<210> SEQ ID NO 70
<211> LENGTH: 12
<212> TYPE: PRT
<213> ORGANISM: Artificial
<220> FEATURE:
<223> OTHER INFORMATION: Wise/SOST Peptides

<400> SEQUENCE: 70

Leu Gln Cys Gln Asp Gly Ser Thr Arg Thr Tyr Lys
1               5                   10

<210> SEQ ID NO 71
<211> LENGTH: 12
<212> TYPE: PRT
<213> ORGANISM: Artificial
<220> FEATURE:
<223> OTHER INFORMATION: Wise/SOST Peptides

<400> SEQUENCE: 71

Leu Gln Cys Glu Asp Gly Thr Thr Arg Thr Tyr Lys
1               5                   10

<210> SEQ ID NO 72
<211> LENGTH: 12
<212> TYPE: PRT
<213> ORGANISM: Artificial
<220> FEATURE:
<223> OTHER INFORMATION: Wise/SOST Peptides

<400> SEQUENCE: 72

Leu Gln Cys Pro Asn Gly Asn Thr Arg Thr Tyr Lys
1               5                   10
```

```
<210> SEQ ID NO 73
<211> LENGTH: 12
<212> TYPE: PRT
<213> ORGANISM: Artificial
<220> FEATURE:
<223> OTHER INFORMATION: Wise/SOST Peptides

<400> SEQUENCE: 73

Leu Arg Cys Pro Asn Gly Asn Thr Arg Thr Tyr Lys
1               5                   10

<210> SEQ ID NO 74
<211> LENGTH: 12
<212> TYPE: PRT
<213> ORGANISM: Artificial
<220> FEATURE:
<223> OTHER INFORMATION: Wise/SOST Peptides

<400> SEQUENCE: 74

Met Ala Cys Pro Glu Asp Glu Thr Arg Thr Tyr Lys
1               5                   10

<210> SEQ ID NO 75
<211> LENGTH: 13
<212> TYPE: PRT
<213> ORGANISM: Artificial
<220> FEATURE:
<223> OTHER INFORMATION: Wise/SOST Peptides

<400> SEQUENCE: 75

Leu Leu Cys Pro Gly Gly Ala Ala Pro Arg Ser Arg Lys
1               5                   10

<210> SEQ ID NO 76
<211> LENGTH: 11
<212> TYPE: PRT
<213> ORGANISM: Artificial
<220> FEATURE:
<223> OTHER INFORMATION: Wise/SOST Peptides

<400> SEQUENCE: 76

Asp Thr Gly Thr Asp Arg Ile Glu Val Thr Arg
1               5                   10

<210> SEQ ID NO 77
<211> LENGTH: 11
<212> TYPE: PRT
<213> ORGANISM: Artificial
<220> FEATURE:
<223> OTHER INFORMATION: Wise/SOST Peptides

<400> SEQUENCE: 77

Asp Thr Val Thr Asp Arg Ile Glu Val Cys Arg
1               5                   10

<210> SEQ ID NO 78
<211> LENGTH: 11
<212> TYPE: PRT
<213> ORGANISM: Artificial
<220> FEATURE:
<223> OTHER INFORMATION: Wise/SOST Peptides
<220> FEATURE:
<221> NAME/KEY: misc_feature
<222> LOCATION: (4)..(4)
<223> OTHER INFORMATION: Xaa can be any naturally occurring amino acid

<400> SEQUENCE: 78

Asp Thr Val Xaa Asp Arg Ile Glu Val Cys Arg
```

<210> SEQ ID NO 79
<211> LENGTH: 11
<212> TYPE: PRT
<213> ORGANISM: Artificial
<220> FEATURE:
<223> OTHER INFORMATION: Wise/SOST Peptides

<400> SEQUENCE: 79

Asp Ala Gly Thr Asp Arg Ile Glu Val Ala Asn
1               5                   10

<210> SEQ ID NO 80
<211> LENGTH: 11
<212> TYPE: PRT
<213> ORGANISM: Artificial
<220> FEATURE:
<223> OTHER INFORMATION: Wise/SOST Peptides

<400> SEQUENCE: 80

Asp Ala Gly Thr Asp Arg Ile Glu Val Ala Asn
1               5                   10

<210> SEQ ID NO 81
<211> LENGTH: 11
<212> TYPE: PRT
<213> ORGANISM: Artificial
<220> FEATURE:
<223> OTHER INFORMATION: Wise/SOST Peptides

<400> SEQUENCE: 81

Asn Lys Ile Thr Gln Thr Ile Glu Ile Ile Arg
1               5                   10

<210> SEQ ID NO 82
<211> LENGTH: 11
<212> TYPE: PRT
<213> ORGANISM: Artificial
<220> FEATURE:
<223> OTHER INFORMATION: Wise/SOST Peptides

<400> SEQUENCE: 82

Asp Arg Gly Arg Ser Leu Ile Glu Gly Ser Asp
1               5                   10

<210> SEQ ID NO 83
<211> LENGTH: 546
<212> TYPE: DNA
<213> ORGANISM: Dog

<400> SEQUENCE: 83
atgcagctct ctcttgctct gtgtctcgtc tgcttgctgg tgcatgcagc cttccgtgca      60
gtggagggcc aggggtggca ggccttcaag aacgatgcca cagaaatcat ccccgagctg     120
ggcgagtacc ccgagcctcc accagagctg gagaacaaca gaccatgaa ccgggcggag     180 aacggagggc ggccccctca ccatcccttt gagaccaaag acgcatccga gtacagctgc    240
cgcgagctgc acttcacccg ctacgtgacg gacgggccgt gccgcagcgc caagccggtc    300
accgagctgg tgtgctcggg ccagtgcggc cccgcgcgcc tgctgcccaa cgccatcggc    360
cgcggcaagt ggtggcgccc gagcgggccc gacttccgct gcatccccga ccgctaccgc    420
gcgcagcggg tgcagctgct gttgcgcctg gtggcctcgt gcaagtgcaa gcgactcacc    480
cgcttccaca accagtccga gctcaaggac ttcgggcccg aggccgcgcg ccgcagaag    540

-continued

```
ggccga                                                                546
```

<210> SEQ ID NO 84
<211> LENGTH: 642
<212> TYPE: DNA
<213> ORGANISM: Chimp

<400> SEQUENCE: 84

```
atgcagctcc cactggccct gtgtctcgtc tgcctgctgg tacacacagc cttccgtgta     60
gtggagggcc aggggtggca ggcgttcaag aatgatgcca cggaaatcat ccccgagctc    120
ggagagtacc ccgagcctcc accggagctg agaacaaca agaccatgaa ccgggcggag    180
aacggagggc ggcctcccca ccacccctttgagaccaaag acgtgtccga gtacagctgc    240
cgcgagctgc acttcacccg ctacgtgacc gatgggccgt gccgcagcgc caagccggtc    300
accgagctgg tgtgctccgg ccagtgcggc ccggcgcgcc tgctgcccaa cgccatcggc    360
cgcggcaagt ggtggcgacc tagtgggccc gacttccgct gcatccccga ccgctaccgc    420
gcgcagcgcg tgcagctgct gtgtccggt ggtgcggcgc cgcgcgcgcg caaggtgcgc    480
ctggtggcct cgtgcaagtg caagcgcctc acccgcttcc acaaccagtc ggagctcaag    540
gacttcggga ccgaggccgc tcggccgcag aagggccgga agccgcggcc ccgcgcccgg    600
agcgccaaag ccaaccaggc cgagctggag aacgcctact ag                      642
```

<210> SEQ ID NO 85
<211> LENGTH: 13
<212> TYPE: PRT
<213> ORGANISM: Chick

<400> SEQUENCE: 85

Ser Asn Asn Asn Thr Met Asn Gln Ala Lys Gly Gly Arg
1               5                   10

<210> SEQ ID NO 86
<211> LENGTH: 15
<212> TYPE: PRT
<213> ORGANISM: Chick

<400> SEQUENCE: 86

Ala Pro Asp Pro Asn Asp Val Ser Asp Phe Ser Cys Arg Glu Met
1               5                   10                  15

<210> SEQ ID NO 87
<211> LENGTH: 27
<212> TYPE: PRT
<213> ORGANISM: Chick

<400> SEQUENCE: 87

Arg Glu Met Arg Ile Thr Arg Tyr Val Thr Glu Gly Pro Cys Arg Ser
1               5                   10                  15

Leu Lys Pro Val Lys Glu Leu Val Cys Ser Gly
            20                  25

<210> SEQ ID NO 88
<211> LENGTH: 641
<212> TYPE: DNA
<213> ORGANISM: Chick

<400> SEQUENCE: 88

```
atgcagatct cctgggctgt gtgctctgtc tgcgtcctca tccaaatcgc atcccgggca     60
```

```
ctggagggtg gcaagtgttc aaaaatgatg cgacagaaat catccccgag atcaccgaaa    120
acacagagac cccaatggag cagatttaca gcaacaacaa cacgatgaac caggcaaagc    180 acggggaag gcacatacag caagctccgg accctaatga tgtctccgac ttcagctgca    240
gagagatgcg catcacccgc tacgtgacgg aggggccgtg ccgcagcctg aagcccgtga    300
aggagctggt gtgctcgggg cagtgcgtcc catcccacct cctgcccaac tccatcggca    360
gagggaagtg gtggaggcag aactcccggg attaccgctg catcccggct cacacccgca    420
cgcagcgcat ccagatggcg tgtcccgagg atgagactcg gacttacaaa ttccgagctg    480
tcacagcctg caaatgcaag cgctacactc ggtaccacaa ccagtccgag ctgaaggact    540 tgggaagga gccctccagg cagcagaaga acaagaagtc gcgtctgtcc cgagccagga    600
gcagcaaacc gaaccagcac gagctggaaa acgcctatta g                       641
```

<210> SEQ ID NO 89
<211> LENGTH: 555
<212> TYPE: DNA
<213> ORGANISM: Fugu
<400> SEQUENCE: 89

```
tggaaggtgc tgaagaacga cgccacagag attttaccgg actaccggga gcggagtccg     60
cacgagccga tgacgcaggc ggcgaacagc agcagtaacg gcgggaaccg cgcgaagagc    120
ggcgggagaa gcacgagctc ggtgacctac agtgcctcgg agctgagctg cagggagctg    180
cgttccaccc gctacgtcac cgatggatct tgccgcagcg ccaaacccat caaggagctg    240
gtgtgctcgg gccagtgcct gccagcgcac ctcatgccca acaccatcgg ccgcggcaag    300
tggtggcgga gcaacaccctc ggagtaccgc tgcatcccgg ctcactccag gaccaggagg    360
atccagctgc agtgccccaa cggcaacact cggacttaca aaatccgcat agtgacctcc    420
tgcaagtgta agcggttcag ggctcaccac aaccagtcgg aggccaagga ggtcctgagg    480
aggcagcgga gcaagaagcg cacgtctcaa ggacggagca aaaacaacac gcctttgatt    540
gacaattcat actga                                                     555
```

<210> SEQ ID NO 90
<211> LENGTH: 618
<212> TYPE: DNA
<213> ORGANISM: Mouse
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t
<400> SEQUENCE: 90

```
atgcttcctc ctgccattca tctctctctc attcccctgc tctgcatcct gatgagaaac     60
tgtttggctt ttaaaaatga tgccacagaa atcctttatt cacatgtggt taaacctgtc    120
ccggcacacc ccagcagcaa cagcacccctg aatcaagcca ggaatggagg caggcatttc    180
agtagcactg gactggatcg aaacagtcga gttcaagtgg gctgcaggga actgcggtcc    240
accaaataca tttcggacgg ccagtgcacc agcatcagcc ctntgaagga gctggtgtgc    300
gcgggcgagt gcttgcccct gccggtgctt cccaactgga tcggaggagg ctatggaaca    360
aagtactgga gccggaggag ctntcaggag tggcggtgtg tcaacgacaa gacgcgcacc    420
cagaggatcc agctgcagtg tcaggacggc agcacgcgca cctacaaaat caccgtggtc    480
```

```
acggcgtgca agtgcaagag gtacacccgt cagcacaacg agtccagcca caactttgaa    540
agcgtgtcgc cgccaagcc cgcccagcac cacagagagc ggaagagagc cagcaaatcc    600
agcaagcaca gtctgagc                                                  618
```

<210> SEQ ID NO 91
<211> LENGTH: 14
<212> TYPE: PRT
<213> ORGANISM: Mouse

<400> SEQUENCE: 91

```
Ser Ser Asn Ser Thr Leu Asn Gln Ala Arg Asn Gly Gly Arg
1               5                   10
```

<210> SEQ ID NO 92
<211> LENGTH: 621
<212> TYPE: DNA
<213> ORGANISM: Human

<400> SEQUENCE: 92

```
atgcttcctc ctgccattca tctctctctc attcccctgc tctgcatcct gatgaaaaac    60
tgtttggctt ttaaaaatga tgccacagaa atcctttatt cacatgtggt taaacctgtt   120
tcagcacacc ccagcagcaa cagcaccttg aatcaagcca ggaatggagg caggcacttc   180
agtagcacgg gactggatcg aaatagtcga gttcaagtgg gctgcaggga actgcggtcc   240
accaaataca tctcggatgg ccagtgcacc agcatcagcc ctctgaagga gctggtgtgc   300
gcgggtgagt gcttgcccct tgccagtgct tcccaactgga tcggaggagg ctacggaaca   360
aagtactgga gccggagggg ctcccaggag tggcggtgtg tcaacgacaa gacgcgcacc   420
cagagaatcc agctgcagtg tcaggacggc agcacacgca cctacaaaat caccgtggtc   480
acagcgtgca agtgcaagag gtacacccgg cagcacaacg agtccagcca caactttgaa   540
agcgtgtctc cgccaagcc cgcccagcac cacagagagc ggaagagagc cagcaaatcc   600
agcaagcaca gtctgagcta g                                              621
```

<210> SEQ ID NO 93
<211> LENGTH: 15
<212> TYPE: PRT
<213> ORGANISM: Human

<400> SEQUENCE: 93

```
Pro Ser Ser Asn Ser Thr Leu Asn Gln Ala Arg Asn Gly Gly Arg
1               5                   10                  15
```

<210> SEQ ID NO 94
<211> LENGTH: 642
<212> TYPE: DNA
<213> ORGANISM: Xenopus Leavis

<400> SEQUENCE: 94

```
atggttgtct caaggctcca gtgctgcatg ctctaccttg cgtgtattct catagaaagc    60
tgcgtgtctt ttaagaatga cgctacagaa atcctgtatt cccacgtgga taaacatatc   120
caagatagtg caaacagcag caccctgaat caggctagaa atgaggaag aaatgctgca   180 aactctgcac tggacagaac aaatcaccat caggttggat gcagagagct gagatctacc   240
aagtacatct cggatggaca gtgcaccagt atccagcctt tgaaagaact ggtctgtgct   300
ggagagtgtc ttcctctttc tattttggcc cactggatcg ggggtggcta cgggctgaaa   360
```

```
tattggagtc gaagaagttc ccaggaatgg agatgtgtca atgacaagac ccgcactcag      420
cgtatccagt tacagtgtga ggatggcact actagaacct acaaagtcac agtggttact      480
tcctgcaagt gcaagagata caccagacag cacaatgaat ccagccataa ctaccaagga      540
gcttctccca ttaaacccgt tcactctcac caacatcatc actcccacca caaccgtgat      600
aagaaaagac taatcaagat gtccaagcac attcctagct ag                         642
```

<210> SEQ ID NO 95
<211> LENGTH: 14
<212> TYPE: PRT
<213> ORGANISM: Xenopus Leavis

<400> SEQUENCE: 95

Arg Ser Thr Lys Tyr Ile Ser Asp Gly Gln Cys Thr Ser Ile
1               5                   10

<210> SEQ ID NO 96
<211> LENGTH: 642
<212> TYPE: DNA
<213> ORGANISM: Xenopus tropicalis

<400> SEQUENCE: 96

```
atggtcgtct caaggctcca atgctgcatg ttatactttg catgcatttt catagaaagc      60
tgcatgtctt ttaagaacga tgccacagaa atcctgtatt cccatgtgga taaaaacatc     120
caagagagtg ccaacagcag tgccctgaac caggctagga atggaggaag acacacggct     180
aactctgcca tggacaggac aaatccccat caagttggat gcaggagct gagatctaca      240 aagtacatct cagatgggca gtgcaccagt atccagcctt gaaagaact ggtctgtgct       300 ggagagtgtc ttcctcttcc tattttgccc aactggatcg ggggtggcta tgggctgaag     360
tactggagtc ggagaagctc tcaggaatgg agatgtgtca atgacaagac tcgcactcag     420
cgtatccagt tgcagtgtga ggatggcacg actagaacct acaaagtcac ggtggtaact     480
tcctgcaagt gcaagaggta caccaggcag cacaacgaat ccagccataa ctacgaagga     540
gcttctccaa tgaaacccat tcactctctc caacatcatc actcccacca caaccgtgat     600
aagaaaagac taatcaagat gtccaagcac attcctagct ag                         642
```

<210> SEQ ID NO 97
<211> LENGTH: 621
<212> TYPE: DNA
<213> ORGANISM: Chick

<400> SEQUENCE: 97

```
atgcttctct ccgccattca cttctacggc ttactcctag cttgcacctt cacgagaagc      60
tactcggctt tcaagaacga tgccactgag atactttatt cccacgtcgt taaacctgcc     120
cctgcgagcc cgagcagcaa cagcacgttg aaccaagcca ggaacggagg gaggcactac     180
gccggcacgg gctccgaccg taacaatcgc gttcaagttg ctgccgggga actgcgatct     240
accaagtaca tctcagacgg ccagtgcacc agcatcaatc ccctgaagga gctggtgtgt     300
gctggcgaat gcctcccctt gccgctcctg cccaactgga ttggaggagg ttatggaacc     360
aagtactgga gcagacggag ctcgcaagag tggagatgtg tcaatgacaa aactcgcacc     420
cagaggatcc agctgcagtg ccaggatgga agtataagaa cctacaaaat aactgtggtc     480
acggcctgca gtgcaagcg atacaccagg cagcacaacg agtccagcca caactttgag      540
ggaacctctc aagcaaagcc tgtccagcat cacaaagaga gaaaagagc cagtaaatcc      600
```
agcaaacata gtacaagtta g                                        621

<210> SEQ ID NO 98
<211> LENGTH: 15
<212> TYPE: PRT
<213> ORGANISM: Chick

<400> SEQUENCE: 98

Gly Ser Asp Arg Asn Asn Arg Val Gln Val Gly Cys Arg Glu Leu
1               5                   10                  15

<210> SEQ ID NO 99
<211> LENGTH: 621
<212> TYPE: DNA
<213> ORGANISM: Dog

<400> SEQUENCE: 99
atgcttcctc ctgccattca tctctctctc attcccctgc tctgcatcct gatgaaaaac     60
tgtttggctt ttaaaaatga tgccacagaa atcctttatt cacatgtggt taaacctgtt    120
tcagcacacc ccagcagcaa cagcaccttg aatcaagcca ggaatggagg caggcacttc    180
agtagcacgg gactggatcg aaatagtcga gttcaagtgg gctgcaggga actgcggtcc    240
accaaataca tctcggatgg ccagtgcacc agcatcagcc ctctgaagga gctggtgtgc    300
gcgggtgagt gcttgccctt gccagtgctt cccaactgga tcggaggagg ctacggaaca    360
aagtactgga gccggagggg ctcccaggag tggcggtgtg tcaacgacaa gacgcgcacc    420
cagagaatcc agctgcagtg tcaggacggc agcacacgca cctacaaaat caccgtggtc    480
acagcgtgca agtgcaagag gtacacccgg cagcacaacg agtccagcca caactttgaa    540
agcgtgtctc ccgccaagcc cgcccagcac cacagagagc ggaagagagc cagcaaatcc    600
agcaagcaca gtctgagcta g                                              621

<210> SEQ ID NO 100
<211> LENGTH: 625
<212> TYPE: DNA
<213> ORGANISM: Rat

<400> SEQUENCE: 100
atgcttcctc ctgccattca tctctctctc attcccctgc tctgcatcct gatgaaaaac     60
tgtttggctt ttaaaaatga tgccacagaa atcctttatt cacatgtggt taaacctgtt    120
tcagcacacc ccagcagcaa cagcaccttg aatcaagcca ggaatggagg caggcacttc    180
agtagcacgg gactggatcg aaatagtcga gttcaagtgg gctgcaggga actgcggtcc    240
accaaataca tctcggatgg ccagtgcacc agcatcagcc ctctgaagga gctggtgtgc    300
gcgggtgagt gcttgccctt gccagtgctt cccaactgga tcggaggagg ctacggaaca    360
aagtactgga gccggaggag ctcccaggag tggcggtgtg tcaacgacaa gacgcgcacc    420
cagagaatcc agctgcagtg tcaggacggc agcacacgca cctacaaaat caccgtggtc    480
acagcgtgca agtgcaagag gtacacccgg cagcacaacg agtccagcca caactttgaa    540
agcgtgtctc ccgccaagcc cgcccagcac cacagagagc ggaagagagc cagcaaatcc    600
agcaagcaca gtctgagcta gagct                                          625

<210> SEQ ID NO 101
<211> LENGTH: 14
<212> TYPE: PRT
<213> ORGANISM: Zebrafish

<400> SEQUENCE: 101

Thr His Asp Arg Glu Arg Ile Pro Val Gly Cys Arg Glu Leu
1               5                   10

<210> SEQ ID NO 102
<211> LENGTH: 608
<212> TYPE: DNA
<213> ORGANISM: Zebrafish

<400> SEQUENCE: 102

| | |
|---|---|
| cagagttgaa gcacatctct ccattggccg tgggtcatta cgcatcgcca tgtatataaa | 60 |
| cgcaccagag tcgtgcaatt tcatggtttt attttgcttt ttaataagga gtggtttgac | 120 |
| tttgaagaac gatgctacgg agatttttcta ctcgcatgtg gtcagtcccg ttcaggatgc | 180 |
| gcagagcaac gcgtctctca accgcgcgcg ctccggagga agaggcttca gcacgcacga | 240 |
| cagagaacga atcccagtag gctgcagaga gctccgatcc accaagtaca tctcagatgg | 300 |
| ccagtgcacc agcataaacc ctgtgaaaga gctggtgtgc acaggacagt gcctccccgc | 360 |
| tcagatgctg cccaattgga ttggaggata cggcaagaag tcctggaacc gccggaacag | 420 |
| tcaggaatgg cgctgtgtaa atgacaagac ccgaactcag cggattcagc tccagtgcca | 480 |
| ggatggcagc accaggacct acaagatcac agtggtgacc tcctgcaaat gcaaacgata | 540 |
| ctcgcggcaa cacaatgaat caggagttaa gtctgaggga tactctcata gccagatcaa | 600 |
| aaaacaga | 608 |

<210> SEQ ID NO 103
<211> LENGTH: 12
<212> TYPE: PRT
<213> ORGANISM: Fugu

<400> SEQUENCE: 103

Thr Tyr Ser Ala Ser Glu Leu Ser Cys Arg Glu Leu
1               5                   10

<210> SEQ ID NO 104
<211> LENGTH: 576
<212> TYPE: DNA
<213> ORGANISM: Fugu

<400> SEQUENCE: 104

| | |
|---|---|
| tgctgcaccg ccgcgcgcgg atggaaggtg ctgaagaacg acgccacaga gattttaccg | 60 |
| gactaccggg agcggagtcc gcacgagccg atgacgcagg cggcgaacag cagcagtaac | 120 |
| ggcgggaacc gcgcgaagag cggcgggaga agcacgagct cggtgaccta cagtgcctcg | 180 |
| gagctgagct gcagggagct gcgttccacc cgctacgtca ccgatggatc ttgccgcagc | 240 |
| gccaaaccca tcaaggagct ggtgtgctcg ggccagtgcc tgccagcgca cctcatgccc | 300 |
| aacaccatcg gccgcggcaa gtggtggcgg agcaacacct cggagtaccg ctgcatcccg | 360 |
| gctcactcca ggaccaggag gatccagctg cagtgcccca cggcaacac tcggacttac | 420 |
| aaaatccgca tagtgaccctc ctgcaagtgt aagcggttca gggctcacca caaccagtcg | 480 |
| gaggccaagg aggtcctgag gaggcagcgg agcaagaagc gcacgtctca aggacggagc | 540 |
| aaaaacaaca cgcctttgat tgacaattca tactga | 576 |

<210> SEQ ID NO 105
<211> LENGTH: 16
<212> TYPE: PRT
<213> ORGANISM: Pan troglodytes chimp

<400> SEQUENCE: 105

His Pro Ser Ser Asn Ser Thr Leu Asn Gln Ala Arg Asn Gly Gly Arg
1               5                   10                  15

<210> SEQ ID NO 106
<211> LENGTH: 618
<212> TYPE: DNA
<213> ORGANISM: Pan troglodytes chimp

<400> SEQUENCE: 106

```
atgcttcctc ctgccattca tttctatctc cttccccttg catgcatcct aatgaaaagc      60
tgtttggctt ttaaaaatga tgccacagaa atcctttatt cacatgtggt taaacctgtt     120
ccagcacacc ccagcagcaa cagcacgttg aatcaagcca gaaatggagg caggcatttc     180
agtaacactg gactggatcg gaacactcgg gttcaagtgg gttgccggga actgcgttcc     240
accaaataca tctctgatgg ccagtgcacc agcatcagcc ctctgaagga gctggtgtgt     300
gctggtgagt gcttgcccct gccagtgctc cctaactgga ttggaggagg ctatggaaca     360
aagtactgga gcaggaggag ctcccaggag tggcggtgtg tcaatgacaa aacccgtacc     420
cagagaatcc agctgcagtg ccaagatggc agcacacgca cctacaaaat cacagtagtc     480
actgcctgca gtgcaagag gtacacccgg cagcacaacg agtccagtca aactttgag      540
agcatgtcac ctgccaagcc agtccagcat cacagagagc ggaaaagagc cagcaaatcc     600
agcaagcaca gcatgagt                                                    618
```

<210> SEQ ID NO 107
<211> LENGTH: 633
<212> TYPE: DNA
<213> ORGANISM: Tetradon fish

<400> SEQUENCE: 107

```
atgcaggtgt ctctggtcct cctcgtgtcc agctcggcgc tcgtgctgct gcagggatgc      60
tgcgccgccg cgcgcggctg gaaggcgctg aagaacgacg ccaccgaggt tttagcggac     120
gaccgcgagc ggagcccgca cgagcccgcc gcgcacgcgg ccaacgccag cagtaacgcg     180
ggaaaccggg cgaagagcgg cgcgaggagc acgagcacgg tgtcctacag tgcctcggag     240
ctaagctgca gggagctgcg ctccacccgt tacgtcaccg atgggtcctg ccgcagcgcc     300
aaacccatca agagctggt gtgctcgggc cagtgcctgc cggcgcacct catgcccaac     360
accattggcc gggccaagtg gtggcggagc agcacctcgg agtaccgctg cgtcccggct     420
cactccaggc ccaggaggat ccagctgcgc tgccccaacg gcaacactcg gacttacaaa     480
atccgcacgg tgacctcctg caagtgcaag aggttccggg ctcaccacaa ccagtcggag     540
gccaaggagg tcccgaggag gcaacgcacc aagaagcggc catcccgagg ccgcagcaag     600
aaccccacgc ctttgattga caattcctac tga                                   633
```

<210> SEQ ID NO 108
<211> LENGTH: 621
<212> TYPE: DNA
<213> ORGANISM: Pongo pygmaeus

<400> SEQUENCE: 108

```
atgcttcctc ccgccattca tttctatctc cttccccttg catgcatcct aatgaaaagc      60
tgtttggctt ttaaaaatga tgccacagaa atcctttatt cacatgtggt taaacctgtt     120
ccagcacacc ccagcagcaa cagcacgttg aatcaagcca gaaatggagg caggcatttc     180
```

```
agtaacactg gactggatcg gaacactcgg gttcaagtgg gttgccggga actgcgttcc    240
accaaataca tctctgatgg ccagtgcacc agcatcagcc ctctgaagga gctggtgtgt    300
gctggcgagt gcttgcccct gtcagtgctc cctaactgga ttggaggagg ttatggaaca    360
aagtactgga gcaggaggag ctcccaggag tggcggtgcg tcaatgacaa aacccgtacc    420
cagagaatcc agctgcagtg ccaagatggc agcacacgca cctacaaaat cacagtagtc    480
actgcctgca gtgcaagag gtacacccgg cagcacaacg agtccagtca caactttgag    540
agcatgtcac ctgccaagcc agtccagcat cacagagagc ggaaaagagc cagcaaatcc    600
agcaagcaca gcatgagtta g                                              621
```

<210> SEQ ID NO 109
<211> LENGTH: 15
<212> TYPE: PRT
<213> ORGANISM: Artificial
<220> FEATURE:
<223> OTHER INFORMATION: LRP 5/6 Peptides

<400> SEQUENCE: 109

Leu Phe Ala Asn Arg Arg Asp Val Arg Leu Val Asp Ala Gly Gly
1               5                   10                  15

<210> SEQ ID NO 110
<211> LENGTH: 8
<212> TYPE: PRT
<213> ORGANISM: Artificial
<220> FEATURE:
<223> OTHER INFORMATION: LTRP 5/6 Peptides

<400> SEQUENCE: 110

Tyr Trp Thr Asp Val Ser Glu Glu
1               5

<210> SEQ ID NO 111
<211> LENGTH: 19
<212> TYPE: PRT
<213> ORGANISM: Artificial
<220> FEATURE:
<223> OTHER INFORMATION: LRP 5/6 Peptides

<400> SEQUENCE: 111

Lys Leu Tyr Trp Thr Asp Ser Glu Thr Asn Arg Ile Glu Val Ala Asn
1               5                   10                  15

Leu Asn Gly

<210> SEQ ID NO 112
<211> LENGTH: 7
<212> TYPE: PRT
<213> ORGANISM: Artificial
<220> FEATURE:
<223> OTHER INFORMATION: LRP 5/6 Peptides

<400> SEQUENCE: 112

Leu Phe Trp Gln Asp Leu Asp
1               5

<210> SEQ ID NO 113
<211> LENGTH: 23
<212> TYPE: PRT
<213> ORGANISM: Artificial
<220> FEATURE:
<223> OTHER INFORMATION: LRP 5/6 Peptides

```
<400> SEQUENCE: 113

Thr Asp Trp Gly Glu Thr Pro Arg Ile Glu Arg Ala Gly Met Asp Gly
1               5                   10                  15

Ser Thr Arg Lys Ile Ile Val
            20

<210> SEQ ID NO 114
<211> LENGTH: 11
<212> TYPE: PRT
<213> ORGANISM: Artificial
<220> FEATURE:
<223> OTHER INFORMATION: LRP 5/6 Peptides

<400> SEQUENCE: 114

His Ala Cys Asn Lys Arg Thr Gly Gly Lys Arg
1               5                   10

<210> SEQ ID NO 115
<211> LENGTH: 15
<212> TYPE: PRT
<213> ORGANISM: Artificial
<220> FEATURE:
<223> OTHER INFORMATION: LRP 5/6 Peptides

<400> SEQUENCE: 115

Thr Gly Val Gln Leu Gln Asp Asn Gly Arg Thr Cys Lys Ala Gly
1               5                   10                  15

<210> SEQ ID NO 116
<211> LENGTH: 19
<212> TYPE: PRT
<213> ORGANISM: Artificial
<220> FEATURE:
<223> OTHER INFORMATION: LRP 5/6 Peptides

<400> SEQUENCE: 116

Glu Val Leu Leu Leu Ala Arg Arg Thr Asp Leu Arg Arg Ile Ser Leu
1               5                   10                  15

Asp Thr Pro

<210> SEQ ID NO 117
<211> LENGTH: 14
<212> TYPE: PRT
<213> ORGANISM: Artificial
<220> FEATURE:
<223> OTHER INFORMATION: LRP 5/6 Peptides

<400> SEQUENCE: 117

Tyr Trp Thr Asp Asp Glu Val Arg Ala Ile Arg Arg Ala Tyr
1               5                   10

<210> SEQ ID NO 118
<211> LENGTH: 10
<212> TYPE: PRT
<213> ORGANISM: Artificial
<220> FEATURE:
<223> OTHER INFORMATION: LRP 5/6 Peptides

<400> SEQUENCE: 118

Val Asn Thr Glu Ile Asn Asp Pro Asp Gly
1               5                   10

<210> SEQ ID NO 119
<211> LENGTH: 29
<212> TYPE: PRT
```

<213> ORGANISM: Artificial
<220> FEATURE:
<223> OTHER INFORMATION: LRP 5/6 Peptides

<400> SEQUENCE: 119

Tyr Trp Thr Asp Thr Gly Thr Asp Arg Ile Glu Val Thr Arg Leu Asn
1               5                   10                  15

Gly Thr Ser Arg Lys Ile Leu Val Ser Glu Asp Leu Asp
            20                  25

<210> SEQ ID NO 120
<211> LENGTH: 20
<212> TYPE: PRT
<213> ORGANISM: LRP 5/6 Peptides

<400> SEQUENCE: 120

Thr Asp Trp Gln Arg Arg Ser Ile Glu Arg Val His Lys Val Lys Ala
1               5                   10                  15

Ser Arg Asp Val
            20

<210> SEQ ID NO 121
<211> LENGTH: 11
<212> TYPE: PRT
<213> ORGANISM: Artificial
<220> FEATURE:
<223> OTHER INFORMATION: LRP 5/6 Peptides

<400> SEQUENCE: 121

Asn Val Asp Gly Thr Lys Arg Arg Thr Leu Leu
1               5                   10

<210> SEQ ID NO 122
<211> LENGTH: 109
<212> TYPE: PRT
<213> ORGANISM: Artificial
<220> FEATURE:
<223> OTHER INFORMATION: LRP 5/6 Peptides

<400> SEQUENCE: 122

Pro Glu Pro Pro Pro Glu Leu Glu Asn Asn Lys Thr Met Asn Arg Ala
1               5                   10                  15

Glu Asn Gly Gly Arg Pro Pro His Pro Phe Glu Thr Lys Asp Val
            20                  25                  30

Ser Glu Tyr Ser Cys Arg Glu Leu His Phe Thr Arg Tyr Val Thr Asp
            35                  40                  45

Gly Pro Cys Arg Ser Ala Lys Pro Val Thr Glu Leu Val Cys Ser Gly
        50                  55                  60

Gln Cys Gly Pro Ala Arg Leu Leu Pro Asn Ala Ile Gly Arg Gly Lys
65                  70                  75                  80

Trp Trp Arg Pro Ser Gly Pro Asp Phe Arg Cys Ile Pro Asp Arg Tyr
                85                  90                  95

Arg Ala Gln Arg Val Gln Leu Leu Cys Pro Gly Gly Glu
                100                 105

<210> SEQ ID NO 123
<211> LENGTH: 56
<212> TYPE: PRT
<213> ORGANISM: Artificial
<220> FEATURE:
<223> OTHER INFORMATION: LRP 5/6 Peptides

<400> SEQUENCE: 123

```
Pro Glu Pro Pro Pro Glu Leu Glu Asn Asn Lys Thr Met Asn Arg Ala
1               5                   10                  15

Glu Asn Gly Gly Arg Pro Pro His His Pro Phe Glu Thr Lys Asp Val
            20                  25                  30

Ser Glu Tyr Ser Cys Arg Glu Leu His Phe Thr Arg Tyr Val Thr Asp
        35                  40                  45

Gly Pro Cys Arg Ser Ala Lys Pro
    50                  55

<210> SEQ ID NO 124
<211> LENGTH: 53
<212> TYPE: PRT
<213> ORGANISM: Artificial
<220> FEATURE:
<223> OTHER INFORMATION: LRP 5/6 Peptides

<400> SEQUENCE: 124

Val Thr Glu Leu Val Cys Ser Gly Gln Cys Gly Pro Ala Arg Leu Leu
1               5                   10                  15

Pro Asn Ala Ile Gly Arg Gly Lys Trp Trp Arg Pro Ser Gly Pro Asp
            20                  25                  30

Phe Arg Cys Ile Pro Asp Arg Tyr Arg Ala Gln Arg Val Gln Leu Leu
        35                  40                  45

Cys Pro Gly Gly Glu
    50

<210> SEQ ID NO 125
<211> LENGTH: 24
<212> TYPE: PRT
<213> ORGANISM: Artificial
<220> FEATURE:
<223> OTHER INFORMATION: LRP 5/6 Peptides

<400> SEQUENCE: 125

Gly Phe Met Tyr Trp Thr Asp Trp Gly Glu Val Pro Lys Ile Glu Arg
1               5                   10                  15

Ala Gly Met Asp Gly Ser Ser Arg
            20

<210> SEQ ID NO 126
<211> LENGTH: 13
<212> TYPE: PRT
<213> ORGANISM: Artificial
<220> FEATURE:
<223> OTHER INFORMATION: LRP 5/6 Peptides

<400> SEQUENCE: 126

Pro Lys Ile Glu Arg Ala Gly Met Asp Gly Ser Ser Arg
1               5                   10

<210> SEQ ID NO 127
<211> LENGTH: 18
<212> TYPE: PRT
<213> ORGANISM: Artificial
<220> FEATURE:
<223> OTHER INFORMATION: LRP 5/6 Peptides

<400> SEQUENCE: 127

Ala Ala Pro Leu Leu Leu Tyr Ala Asn Arg Arg Asp Leu Arg Leu Val
1               5                   10                  15

Asp Ala
```

```
<210> SEQ ID NO 128
<211> LENGTH: 17
<212> TYPE: PRT
<213> ORGANISM: Artificial
<220> FEATURE:
<223> OTHER INFORMATION: LRP 5/6 Peptides

<400> SEQUENCE: 128

Thr Ile Val Val Gly Gly Leu Glu Asp Ala Ala Ala Val Asp Phe Val
1               5                   10                  15

Phe

<210> SEQ ID NO 129
<211> LENGTH: 14
<212> TYPE: PRT
<213> ORGANISM: Artificial
<220> FEATURE:
<223> OTHER INFORMATION: LRP 5/6 Peptides

<400> SEQUENCE: 129

Gly Leu Ile Tyr Trp Ser Asp Val Ser Glu Glu Ala Ile Lys
1               5                   10

<210> SEQ ID NO 130
<211> LENGTH: 40
<212> TYPE: PRT
<213> ORGANISM: Artificial
<220> FEATURE:
<223> OTHER INFORMATION: LRP 5/6 Peptides

<400> SEQUENCE: 130

Ser Val Gln Asn Val Val Ser Gly Leu Leu Ser Pro Asp Gly Leu
1               5                   10                  15

Ala Cys Asp Trp Leu Gly Glu Lys Leu Tyr Trp Thr Asp Ser Glu Thr
                20                  25                  30

Asn Arg Ile Glu Val Ser Asn Leu
        35                  40

<210> SEQ ID NO 131
<211> LENGTH: 19
<212> TYPE: PRT
<213> ORGANISM: Artificial
<220> FEATURE:
<223> OTHER INFORMATION: LRP 5/6 Peptides

<400> SEQUENCE: 131

Gln Asn Val Val Val Ser Gly Leu Leu Ser Pro Asp Gly Leu Ala Cys
1               5                   10                  15

Asp Trp Leu

<210> SEQ ID NO 132
<211> LENGTH: 20
<212> TYPE: PRT
<213> ORGANISM: Artificial
<220> FEATURE:
<223> OTHER INFORMATION: LRP 5/6 Peptides

<400> SEQUENCE: 132

Lys Leu Tyr Trp Thr Asp Ser Glu Thr Asn Arg Ile Glu Val Ser Asn
1               5                   10                  15

Leu Asp Gly Ser
        20
```

```
<210> SEQ ID NO 133
<211> LENGTH: 19
<212> TYPE: PRT
<213> ORGANISM: Artificial
<220> FEATURE:
<223> OTHER INFORMATION: LRP 5/6 Peptides

<400> SEQUENCE: 133

Arg Lys Val Leu Phe Trp Gln Glu Leu Asp Gln Pro Arg Ala Ile Ala
1               5                   10                  15
Leu Asp Pro

<210> SEQ ID NO 134
<211> LENGTH: 20
<212> TYPE: PRT
<213> ORGANISM: Artificial
<220> FEATURE:
<223> OTHER INFORMATION: LRP 5/6 Peptides

<400> SEQUENCE: 134

Met Tyr Trp Thr Asp Trp Gly Glu Val Pro Lys Ile Glu Arg Ala Gly
1               5                   10                  15
Met Asp Gly Ser
            20

<210> SEQ ID NO 135
<211> LENGTH: 8
<212> TYPE: PRT
<213> ORGANISM: Artificial
<220> FEATURE:
<223> OTHER INFORMATION: LRP 5/6 Peptides

<400> SEQUENCE: 135

Ile Tyr Trp Pro Asn Gly Leu Thr
1               5

<210> SEQ ID NO 136
<211> LENGTH: 9
<212> TYPE: PRT
<213> ORGANISM: Artificial
<220> FEATURE:
<223> OTHER INFORMATION: LRP 5/6 Peptides

<400> SEQUENCE: 136

Lys Leu Tyr Trp Ala Asp Ala Lys Leu
1               5

<210> SEQ ID NO 137
<211> LENGTH: 13
<212> TYPE: PRT
<213> ORGANISM: Artificial
<220> FEATURE:
<223> OTHER INFORMATION: LRP 5/6 Peptides

<400> SEQUENCE: 137

Phe Ile His Lys Ser Asn Leu Asp Gly Thr Asn Arg Gln
1               5                   10

<210> SEQ ID NO 138
<211> LENGTH: 14
<212> TYPE: PRT
<213> ORGANISM: Artificial
<220> FEATURE:
<223> OTHER INFORMATION: LRP 5/6 Peptides

<400> SEQUENCE: 138
```

-continued

Val Val Lys Gly Ser Leu Pro His Pro Phe Ala Leu Thr Leu
1               5                   10

<210> SEQ ID NO 139
<211> LENGTH: 21
<212> TYPE: PRT
<213> ORGANISM: Artificial
<220> FEATURE:
<223> OTHER INFORMATION: LRP 5/6 Peptides

<400> SEQUENCE: 139

Asp Thr Leu Tyr Trp Thr Asp Trp Asn Thr His Ser Ile Leu Ala Cys
1               5                   10                  15

Asn Lys Tyr Thr Gly
            20

<210> SEQ ID NO 140
<211> LENGTH: 13
<212> TYPE: PRT
<213> ORGANISM: Artificial
<220> FEATURE:
<223> OTHER INFORMATION: LRP 5/6 Peptides

<400> SEQUENCE: 140

Arg Glu Ile His Ser Asn Ile Phe Ser Pro Met Asp Ile
1               5                   10

<210> SEQ ID NO 141
<211> LENGTH: 21
<212> TYPE: PRT
<213> ORGANISM: Artificial
<220> FEATURE:
<223> OTHER INFORMATION: LRP 5/6 Peptides

<400> SEQUENCE: 141

Ser Asp Arg Asn Asn Arg Val Gln Val Gly Cys Arg Glu Leu Arg Ser
1               5                   10                  15

Thr Lys Tyr Ile Ser
            20

<210> SEQ ID NO 142
<211> LENGTH: 21
<212> TYPE: PRT
<213> ORGANISM: Artificial
<220> FEATURE:
<223> OTHER INFORMATION: LRP 5/6 Peptides

<400> SEQUENCE: 142

Pro Glu Pro Pro Pro Glu Leu Glu Asn Asn Lys Thr Met Asn Arg Ala
1               5                   10                  15

Glu Asn Gly Gly Arg
            20

<210> SEQ ID NO 143
<211> LENGTH: 32
<212> TYPE: PRT
<213> ORGANISM: Artificial
<220> FEATURE:
<223> OTHER INFORMATION: LRP 5/6 Peptides

<400> SEQUENCE: 143

Asn Gly Gly Arg Pro Pro His Pro Phe Glu Thr Lys Asp Val Ser
1               5                   10                  15

Glu Tyr Ser Cys Arg Glu Leu His Phe Thr Arg Tyr Val Thr Asp Gly
                20                  25                  30

<210> SEQ ID NO 144
<211> LENGTH: 8
<212> TYPE: PRT
<213> ORGANISM: Artificial
<220> FEATURE:
<223> OTHER INFORMATION: LRP 5/6 Peptides

<400> SEQUENCE: 144

Asn Asn Lys Thr Met Asn Arg Ala
1               5

<210> SEQ ID NO 145
<211> LENGTH: 5
<212> TYPE: PRT
<213> ORGANISM: Artificial
<220> FEATURE:
<223> OTHER INFORMATION: LRP 5/6 Peptides

<400> SEQUENCE: 145

Thr Met Asn Arg Ala
1               5

<210> SEQ ID NO 146
<211> LENGTH: 8
<212> TYPE: PRT
<213> ORGANISM: Artificial
<220> FEATURE:
<223> OTHER INFORMATION: LRP 5/6 Peptides

<400> SEQUENCE: 146

Gly Gly Arg Pro Pro His His Pro
1               5

<210> SEQ ID NO 147
<211> LENGTH: 9
<212> TYPE: PRT
<213> ORGANISM: Artificial
<220> FEATURE:
<223> OTHER INFORMATION: LRP 5/6 Peptides

<400> SEQUENCE: 147

His His Pro Phe Glu Thr Lys Asp Val
1               5

<210> SEQ ID NO 148
<211> LENGTH: 10
<212> TYPE: PRT
<213> ORGANISM: Artificial
<220> FEATURE:
<223> OTHER INFORMATION: LRP 5/6 Peptides

<400> SEQUENCE: 148

Asp Val Ser Glu Tyr Ser Cys Arg Glu Leu
1               5                   10

<210> SEQ ID NO 149
<211> LENGTH: 17
<212> TYPE: PRT
<213> ORGANISM: Artificial
<220> FEATURE:
<223> OTHER INFORMATION: LRP 5/6 Peptides

<400> SEQUENCE: 149

Cys Arg Glu Leu His Phe Thr Arg Tyr Val Thr Asp Gly Pro Cys Arg
1               5                   10                  15

Ser

<210> SEQ ID NO 150
<211> LENGTH: 7
<212> TYPE: PRT
<213> ORGANISM: Artificial
<220> FEATURE:
<223> OTHER INFORMATION: LRP 5/6 Peptides

<400> SEQUENCE: 150

Thr Arg Tyr Val Thr Asp Gly
1               5

<210> SEQ ID NO 151
<211> LENGTH: 5
<212> TYPE: PRT
<213> ORGANISM: Artificial
<220> FEATURE:
<223> OTHER INFORMATION: LRP 5/6 Peptides

<400> SEQUENCE: 151

Tyr Val Thr Asp Gly
1               5

<210> SEQ ID NO 152
<211> LENGTH: 6
<212> TYPE: PRT
<213> ORGANISM: Artificial
<220> FEATURE:
<223> OTHER INFORMATION: LRP 5/6 Peptides

<400> SEQUENCE: 152

Asp Gly Pro Cys Arg Ser
1               5

<210> SEQ ID NO 153
<211> LENGTH: 12
<212> TYPE: PRT
<213> ORGANISM: Artificial
<220> FEATURE:
<223> OTHER INFORMATION: LRP 5/6 Peptides

<400> SEQUENCE: 153

Leu Pro Asn Ala Ile Gly Arg Gly Lys Trp Trp Arg
1               5                   10

<210> SEQ ID NO 154
<211> LENGTH: 8
<212> TYPE: PRT
<213> ORGANISM: Artificial
<220> FEATURE:
<223> OTHER INFORMATION: LRP 5/6 Peptides

<400> SEQUENCE: 154

Pro Asn Trp Ile Gly Gly Gly Tyr
1               5

<210> SEQ ID NO 155
<211> LENGTH: 11
<212> TYPE: PRT
<213> ORGANISM: Artificial
<220> FEATURE:
<223> OTHER INFORMATION: LRP 5/6 Peptides

<400> SEQUENCE: 155

Thr Leu Asn Gln Ala Arg Asn Gly Gly Arg His
1               5                   10

```
<210> SEQ ID NO 156
<211> LENGTH: 5
<212> TYPE: PRT
<213> ORGANISM: Artificial
<220> FEATURE:
<223> OTHER INFORMATION: LRP 5/6 Peptides

<400> SEQUENCE: 156

Gly Leu Asp Arg Asn
1               5

<210> SEQ ID NO 157
<211> LENGTH: 13
<212> TYPE: PRT
<213> ORGANISM: Artificial
<220> FEATURE:
<223> OTHER INFORMATION: LRP 5/6 Peptides

<400> SEQUENCE: 157

Cys Arg Glu Leu Arg Ser Thr Lys Tyr Ile Ser Asp Gly
1               5                   10

<210> SEQ ID NO 158
<211> LENGTH: 15
<212> TYPE: PRT
<213> ORGANISM: Artificial
<220> FEATURE:
<223> OTHER INFORMATION: LRP 5/6 Peptides

<400> SEQUENCE: 158

Leu Phe Ala Asn Arg Arg Asp Val Arg Leu Val Asp Ala Gly Gly
1               5                   10                  15

<210> SEQ ID NO 159
<211> LENGTH: 8
<212> TYPE: PRT
<213> ORGANISM: Artificial
<220> FEATURE:
<223> OTHER INFORMATION: LRP 5/6 Peptides

<400> SEQUENCE: 159

Tyr Trp Thr Asp Val Ser Glu Glu
1               5

<210> SEQ ID NO 160
<211> LENGTH: 19
<212> TYPE: PRT
<213> ORGANISM: Artificial
<220> FEATURE:
<223> OTHER INFORMATION: LRP 5/6 Peptides

<400> SEQUENCE: 160

Lys Leu Tyr Trp Thr Asp Ser Glu Thr Asn Arg Ile Glu Val Ala Asn
1               5                   10                  15

Leu Asn Gly

<210> SEQ ID NO 161
<211> LENGTH: 7
<212> TYPE: PRT
<213> ORGANISM: Artificial
<220> FEATURE:
<223> OTHER INFORMATION: LRP 5/6 Peptides

<400> SEQUENCE: 161

Leu Phe Trp Gln Asp Leu Asp
```

<210> SEQ ID NO 162
<211> LENGTH: 23
<212> TYPE: PRT
<213> ORGANISM: Artificial
<220> FEATURE:
<223> OTHER INFORMATION: LRP 5/6 Peptides

<400> SEQUENCE: 162

Thr Asp Trp Gly Glu Thr Pro Arg Ile Glu Arg Ala Gly Met Asp Gly
1               5                   10                  15

Ser Thr Arg Lys Ile Ile Val
            20

<210> SEQ ID NO 163
<211> LENGTH: 11
<212> TYPE: PRT
<213> ORGANISM: Artificial
<220> FEATURE:
<223> OTHER INFORMATION: LRP 5/6 Peptides

<400> SEQUENCE: 163

His Ala Cys Asn Lys Arg Thr Gly Gly Lys Arg
1               5                   10

<210> SEQ ID NO 164
<211> LENGTH: 15
<212> TYPE: PRT
<213> ORGANISM: Artificial
<220> FEATURE:
<223> OTHER INFORMATION: LRP 5/6 Peptides

<400> SEQUENCE: 164

Thr Gly Val Gln Leu Gln Asp Asn Gly Arg Thr Cys Lys Ala Gly
1               5                   10                  15

<210> SEQ ID NO 165
<211> LENGTH: 19
<212> TYPE: PRT
<213> ORGANISM: Artificial
<220> FEATURE:
<223> OTHER INFORMATION: LRP 5/6 Peptides

<400> SEQUENCE: 165

Glu Val Leu Leu Leu Ala Arg Arg Thr Asp Leu Arg Arg Ile Ser Leu
1               5                   10                  15

Asp Thr Pro

<210> SEQ ID NO 166
<211> LENGTH: 14
<212> TYPE: PRT
<213> ORGANISM: Artificial
<220> FEATURE:
<223> OTHER INFORMATION: LRP 5/6 Peptides

<400> SEQUENCE: 166

Tyr Trp Thr Asp Asp Glu Val Arg Ala Ile Arg Arg Ala Tyr
1               5                   10

<210> SEQ ID NO 167
<211> LENGTH: 10
<212> TYPE: PRT
<213> ORGANISM: Artificial
<220> FEATURE:
<223> OTHER INFORMATION: LRP 5/6 Peptides

<400> SEQUENCE: 167

Val Asn Thr Glu Ile Asn Asp Pro Asp Gly
1               5                   10

<210> SEQ ID NO 168
<211> LENGTH: 29
<212> TYPE: PRT
<213> ORGANISM: Artificial
<220> FEATURE:
<223> OTHER INFORMATION: LRP 5/6 Peptides

<400> SEQUENCE: 168

Tyr Trp Thr Asp Thr Gly Thr Asp Arg Ile Glu Val Thr Arg Leu Asn
1               5                   10                  15

Gly Thr Ser Arg Lys Ile Leu Val Ser Glu Asp Leu Asp
            20                  25

<210> SEQ ID NO 169
<211> LENGTH: 20
<212> TYPE: PRT
<213> ORGANISM: Artificial
<220> FEATURE:
<223> OTHER INFORMATION: LRP 5/6 Peptides

<400> SEQUENCE: 169

Thr Asp Trp Gln Arg Arg Ser Ile Glu Arg Val His Lys Val Lys Ala
1               5                   10                  15

Ser Arg Asp Val
            20

<210> SEQ ID NO 170
<211> LENGTH: 11
<212> TYPE: PRT
<213> ORGANISM: Artificial
<220> FEATURE:
<223> OTHER INFORMATION: LRP 5/6 Peptides

<400> SEQUENCE: 170

Asn Val Asp Gly Thr Lys Arg Arg Thr Leu Leu
1               5                   10

<210> SEQ ID NO 171
<211> LENGTH: 109
<212> TYPE: PRT
<213> ORGANISM: Artificial
<220> FEATURE:
<223> OTHER INFORMATION: LRP 5/6 Peptides

<400> SEQUENCE: 171

Pro Glu Pro Pro Pro Glu Leu Glu Asn Asn Lys Thr Met Asn Arg Ala
1               5                   10                  15

Glu Asn Gly Gly Arg Pro Pro His His Pro Phe Glu Thr Lys Asp Val
            20                  25                  30

Ser Glu Tyr Ser Cys Arg Glu Leu His Phe Thr Arg Tyr Val Thr Asp
        35                  40                  45

Gly Pro Cys Arg Ser Ala Lys Pro Val Thr Glu Leu Val Cys Ser Gly
    50                  55                  60

Gln Cys Gly Pro Ala Arg Leu Leu Pro Asn Ala Ile Gly Arg Gly Lys
65                  70                  75                  80

Trp Trp Arg Pro Ser Gly Pro Asp Phe Arg Cys Ile Pro Asp Arg Tyr
                85                  90                  95

```
Arg Ala Gln Arg Val Gln Leu Leu Cys Pro Gly Gly Glu
            100                 105

<210> SEQ ID NO 172
<211> LENGTH: 56
<212> TYPE: PRT
<213> ORGANISM: Artificial
<220> FEATURE:
<223> OTHER INFORMATION: LRP 5/6 Peptides

<400> SEQUENCE: 172

Pro Glu Pro Pro Pro Glu Leu Glu Asn Asn Lys Thr Met Asn Arg Ala
1               5                   10                  15

Glu Asn Gly Gly Arg Pro Pro His His Pro Phe Glu Thr Lys Asp Val
            20                  25                  30

Ser Glu Tyr Ser Cys Arg Glu Leu His Phe Thr Arg Tyr Val Thr Asp
        35                  40                  45

Gly Pro Cys Arg Ser Ala Lys Pro
    50                  55

<210> SEQ ID NO 173
<211> LENGTH: 53
<212> TYPE: PRT
<213> ORGANISM: Artificial
<220> FEATURE:
<223> OTHER INFORMATION: LRP 5/6 Peptides

<400> SEQUENCE: 173

Val Thr Glu Leu Val Cys Ser Gly Gln Cys Gly Pro Ala Arg Leu Leu
1               5                   10                  15

Pro Asn Ala Ile Gly Arg Gly Lys Trp Trp Arg Pro Ser Gly Pro Asp
            20                  25                  30

Phe Arg Cys Ile Pro Asp Arg Tyr Arg Ala Gln Arg Val Gln Leu Leu
        35                  40                  45

Cys Pro Gly Gly Glu
    50

<210> SEQ ID NO 174
<211> LENGTH: 18
<212> TYPE: PRT
<213> ORGANISM: Artificial
<220> FEATURE:
<223> OTHER INFORMATION: LRP 5/6 Peptides

<400> SEQUENCE: 174

Ala Ala Pro Leu Leu Leu Tyr Ala Asn Arg Arg Asp Leu Arg Leu Val
1               5                   10                  15

Asp Ala

<210> SEQ ID NO 175
<211> LENGTH: 17
<212> TYPE: PRT
<213> ORGANISM: Artificial
<220> FEATURE:
<223> OTHER INFORMATION: LRP 5/6 Peptides

<400> SEQUENCE: 175

Thr Ile Val Val Gly Gly Leu Glu Asp Ala Ala Ala Val Asp Phe Val
1               5                   10                  15

Phe

<210> SEQ ID NO 176
```

```
<211> LENGTH: 14
<212> TYPE: PRT
<213> ORGANISM: Artificial
<220> FEATURE:
<223> OTHER INFORMATION: LRP 5/6 Peptides

<400> SEQUENCE: 176

Gly Leu Ile Tyr Trp Ser Asp Val Ser Glu Glu Ala Ile Lys
1               5                   10

<210> SEQ ID NO 177
<211> LENGTH: 40
<212> TYPE: PRT
<213> ORGANISM: Artificial
<220> FEATURE:
<223> OTHER INFORMATION: LRP 5/6 Peptides

<400> SEQUENCE: 177

Ser Val Gln Asn Val Val Ser Gly Leu Leu Ser Pro Asp Gly Leu
1               5                   10                  15

Ala Cys Asp Trp Leu Gly Glu Lys Leu Tyr Trp Thr Asp Ser Glu Thr
            20                  25                  30

Asn Arg Ile Glu Val Ser Asn Leu
        35                  40

<210> SEQ ID NO 178
<211> LENGTH: 19
<212> TYPE: PRT
<213> ORGANISM: Artificial
<220> FEATURE:
<223> OTHER INFORMATION: LRP 5/6 Peptides

<400> SEQUENCE: 178

Gln Asn Val Val Val Ser Gly Leu Leu Ser Pro Asp Gly Leu Ala Cys
1               5                   10                  15

Asp Trp Leu

<210> SEQ ID NO 179
<211> LENGTH: 20
<212> TYPE: PRT
<213> ORGANISM: Artificial
<220> FEATURE:
<223> OTHER INFORMATION: LRP 5/6 Peptides

<400> SEQUENCE: 179

Lys Leu Tyr Trp Thr Asp Ser Glu Thr Asn Arg Ile Glu Val Ser Asn
1               5                   10                  15

Leu Asp Gly Ser
            20

<210> SEQ ID NO 180
<211> LENGTH: 19
<212> TYPE: PRT
<213> ORGANISM: Artificial
<220> FEATURE:
<223> OTHER INFORMATION: LRP 5/6 Peptides

<400> SEQUENCE: 180

Arg Lys Val Leu Phe Trp Gln Glu Leu Asp Gln Pro Arg Ala Ile Ala
1               5                   10                  15

Leu Asp Pro

<210> SEQ ID NO 181
<211> LENGTH: 20
```

```
<212> TYPE: PRT
<213> ORGANISM: Artificial
<220> FEATURE:
<223> OTHER INFORMATION: LRP 5/6 Peptides

<400> SEQUENCE: 181

Met Tyr Trp Thr Asp Trp Gly Glu Val Pro Lys Ile Glu Arg Ala Gly
1               5                   10                  15

Met Asp Gly Ser
            20

<210> SEQ ID NO 182
<211> LENGTH: 8
<212> TYPE: PRT
<213> ORGANISM: Artificial
<220> FEATURE:
<223> OTHER INFORMATION: LRP 5/6 Peptides

<400> SEQUENCE: 182

Ile Tyr Trp Pro Asn Gly Leu Thr
1               5

<210> SEQ ID NO 183
<211> LENGTH: 9
<212> TYPE: PRT
<213> ORGANISM: Artificial
<220> FEATURE:
<223> OTHER INFORMATION: LRP 5/6 Peptides

<400> SEQUENCE: 183

Lys Leu Tyr Trp Ala Asp Ala Lys Leu
1               5

<210> SEQ ID NO 184
<211> LENGTH: 13
<212> TYPE: PRT
<213> ORGANISM: Artificial
<220> FEATURE:
<223> OTHER INFORMATION: LRP 5/6 Peptides

<400> SEQUENCE: 184

Phe Ile His Lys Ser Asn Leu Asp Gly Thr Asn Arg Gln
1               5                   10

<210> SEQ ID NO 185
<211> LENGTH: 14
<212> TYPE: PRT
<213> ORGANISM: Artificial
<220> FEATURE:
<223> OTHER INFORMATION: LRP 5/6 Peptides

<400> SEQUENCE: 185

Val Val Lys Gly Ser Leu Pro His Pro Phe Ala Leu Thr Leu
1               5                   10

<210> SEQ ID NO 186
<211> LENGTH: 21
<212> TYPE: PRT
<213> ORGANISM: Artificial
<220> FEATURE:
<223> OTHER INFORMATION: LRP 5/6 Peptides

<400> SEQUENCE: 186

Asp Thr Leu Tyr Trp Thr Asp Trp Asn Thr His Ser Ile Leu Ala Cys
1               5                   10                  15

Asn Lys Tyr Thr Gly
```

-continued

<210> SEQ ID NO 187
<211> LENGTH: 13
<212> TYPE: PRT
<213> ORGANISM: Artificial
<220> FEATURE:
<223> OTHER INFORMATION: LRP 5/6 Peptides

<400> SEQUENCE: 187

Arg Glu Ile His Ser Asn Ile Phe Ser Pro Met Asp Ile
1               5                   10

<210> SEQ ID NO 188
<211> LENGTH: 10
<212> TYPE: PRT
<213> ORGANISM: Artificial
<220> FEATURE:
<223> OTHER INFORMATION: LRP 5/6 Peptides

<400> SEQUENCE: 188

Asp Asn Gly Gly Cys Ser His Leu Cys Leu
1               5                   10

<210> SEQ ID NO 189
<211> LENGTH: 11
<212> TYPE: PRT
<213> ORGANISM: Artificial
<220> FEATURE:
<223> OTHER INFORMATION: LRP 5/6 Peptides

<400> SEQUENCE: 189

Pro Phe Tyr Gln Cys Ala Cys Pro Thr Gly Val
1               5                   10

<210> SEQ ID NO 190
<211> LENGTH: 25
<212> TYPE: PRT
<213> ORGANISM: Artificial
<220> FEATURE:
<223> OTHER INFORMATION: LRP 5/6 Peptides

<400> SEQUENCE: 190

Leu Leu Leu Ala Arg Arg Thr Asp Leu Arg Arg Ile Ser Leu Asp Thr
1               5                   10                  15

Pro Asp Phe Thr Asp Ile Val Leu Gln
            20                  25

<210> SEQ ID NO 191
<211> LENGTH: 12
<212> TYPE: PRT
<213> ORGANISM: Artificial
<220> FEATURE:
<223> OTHER INFORMATION: LRP 5/6 Peptides

<400> SEQUENCE: 191

Asp Ile Arg His Ala Ile Ala Ile Asp Tyr Asp Pro
1               5                   10

<210> SEQ ID NO 192
<211> LENGTH: 16
<212> TYPE: PRT
<213> ORGANISM: Artificial
<220> FEATURE:
<223> OTHER INFORMATION: LRP 5/6 Peptides

<400> SEQUENCE: 192

Glu Gly Tyr Ile Tyr Trp Thr Asp Asp Glu Val Arg Ala Ile Arg Arg
1               5                   10                  15

<210> SEQ ID NO 193
<211> LENGTH: 31
<212> TYPE: PRT
<213> ORGANISM: Artificial
<220> FEATURE:
<223> OTHER INFORMATION: LRP 5/6 Peptides

<400> SEQUENCE: 193

Pro Asp Gly Ile Ala Val Asp Trp Val Ala Arg Asn Leu Tyr Trp Thr
1               5                   10                  15

Asp Thr Gly Thr Asp Arg Ile Glu Val Thr Arg Leu Asn Gly Thr
            20                  25                  30

<210> SEQ ID NO 194
<211> LENGTH: 15
<212> TYPE: PRT
<213> ORGANISM: Artificial
<220> FEATURE:
<223> OTHER INFORMATION: LRP 5/6 Peptides

<400> SEQUENCE: 194

Arg Lys Ile Leu Ile Ser Glu Asp Leu Glu Glu Pro Arg Ala Ile
1               5                   10                  15

<210> SEQ ID NO 195
<211> LENGTH: 8
<212> TYPE: PRT
<213> ORGANISM: Artificial
<220> FEATURE:
<223> OTHER INFORMATION: LRP 5/6 Peptides

<400> SEQUENCE: 195

Met Tyr Trp Thr Asp Trp Gly Glu
1               5

<210> SEQ ID NO 196
<211> LENGTH: 10
<212> TYPE: PRT
<213> ORGANISM: Artificial
<220> FEATURE:
<223> OTHER INFORMATION: LRP 5/6 Peptides

<400> SEQUENCE: 196

Pro Lys Ile Glu Arg Ala Ala Leu Asp Gly
1               5                   10

<210> SEQ ID NO 197
<211> LENGTH: 16
<212> TYPE: PRT
<213> ORGANISM: Artificial
<220> FEATURE:
<223> OTHER INFORMATION: LRP 5/6 Peptides

<400> SEQUENCE: 197

Val Leu Val Asn Thr Ser Leu Gly Trp Pro Asn Gly Leu Ala Leu Asp
1               5                   10                  15

<210> SEQ ID NO 198
<211> LENGTH: 12
<212> TYPE: PRT
<213> ORGANISM: Artificial
<220> FEATURE:
<223> OTHER INFORMATION: LRP 5/6 Peptides

```
<400> SEQUENCE: 198

Tyr Trp Gly Asp Ala Lys Thr Asp Lys Ile Glu Val
1               5                   10

<210> SEQ ID NO 199
<211> LENGTH: 32
<212> TYPE: PRT
<213> ORGANISM: Artificial
<220> FEATURE:
<223> OTHER INFORMATION: LRP 5/6 Peptides

<400> SEQUENCE: 199

Glu Asp Lys Ile Pro His Ile Phe Gly Phe Thr Leu Leu Gly Asp Tyr
1               5                   10                  15

Val Tyr Trp Thr Asp Trp Gln Arg Arg Ser Ile Glu Arg Val His Lys
            20                  25                  30

<210> SEQ ID NO 200
<211> LENGTH: 24
<212> TYPE: PRT
<213> ORGANISM: Artificial
<220> FEATURE:
<223> OTHER INFORMATION: LRP 5/6 Peptides

<400> SEQUENCE: 200

Gly Phe Met Tyr Trp Thr Asp Trp Gly Glu Val Pro Lys Ile Glu Arg
1               5                   10                  15

Ala Gly Met Asp Gly Ser Ser Arg
            20

<210> SEQ ID NO 201
<211> LENGTH: 13
<212> TYPE: PRT
<213> ORGANISM: Artificial
<220> FEATURE:
<223> OTHER INFORMATION: LRP 5/6 Peptides

<400> SEQUENCE: 201

Pro Lys Ile Glu Arg Ala Gly Met Asp Gly Ser Ser Arg
1               5                   10

<210> SEQ ID NO 202
<211> LENGTH: 10
<212> TYPE: PRT
<213> ORGANISM: Artificial
<220> FEATURE:
<223> OTHER INFORMATION: LRP 5/6 Peptides

<400> SEQUENCE: 202

Asp Asn Gly Gly Cys Ser His Leu Cys Leu
1               5                   10

<210> SEQ ID NO 203
<211> LENGTH: 11
<212> TYPE: PRT
<213> ORGANISM: Artificial
<220> FEATURE:
<223> OTHER INFORMATION: LRP 5/6 Peptides

<400> SEQUENCE: 203

Pro Phe Tyr Gln Cys Ala Cys Pro Thr Gly Val
1               5                   10

<210> SEQ ID NO 204
```

```
<211> LENGTH: 25
<212> TYPE: PRT
<213> ORGANISM: Artificial
<220> FEATURE:
<223> OTHER INFORMATION: LRP 5/6 Peptides

<400> SEQUENCE: 204

Leu Leu Leu Ala Arg Arg Thr Asp Leu Arg Arg Ile Ser Leu Asp Thr
1               5                   10                  15

Pro Asp Phe Thr Asp Ile Val Leu Gln
            20                  25

<210> SEQ ID NO 205
<211> LENGTH: 12
<212> TYPE: PRT
<213> ORGANISM: Artificial
<220> FEATURE:
<223> OTHER INFORMATION: LRP 5/6 Peptides

<400> SEQUENCE: 205

Asp Ile Arg His Ala Ile Ala Ile Asp Tyr Asp Pro
1               5                   10

<210> SEQ ID NO 206
<211> LENGTH: 16
<212> TYPE: PRT
<213> ORGANISM: Artificial
<220> FEATURE:
<223> OTHER INFORMATION: LRP 5/6 Peptides

<400> SEQUENCE: 206

Glu Gly Tyr Ile Tyr Trp Thr Asp Asp Glu Val Arg Ala Ile Arg Arg
1               5                   10                  15

<210> SEQ ID NO 207
<211> LENGTH: 31
<212> TYPE: PRT
<213> ORGANISM: Artificial
<220> FEATURE:
<223> OTHER INFORMATION: LRP 5/6 Peptides

<400> SEQUENCE: 207

Pro Asp Gly Ile Ala Val Asp Trp Val Ala Arg Asn Leu Tyr Trp Thr
1               5                   10                  15

Asp Thr Gly Thr Asp Arg Ile Glu Val Thr Arg Leu Asn Gly Thr
            20                  25                  30

<210> SEQ ID NO 208
<211> LENGTH: 15
<212> TYPE: PRT
<213> ORGANISM: Artificial
<220> FEATURE:
<223> OTHER INFORMATION: LRP 5/6 Peptides

<400> SEQUENCE: 208

Arg Lys Ile Leu Ile Ser Glu Asp Leu Glu Glu Pro Arg Ala Ile
1               5                   10                  15

<210> SEQ ID NO 209
<211> LENGTH: 8
<212> TYPE: PRT
<213> ORGANISM: Artificial
<220> FEATURE:
<223> OTHER INFORMATION: LRP 5/6 Peptides

<400> SEQUENCE: 209
```

```
Met Tyr Trp Thr Asp Trp Gly Glu
1               5
```

<210> SEQ ID NO 210
<211> LENGTH: 10
<212> TYPE: PRT
<213> ORGANISM: Artificial
<220> FEATURE:
<223> OTHER INFORMATION: LRP 5/6 Peptides

<400> SEQUENCE: 210

```
Pro Lys Ile Glu Arg Ala Ala Leu Asp Gly
1               5                   10
```

<210> SEQ ID NO 211
<211> LENGTH: 16
<212> TYPE: PRT
<213> ORGANISM: Artificial
<220> FEATURE:
<223> OTHER INFORMATION: LRP 5/6 Peptides

<400> SEQUENCE: 211

```
Val Leu Val Asn Thr Ser Leu Gly Trp Pro Asn Gly Leu Ala Leu Asp
1               5                   10                  15
```

<210> SEQ ID NO 212
<211> LENGTH: 12
<212> TYPE: PRT
<213> ORGANISM: Artificial
<220> FEATURE:
<223> OTHER INFORMATION: LRP 5/6 Peptides

<400> SEQUENCE: 212

```
Tyr Trp Gly Asp Ala Lys Thr Asp Lys Ile Glu Val
1               5                   10
```

<210> SEQ ID NO 213
<211> LENGTH: 32
<212> TYPE: PRT
<213> ORGANISM: Artificial
<220> FEATURE:
<223> OTHER INFORMATION: LRP 5/6 Peptides

<400> SEQUENCE: 213

```
Glu Asp Lys Ile Pro His Ile Phe Gly Phe Thr Leu Leu Gly Asp Tyr
1               5                   10                  15

Val Tyr Trp Thr Asp Trp Gln Arg Arg Ser Ile Glu Arg Val His Lys
                20                  25                  30
```

<210> SEQ ID NO 214
<211> LENGTH: 21
<212> TYPE: PRT
<213> ORGANISM: Artificial
<220> FEATURE:
<223> OTHER INFORMATION: LRP 5/6 Peptides

<400> SEQUENCE: 214

```
Ser Asp Arg Asn Asn Arg Val Gln Val Gly Cys Arg Glu Leu Arg Ser
1               5                   10                  15

Thr Lys Tyr Ile Ser
                20
```

<210> SEQ ID NO 215
<211> LENGTH: 621
<212> TYPE: DNA
<213> ORGANISM: Human

<400> SEQUENCE: 215

```
atgcttcctc ctgccattca tctctctctc attcccctgc tctgcatcct gatgaaaaac        60
tgtttggctt ttaaaaatga tgccacagaa atcctttatt cacatgtggt taaacctgtt       120
tcagcacacc ccagcagcaa cagcaccttg aatcaagcca ggaatggagg caggcacttc       180
agtagcacgg gactggatcg aaatagtcga gttcaagtgg gctgcaggga actgcggtcc       240
accaaataca tctcggatgg ccagtgcacc agcatcagcc ctctgaagga gctggtgtgc       300
gcgggtgagt gcttgcccct gccagtgctt cccaactgga tcggaggagg ctacggaaca       360
aagtactgga gccggagggg ctcccaggag tggcggtgtg tcaacgacaa gacgcgcacc       420
cagagaatcc agctgcagtg tcaggacggc agcacacgca cctacaaaat caccgtggtc       480
acagcgtgca gtgcaagag gtacacccgg cagcacaacg agtccagcca caactttgaa       540
agcgtgtctc ccgccaagcc cgcccagcac acagagagc ggaagagagc cagcaaatcc       600
agcaagcaca gtctgagcta g                                                  621
```

<210> SEQ ID NO 216
<211> LENGTH: 206
<212> TYPE: PRT
<213> ORGANISM: Mouse
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid

<400> SEQUENCE: 216

```
Met Leu Pro Pro Ala Ile His Leu Ser Leu Ile Pro Leu Leu Cys Ile
 1               5                  10                  15

Leu Met Arg Asn Cys Leu Ala Phe Lys Asn Asp Ala Thr Glu Ile Leu
            20                  25                  30

Tyr Ser His Val Val Lys Pro Val Pro Ala His Pro Ser Ser Asn Ser
        35                  40                  45

Thr Leu Asn Gln Ala Arg Asn Gly Gly Arg His Phe Ser Ser Thr Gly
    50                  55                  60

Leu Asp Arg Asn Ser Arg Val Gln Val Gly Cys Arg Glu Leu Arg Ser
65                  70                  75                  80

Thr Lys Tyr Ile Ser Asp Gly Gln Cys Thr Ser Ile Ser Pro Xaa Lys
                85                  90                  95

Glu Leu Val Cys Ala Gly Glu Cys Leu Pro Leu Pro Val Leu Pro Asn
            100                 105                 110

Trp Ile Gly Gly Gly Tyr Gly Thr Lys Tyr Trp Ser Arg Arg Ser Xaa
        115                 120                 125

Gln Glu Trp Arg Cys Val Asn Asp Lys Thr Arg Thr Gln Arg Ile Gln
    130                 135                 140

Leu Gln Cys Gln Asp Gly Ser Thr Arg Thr Tyr Lys Ile Thr Val Val
145                 150                 155                 160

Thr Ala Cys Lys Cys Lys Arg Tyr Thr Arg Gln His Asn Glu Ser Ser
                165                 170                 175

His Asn Phe Glu Ser Val Ser Pro Ala Lys Pro Ala Gln His His Arg
            180                 185                 190

Glu Arg Lys Arg Ala Ser Lys Ser Lys His Ser Leu Ser
        195                 200                 205
```

```
<210> SEQ ID NO 217
<211> LENGTH: 168
<212> TYPE: PRT
<213> ORGANISM: Human

<400> SEQUENCE: 217

Met Gln Leu Pro Leu Ala Leu Cys Leu Val Cys Leu Leu Val His Thr
1               5                   10                  15

Ala Phe Arg Val Val Glu Gly Gln Gly Trp Gln Ala Phe Lys Asn Asp
            20                  25                  30

Ala Thr Glu Ile Ile Pro Glu Leu Gly Glu Tyr Pro Glu Pro Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys
                165
```

ANTIBODY THAT BINDS MURINE WISE PROTEIN

The present application claims benefit to and is a continuation application of U.S. patent application Ser. No. 13/950,553, which was filed on Jul. 25, 2013, which is now abandoned. The '553 application claims benefit to and is a continuation application of U.S. patent application Ser. No. 13/030,863, which was filed on Feb. 18, 2011, which is now U.S. Pat. No. 8,519,105. The '863 application claims benefit to and is a divisional application of U.S. patent application Ser. No. 12/459,764, which was filed on Jul. 6, 2009, which is now U.S. Pat. No. 7,914,786. The '764 application claims benefit to and is a divisional application of U.S. patent application Ser. No. 11/613,658, which was filed on Dec. 20, 2006, which is now U.S. Pat. No. 7,585,501. The '658 application claims benefit to and is a continuation-in-part application of U.S. patent application Ser. No. 11/508,701, which was filed on Aug. 23, 2006, which is now U.S. Pat. No. 7,893,218. The '701 application claims benefit to U.S. Provisional Patent Application Ser. No. 60/710,803, filed Aug. 23, 2005. The '701 application also claims benefit to and is a continuation-in-part of U.S. patent application Ser. No. 10/464,368, which was filed on Jun. 16, 2003, now abandoned. The '368 application claims benefit to U.S. Provisional Patent Application Ser. No. 60/388,970, filed Jun. 14, 2002. The contents of each application identified above are incorporated by reference in their entirety as if recited in full herein.

INCORPORATION BY REFERENCE OF SEQUENCE LISTING

This application contains references to amino acids and/or nucleic acid sequences that have been filed concurrently herewith as sequence listing text file "0356783con_sequence_listing.txt", file size of 225 KB, created on Dec. 8, 2014. The aforementioned sequence listing is hereby incorporated by reference in its entirety pursuant to 37 C.F.R. § 1.52(e)(5).

BACKGROUND OF INVENTION

A. Field of the Invention

The present invention relates to compositions and methods for the prevention and treatment of renal damage. In particular, the invention relates to administration of novel therapeutics to subjects in order to prevent or treat renal degeneration or damage. These novel therapeutics include antibodies, peptides, and small molecules based upon the WISE/SOST family of proteins.

B. Background of the Invention

The mammalian renal system serves primary roles both in the removal of catabolic waste products from the bloodstream and in the maintenance of fluid and electrolyte balances in the body. Renal failures are, therefore, life-threatening conditions in which the build-up of catabolites and other toxins, and/or the development of significant imbalances in electrolytes or fluids, may lead to the failure of other major organs systems and death. Chronic renal failure is a debilitating and life-threatening disease for which no adequate treatment exists.

Tubular damage and interstitial fibrosis are the final common pathways leading to end stage renal disease. Irrespective of the nature of the initial renal injury, the degree of tubular damage parallels the impairment of renal function. Once nephronic degeneration or tubular damage is established, it cannot be reversed or repaired by currently available treatment, and renal function deteriorates to renal failure, which is often life threatening. Renal damage and failure can only be managed through dialysis or organ transplantation.

Dialysis dependency is one of the leading causes of morbidity and mortality in the world. Despite advancement in understanding the pathophysiology of renal diseases, the incidence of end-stage renal disease is increasing. Approximately 600 patients per million receive chronic dialysis each year in the United States, at an average cost approaching $60,000-$80,000 per patient per year. Of the new cases of end-stage renal disease each year, approximately 28-33% are due to diabetic nephropathy (or diabetic glomerulopathy or diabetic renal hypertrophy), 24-29% are due to hypertensive nephrosclerosis (or hypertensive glomerulosclerosis), and 15-22% are due to glomerulonephritis. The 5-year survival rate for all chronic dialysis patients is approximately 40%, but for patients over 65, the rate drops to approximately 20%.

A need remains, therefore, for treatments that will prevent the progressive loss of renal function which has caused almost two hundred thousand patients in the United States alone to become dependent upon chronic dialysis, and which results in the premature deaths of tens of thousands each year.

SUMMARY OF INVENTION

The present invention provides protein-based renal therapeutic agents for administration to subjects in, or at risk of, renal failure. The methods and compositions of the present invention may be used to prevent, inhibit, delay, or reverse nephronic degeneration, which otherwise leads to the need for renal replacement therapy to prevent death. Specifically, the present invention is directed to compositions and methods that regulate the interaction between SOST and WISE proteins with their natural receptors. Exemplary natural receptors for WISE and SOST proteins include, but are not limited to, LRP5, LRP6, and BMP molecules. Methods and compositions of the present invention therefore provide a therapy that may reverse nephronic degeneration and/or prevent the progressive loss of renal function, thereby preventing premature death.

Methods of the invention include administering a therapeutically effective amount of an antibody to a patient in which the antibody specifically binds a peptide having at least 75%, 80%, 85%, 90%, 95%, 99% or more identity to at least 5, 8, 10, 15, 20 or more contiguous amino acids of a developmental regulator and the antibody interferes with the interaction between at least two developmental regulators thereby providing nephron protection and/or regeneration. Exemplary developmental regulators include those molecules disclosed as SEQ ID NOS: 1-217.

In some embodiments of the invention, the developmental regulators are a ligand and the ligand's natural receptor. For example, the ligand may be WISE and a known WISE receptor, such as LRP5, LRP6, BMP2, or BMP7. Another exemplary pair is SOST protein and one or more of its known receptors, e.g., LRP5, LRP6, BMP6, or BMP7.

The invention also provides a pharmaceutical composition for administration to a subject that includes an antibody and optional excipient(s). Antibodies suitable for the present invention may be administered in a therapeutically effective amount resulting in an improvement of renal function by at least 10%, 15%, 20%, 25%, or more following renal insult, as measured by a standard assay of renal function. Examples of such assays are provided herein. For example, a suitable assay of renal function include, determining rates of increase in Blood Urea Nitrogen (BUN) levels, rates of increase in serum creatinine, static measurements of BUN, static measurements of serum creatinine, glomerular filtration rates (GFR), ratios of BUN/creatinine, and serum concentrations of sodium (Na+). Suitable excipients include, but are not limited to, saline, buffered saline, dextrose, water, glycerol, ethanol, and combinations thereof.

Antibodies of the invention may be monoclonal, polyclonal, humanized, or a fragment thereof (Fab or Fab$_2$), as described in greater detail, below. Preferably, antibodies of the present invention specifically bind a peptide having at least 75%, 80%, 85%, 90%, 95%, 99% or more identity to at least 5, 8, 10, 15, 20 or more contiguous amino acids of a developmental regulator and the antibody interferes with the interaction between at least two developmental regulators thereby providing nephron protection and/or regeneration. More preferably, the antibody specifically binds a peptide having at least 75%, 80%, 85%, 90%, 95%, 99% or more identity to at least 5, 8, 10, 15, 20 or more contiguous amino acids of or encoded by SEQ ID NOS. 2, 4, 6, 8, 10, 12, 14, 15-18, 20, 85-87, 91, 93, 95, 98, 101, 103, 105, and 109-217; preferably SEQ ID NOS. 90-108, 215, and 216; more preferably, SEQ ID NOS. 19-89, 15-18, and 217; preferentially, SEQ ID NOS. 90-93, 215, and 216; alternatively, SEQ ID NOS. 15-20 and 217; more preferably, SEQ ID NOS. 92, 93, and 215; more preferably SEQ ID NOS. 15-18 and 217; ideally, SEQ ID NOS. 15-18. Alternatively, the antibody specifically binds a peptide having at least 75%, 80%, 85%, 90%, 95%, 99% or more identity to at least 5, 8, 10, 15, 20 or more contiguous amino acids of positions 50-62, 68-80, or 83-98 of SEQ ID NOS. 20, and 215-217.

The method and pharmaceutical composition of the invention may be administered to any subject receiving renal injury, chemical or physical insult resulting in apoptosis or necrosis of renal tissue, disease, or those otherwise at risk of chronic renal failure. For example, subjects in, or at risk of, chronic renal failure, or at risk of the need for renal replacement therapy, include but are not limited to the following: subjects which may be regarded as afflicted with chronic renal failure, end-stage renal disease, chronic diabetic nephropathy, hypertensive nephrosclerosis, chronic glomerulonephritis, hereditary nephritis, and/or renal dysplasia; subjects having a biopsy indicating glomerular hypertrophy, tubular hypertrophy, chronic glomerulosclerosis, renal cell carcinoma, and/or chronic tubulointerstitial sclerosis; subjects having an ultrasound, MRI, CAT scan, or other non-invasive examination indicating renal fibrosis.

The methods and compositions of the present invention may be utilized for any mammalian subject. For example, human subjects or patients, domesticated mammals (e.g., dogs, cats, horses), mammals with significant commercial value (e.g., dairy cows, beef cattle, sporting animals), mammals with significant scientific value (e.g., captive or free specimens of endangered species), or mammals which otherwise have value.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd Ed. 1994); *The Cambridge Dictionary of Science and Technology* (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG). See also, Pierce Catalog and Handbook, 1994-1995 (Pierce Chemical Co., Rockford, Ill.). See also, e.g., Kuby, J., *Immunology,* 3rd Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol:* 5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

An antibody immunologically reactive with a particular antigen can be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

The term "insult" refers to any injury or damage to a cell or population of cells that results in cell death or apoptosis, necrosis, altered kidney function, or decreased kidney function. An insult may have a variety of causes including, but not limited to, disease, chemical injury, or physical injury.

The phrase "specifically binds" when referring to a protein or peptide, refers to a binding reaction that is determinative of the presence of the protein, in a heterogeneous population of proteins and other biologics. Thus, under designated immunoassay conditions, the specified antibodies bind to a particular protein sequence at least two times the background and more typically more than 10 to 100 times background.

Specific recognition by an antibody under such conditions requires an antibody that is selected for its specificity for a particular protein. For example, antibodies raised against a particular protein, polymorphic variants, alleles, orthologs, and conservatively modified variants, or splice variants, or portions thereof, can be selected to obtain only those polyclonal antibodies that are specifically immunoreactive with WISE/SOST-like peptides such as those exemplified by SEQ ID NOS: 2, 4, 6, 8, 10, 12, 14, 15-18, 20-82, 85-87, 91, 93, 95, 98, 101, 103, 105, 109-217 and not with other random proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

The terms "identical" or percent "identity," in the context of two or more nucleic acids or polypeptide sequences, refer to two or more sequences or subsequences that are the same or have a specified percentage of amino acid residues or nucleotides that are the same as measured using a BLAST or BLAST 2.0 sequence comparison algorithm with default parameters described below, or by manual alignment and visual inspection. Such sequences are said to be "substantially identical" when they have about 60% identity, preferably 70%, 75%, 80%, 85%, 90%, 91%, 92%, 93%, 94%, 95%, 96%, 97%, 98%, 99%, or higher identity over a specified region, once compared and aligned for maximum correspondence over a comparison window or designated region. This definition also refers to, or may be applied to, the complement of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

The phrase "conditions suitable for protein binding" refers to those conditions (in terms of salt concentration, pH, detergent, protein concentration, temperature, etc.) which allow for binding to occur between a protein and its binding partner in solution. The conditions are not so lenient that a significant amount of nonspecific protein binding occurs.

As used herein, the term "developmental regulators" refers to molecules associated with the Wnt and BMP signaling pathways. Specifically, the term refers to the ligands and receptors responsible for regulating the Wnt and BMP signaling pathways including, but not limited to, LRP5, LRP6, BMP2, BMP4, BMP6, and BMP7. For example, several of these developmental regulators are provided by SEQ ID NOS: 1-217 as presented in the present application.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. I graphically illustrates inhibition of SOST association with LRP6. Relative LRP6 binding to variants of SOST was measured following immunoprecipitation. SOST variants M1, M2, M3, and M8 significantly exhibited reduced binding to LRP6 compared to wild type SOST.

DETAILED DESCRIPTION

I. Introduction

The present invention provides compositions and methods of using certain protein-based renal therapeutic agents that surprisingly prevent, inhibit, delay or alleviate the progressive loss of renal function. In a preferred embodiment, the present invention is suitable for treatment of renal disease.

In some forms, renal disease is caused by aberrant signal transduction during kidney development. The kidney develops from the ureteric bud, extending out from a pre-existing epithelial tube, giving rise to the branched collecting duct system while the surrounding metanephric mesenchyme undergoes mesenchymal-epithelial transition to form the proximal parts of the nephron. Signaling by members of the Wnt, BMP and FGF protein families, mediate this nephrogenesis by adjusting the balance between the ureteric bud epithelium, stromal and nephrogenic tissues. Inappropriate alteration of the balance of these signaling pathways, gives rise to renal disease. For example, over-activation of the Wnt pathway leads to cancer development (e.g. Wilms tumor), while inhibition of BMP signaling results in nephronic degeneration, both ultimately leading to renal failure.

WISE and/or SOST signaling also influences mature kidney tissue homeostasis, particularly in the case of renal damage or disease. In certain embodiments of the present invention, renal disease or damage is mitigated or reversed by administering to a patient antibodies that perturb or block the association of WISE and/or SOST to its receptor molecules in vivo. For example, administration of antibodies that mimick the WISE and/or SOST association with LRP5 or LRP6 may be used to subdue over-activated Wnt signaling in the treatment of kidney cancer. Alternatively, the association of WISE and/or SOST with BMP6, BMP7, and/or BMP2 may be inhibited to allow BMA signaling, which may result in protection from nephronic injury and/or promotion of nephronic regeneration.

II. Biological Assays of the Invention

The phrase "nephronic degeneration" refers to deterioration of an individual's kidney in which kidney or renal function is diminished as result of tissue necrosis or apoptosis by at least 5% preferably 10%, 15%, 20%, 25%, 30%, 40% 50% or more from the range of normal values medically determined for the individual. Nephronic degeneration can result from physical insult, chemical insult, or disease. The presence of nephronic degeneration can be measured by assays well known to those of ordinary skill of the art, such as elevation of serum creatinine levels or decrease in creatinine clearance (see, Brenner and Lazarus (1994), in HARRISON'S PRINCIPLES OF INTERNAL MEDICINE, 13th edition, Isselbacher et al., eds., McGraw Hill Text, N.Y.). Preferably a decrease of 5%, more preferably 10%, 15%, 20%, 25%, 30%, 40%, 50% or more of creatinine clearance compared to normal levels marks nephronic degeneration. Likewise, a 5% elevation of serum creatinine levels, more preferably 10%, 15%, 20%, 25%, 30%, 40%, 50% or more compared to normal levels indicates nephronic degeneration.

The phrase "nephron protection" refers to an in vivo phenomenon that protects against and prevents degeneration of nephronic or renal function caused by physical insult, chemical insult, or disease. As such, nephron protection refers to an in vivo phenomenon that inhibits elevation of serum creatinine levels or decrease in creatinine clearance by at least 5% preferably 10%, 15%, 20%, 25%, 30%, 40% 50% or more from the range of elevated values medically determined for the individual. Nephron protection also encompasses regeneration or repair of degenerate nephronic function caused by tissue necrosis or apoptosis resulting from physical insult, chemical insult, or disease. The regeneration or repair of degenerate nephronic function can be measured by assays well known to those of ordinary skill of the art, such as serum creatinine levels or creatinine clearance. Preferably an increase of 5%, more preferably 10%, 15%, 20%, 25%, 30%, 40%, 50% or more of creatinine clearance compared to normal levels marks nephronic protection. Likewise, a 5% decrease of serum creatinine levels, more preferably a 10%, 15%, 20%, 25%, 30%, 40%, 50% or more compared to normal levels indicates nephronic protection.

Assays of renal function are well known to those of ordinary skill of the art and include, without being limited to, rates of increase in Blood Urea Nitrogen (BUN) levels, rates of increase in serum creatinine, static measurements of BUN, static measurements of serum creatinine, glomerular filtration rates (GFR), ratios of BUN/creatinine, serum concentrations of sodium (Na+), urine/plasma ratios for creatinine, urine/plasma ratios for urea, urine osmolality, daily urine output, and the like (see, Brenner and Lazarus (1994), in HARRISON'S PRINCIPLES OF INTERNAL MEDICINE, 13th edition, Isselbacher et al., eds., McGraw Hill Text, N.Y.). Exemplary normal levels are as follows: serum creatinine levels of 0.8 to 1.4 mg/dL; BUN levels of 5 to 20 mg/dL; GFR score of 90 mL/min or more; BUN/Creatinine ratio of 10:1 to 20:1 and up to 30:1 in infants under 12 months of age; and serum sodium levels of 135 to 145 mEq/L. A skilled artisan will recognize that the normal ranges may vary with age, muscle mass, gender, weight, body surface area, and other characteristics. An "improvement" in one of the assays of renal function refers to an increase or decrease in level that is closer to the normal range. For example, a 10% improvement of a serum creatinine level of 0.2 mg/dL would be a serum creatinine level of 0.22 mg/dL, while a 10% improvement of a serum creatinine level of 3.0 mg/dL would be a serum creatinine level of 2.7 mg/dL.

III. Therapeutic Compositions

The present invention is directed to compositions and methods that regulate the interaction between SOST and WISE proteins with their natural receptors, particularly LRP5, LRP6, and BMP molecules. The renal therapeutic agents of the invention include, but are not limited to, peptides, proteins, antibodies, and small molecules derived from the WISE/SOST and LRP/BMP families and resultantly regulate Wnt and BMP signaling. For example, any peptide of at least 20, preferably 25, 30, 35, 40, 50 or more amino acids encoded by SEQ ID NO: 2, 4, 6, 8, 10, 12, 14, 15-18, 20-82, 85-87, 91, 93, 95, 98, 101, 103, 105, 109-217, or any fragment of any sequence thereof, may be used to raise antibodies, derive peptides, or derive small molecules suitable for antagonizing the interaction between SOST and WISE proteins with their natural receptors.

Such peptides may provide the basis of therapeutics by their inherent properties. For example, as inhibitors of renal damage, blocking peptides that antagonize the interaction between SOST and WISE proteins with their natural receptors may be useful. Further, peptides that activate SOST and WISE natural receptors by mimicking the necessary interaction between SOST or WISE and their natural receptors may also be useful. Exemplary antagonizing or activating peptides may include those provided by SEQ ID NOS: 21-82 or fragments of SEQ ID NOS: 2, 4, 6, 8, 10, 12, 14, 15-18, 20, 85-87, 91, 93, 95, 98, 101, 103, 105, 109-217.

A. Peptides and Proteins

Proteins and peptides useful to the invention may be isolated from natural sources, prepared synthetically or recombinantly, or any combination of the same using techniques well known to those of skill in the art. Generally, any purification protocol suitable for isolating proteins and known to those of skill in the art can be used. For example, affinity purification, column chromatography techniques, precipitation protocols and other methods for separating proteins may be used (see, e.g., Scopes, Protein Purification: Principles and Practice (1982); and U.S. Pat. No. 4,673, 641). Further, peptides may be produced synthetically using solid phase techniques and other techniques known to those skilled in the art (see, Barany, G. and Merrifield, R. B. *Solid Phase Peptide Synthesis* in PEPTIDES, Vol. 2, Academic Press, New York, N.Y., pp. 100-118 (1980)). Peptides and proteins of the invention may also be available commercially, or may be produced commercially.

B. Antibodies

The renal therapeutic agents of the present invention may be antibodies that recognize developmental regulator proteins, polypeptides, amino acid sequences, or fragments thereof. Suitable antibodies include those that recognize the WISE/SOST and LRP/BMP families and resultingly regulate Wnt and BMP signaling, such as those described in U.S. application Ser. No. 11/508,701 and incorporated herein by reference. For example, antibodies of the invention will recognize proteins or amino acid sequences encoding developmental regulators or fragments thereof, such as, but not limited to, those provided by SEQ ID NOS: 2, 4, 6, 8, 10, 12, 14, 15-18, 20-82, 85-87, 91, 93, 95, 98, 101, 103, 105, 109-217. More preferably, the antibody specifically binds a peptide having at least 75%, 80%, 85%, 90%, 95%, 99% or more identity to at least 5, 8, 10, 15, 20 or more contiguous amino acids of or encoded by SEQ ID NOS. 2, 4, 6, 8, 10, 12, 14, 15-18, 20, 85-87, 91, 93, 95, 98, 101, 103, 105, and 109-217; more preferably SEQ ID NOS. 90-108, 215, and 216; more preferably, SEQ ID NOS. 19-89, 15-18, and 217; more preferably, SEQ ID NOS. 90-93, 215, and 216; more preferably, SEQ ID NOS. 15-20 and 217; more preferably, SEQ ID NOS. 92, 93, and 215; more preferably SEQ ID NOS. 15-18 and 217; more preferably, SEQ ID NOS. 15-18. Alternatively, the antibody specifically binds a peptide having at least 75%, 80%, 85%, 90%, 95%, 99% or more identity to at least 5, 8, 10, 15, 20 or more contiguous amino acids of positions 50-62, 68-80, or 83-98 of SEQ ID NOS. 20, and 215-217.

When the above family of amino acid sequences, including WISE and SOST, are allowed to bind to their natural receptors, renal regeneration is repressed. When the above-mentioned family of amino acid sequences are prevented from binding to their natural receptors, renal regeneration will increase. Thus, the present invention relates to tools and methods used to inhibit or mimic the binding of the WISE/SOST family to their natural receptors.

1. Antigen Specificity and Production

The present invention provides at least one antibody that inhibits interaction between Wnt or BMP antagonistic ligands (developmental regulators) with LRP or BMP receptors, thus promoting constitutive Wnt or BMP signaling and renal regeneration. Suitable antibodies are obtained by immunizing a host animal with peptides, or antigens, that are all or a portion of the subject protein of the presently claimed invention. The antigen may be the complete protein, or fragments and derivatives thereof. For example, a suitable antigen may have at least 75%, 80%, 85%, 90%, 95%, 98%, 99% or 100% identity to at least 5, 8, 10, 12, 15, 20, or 25 contiguous amino acids of a protein encoded by SEQ ID NOS: 2, 4, 6, 8, 10, 12, 14, 15-18, 20-82, 85-87, 91, 93, 95, 98, 101, 103, 105, 109-217. More preferably, the antibody specifically binds a peptide having at least 75%, 80%, 85%, 90%, 95%, 99% or more identity to at least 5, 8, 10, 15, 20 or more contiguous amino acids of or encoded by SEQ ID NOS. 2, 4, 6, 8, 10, 12, 14, 15-18, 20, 85-87, 91, 93, 95, 98, 101, 103, 105, and 109-217; more preferably SEQ ID NOS. 90-108, 215, and 216; more preferably, SEQ ID NOS. 19-89, 15-18, and 217; more preferably, SEQ ID NOS. 90-93, 215, and 216; more preferably, SEQ ID NOS. 15-20 and 217; more preferably, SEQ ID NOS. 92, 93, and 215; more preferably SEQ ID NOS. 15-18 and 217; more preferably, SEQ ID NOS. 15-18. Alternatively, the antibody specifically binds a peptide having at least 75%, 80%, 85%, 90%, 95%, 99% or more identity to at least 5, 8, 10, 15, 20 or more contiguous amino acids of positions 50-62, 68-80, or 83-98 of SEQ ID NOS. 20, and 215-217.

Some exemplary embodiment of the present invention includes antibodies that inhibit, block, or otherwise interfere with the specific binding of an LRP or BMP molecule to a Wnt or BMP antagonistic ligand. A skilled artisan will recognize that an antigen may be selected to generate an antibody that interferes by specifically binding to the LRP or BMP molecule or by specifically binding to the Wnt or BMP antagonistic ligand. The selected antigen will result in an antibody that will specifically bind to WISE-like or SOST-like proteins and prevent the interaction of WISE-like or SOST-like proteins with LRP5, LRP6, BMP2, BMP6, or BMP7. in alternative examples, a selected antigen will result in an antibody that will specifically bind to LRP5, LRP6, or BMP molecules and prevent the interaction with WISE-like or SOST-like proteins.

Suitable amounts of well-characterized antigen for production of antibodies can be obtained using standard techniques known in the art such as, but not limited to, cloning or synthetic synthesis. Antigenic proteins can be obtained from transfected cultured cells that overproduce the antigen of interest. For example, expression vectors that have nucleotide sequences encoding an antigen of interest can be constructed, transfected into cultured cells, and then the antigen can be subsequently isolated using methods well-known to those skilled in the art (see, Wilson et al., *J. Exp. Med* 173:137, 1991; Wilson et al., *J. Immunol.* 150:5013, 1993). Alternatively, DNA molecules encoding an antigen of choice can be obtained by synthesizing DNA molecules using mutually priming long oligonucleotides (see, Ausubel et al., (eds.), *Current Protocols In Molecular Biology*, pages 8.2.8 to 8.2.13, 1990; Wosnick et al., *Gene* 60:115, 1987; and Ausubel et al. (eds.), *Short Protocols In Molecular Biology*, 3rd Edition, pages 8-8 to 8-9, John Wiley & Sons, Inc., 1995). As a skilled artisan will recognize, established techniques using the polymerase chain reaction provide the ability to synthesize antigens (Adang et al., *Plant Molec. Biol.* 2/:1131, 1993; Bambot et al., *PCR Methods and Applications* 2:266, 1993; Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263 268, Humana Press, Inc. 1993). Once produced, the antigen of choice is used to generate antigen specific antibodies.

2. Antibody Production

The present invention provides antibodies as renal therapeutic agents. It is envisioned that such antibodies include, but are not limited to, polyclonal, monoclonal, humanized, part human, or fragments thereof. A skilled artisan will appreciate the benefits and disadvantages of the type of antibody used for therapeutic treatment and will further recognize the selection is dependent upon the intended use.

a. Polyclonal Antibodies

Means for preparing and characterizing polyclonal antibodies are well known to those skilled in the art (see, e.g., *Antibodies: A Laboratory Manual*, Cold Spring Harbor Laboratory, 1988; incorporated herein by reference). For example, for the preparation of polyclonal antibodies, the first step is immunization of the host animal with the target antigen, where the target antigen will preferably be in substantially pure form, with less than about 1% contaminant. The antigen may include the complete target protein, fragments, or derivatives thereof. To prepare polyclonal antisera an animal is immunized with an antigen of interest, and antisera is collected from that immunized animal. A wide range of animal species can be used for the production of antisera. Typically the animal used for production of anti-antisera is a rabbit, mouse, rat, hamster, guinea pig or goat. Because of the relatively large blood volume of rabbits, a rabbit is a preferred choice for the production of polyclonal antibodies.

The amount of antigen used in the production of polyclonal antibodies varies upon the nature of the antigen as well as the animal used for immunization. A variety of routes can be used to administer the antigen of choice; subcutaneous, intramuscular, intradermal, intravenous, intraperitoneal and intrasplenic. The production of polyclonal antibodies may be monitored by sampling blood of the immunized animal at various points following immunization. A second, booster injection, may also be given. The process of boosting and titering is repeated until a suitable titer is achieved. When a desired titer level is obtained, the immunized animal can be bled and the serum isolated and stored. The animal can also be used to generate monoclonal antibodies, as is well known to those skilled in the art.

The immunogenicity of a particular composition can be enhanced by the use of non-specific stimulators of the immune response, known as adjuvants. Exemplary adjuvants include complete Freund's adjuvant, a non-specific stimulator of the immune response containing killed *Mycobacterium tuberculosis*; incomplete Freund's adjuvant; and aluminum hydroxide adjuvant.

It may also be desired to boost the host immune system, as may be achieved by associating the antigen with, or coupling the antigen to, a carrier. Exemplary carriers include keyhole limpet hemocyanin (KLH) and bovine serum albumin (BSA). Other albumins such as ovalbumin, mouse serum albumin or rabbit serum albumin can also be used as carriers. As is also known in the art, a given composition may vary in its immunogenicity.

b. Monoclonal Antibodies

Monoclonal antibodies (Mabs) may be readily prepared through use of well-known techniques to those skilled in the art, such as those exemplified in U.S. Pat. No. 4,196,265, incorporated herein by reference. Typically, this technique involves immunizing a suitable animal with the selected antigen. The antigen is administered in a manner effective to stimulate antibody-producing cells. Rodents such as mice and rats are preferred animals, however, the use of rabbit, sheep and frog cells is also possible.

By way of example, following immunization the somatic cells with the potential for producing antigen specific antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The anti-antigen antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas).

Any one of a number of myeloma cells may be used, as are known to those of skill in the art (Goding, pp. 65 66, 1986; Campbell, pp. 75 83, 1984; each incorporated herein by reference). For example, where the immunized animal is a mouse, one may use P3-X63/Ag8, X63-Ag8.653, NS1/1.Ag 41, Sp210-Ag14, FO, NSO/U, MPC-11, MPC11-X45-GTG 1.7 and S194/5XX0 Bul; for rats, one may use R210.RCY3, Y3-Ag 1.2.3, IR983F, 4B210 or one of the above listed mouse cell lines; and U-266, GM1500-GRG2, LICR-LON-HMy2 and UC729-6, are all useful in connection with human cell fusions.

The heterogeneous cell population may be cultured in the presence of a selection medium to select out the hybridoma cells. A suitable selection medium includes an inhibitor of de novo synthesis, such as aminopterin in HAT medium, methotrexate in HMT medium, or azaserine in AzaH medium plus the necessary purine and/or pyrimidine salvage precursors (i.e. hypoxanthine and thymidine in HAT or HMT media; hypoxanthine in AzaH medium). Only cells capable of operating nucleotide salvage pathways are able to survive in the selection medium. The myeloma cells are defective in key enzymes of the salvage pathway, e.g., hypoxanthine phosphoribosyl transferase (HPRT), and cannot survive. The B cells can operate this pathway, but they have a limited life span in culture and generally die within about two weeks. Therefore, the only cells that can survive in the selective media are those hybrids formed from myeloma and B cells (hybridomas).

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired anti-antigen reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual anti-antigen antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations.

MAbs produced by either means will generally be further purified, e.g., using filtration, centrifugation and various chromatographic methods, such as HPLC or affinity chromatography, all of which purification techniques are well known to those of skill in the art. These purification techniques each involve fractionation to separate the desired antibody from other components of a mixture. Analytical methods particularly suited to the preparation of antibodies include, for example, protein A-Sepharose and/or protein G-Sepharose chromatography.

c. Humanized Antibodies

Also of interest are humanized antibodies. Methods of humanizing antibodies are known in the art. The humanized antibody may be the product of an animal having transgenic human immunoglobulin constant region genes (see for example International Patent Applications WO 90/10077 and WO 90/04036, both incorporated herein by reference). Alternatively, the antibody of interest may be engineered by recombinant DNA techniques to substitute the CH1, CH2, CH3, hinge domains, and/or the framework domain with the corresponding human sequence (see WO 92/02190 and incorporated herein by reference).

The use of Ig cDNA for construction of chimeric immunoglobulin genes is known in the art (Liu et al. P.N.A.S. 84:3439, 1987 and incorporated herein by reference). mRNA is isolated from a hybridoma or other cell producing the antibody and used to produce cDNA. The cDNA of interest may be amplified by the polymerase chain reaction using specific primers (see U.S. Pat. Nos. 4,683,195 and 4,683,202, both incorporated herein by reference). Alternatively, a library is made and screened to isolate the sequence of interest. The DNA sequence encoding the variable region of the antibody is then fused to human constant region sequences. The sequences of human constant region genes may be found in Kabat et al. Sequences of Proteins of Immunological Interest, N.I.H. publication no. 91-3242, 1991 and incorporated herein by reference. Human C region genes are readily available from known clones. The chimeric, humanized antibody is then expressed by conventional methods known to those of skill in the art.

d. Antibody Fragments

Antibody fragments, such as Fv, F(ab')2 and Fab may be prepared by cleavage of the intact protein, e.g. by protease or chemical cleavage. Alternatively, a truncated gene is designed. For example, a chimeric gene encoding a portion of the F(ab')2 fragment would include DNA sequences encoding the CH1 domain and hinge region of the H chain, followed by a translational stop codon to yield the truncated molecule. The following patents and patent applications are specifically incorporated herein by reference for the preparation and use of functional, antigen-binding regions of antibodies, including scFv, Fv, Fab', Fab and F(ab')$_2$ fragments: U.S. Pat. Nos. 5,855,866; 5,965,132; 6,051,230; 6,004,555; and 5,877,289.

Also contemplated are diabodies, which are small antibody fragments with two antigen-binding sites. The fragments may include a heavy chain variable domain ($V_H$) connected to a light chain variable domain ($V_L$) in the same polypeptide chain ($V_H V_L$). By using a linker that is too short to allow pairing between the two domains on the same chain, the domains are forced to pair with the complementary domains of another chain and create two antigen-binding sites. Techniques for generating diabodies are well known to those of skill in the art and are also described in EP 404,097 and WO 93/11161, each specifically incorporated herein by reference. Also, linear antibodies, which can be bispecific or monospecific, may include a pair of tandem Fd segments ($V_H C_{H1}$-$V_H C_{H1}$) that form a pair of antigen binding regions may be useful to the invention as described in Zapata et al. (1995), and incorporated herein by reference.

C. Compositions

The renal therapeutic agents contemplated herein can be expressed from intact or truncated genomic or cDNA or from synthetic DNAs in prokaryotic or eukaryotic host cells by techniques well known to those of skill in the art. Exemplary host cells include, without limitation, prokaryotes including E. coli, or eukaryotes including yeast, Saccharomyces, insect cells, or mammalian cells, such as CHO, COS or BSC cells. One of ordinary kill in the art will appreciate that other host cells can be used to advantage.

The term "construct" as used herein refers to a nucleic acid sequence containing at least one polynucleotide encoding a polypeptide of the invention operably linked or fused to additional nucleic acids. Such constructs include vectors, plasmids, and expression cassettes encoding at least one polynucleotide encoding a polypeptide of the invention. It is also envisioned that constructs could be polynucleotides encoding a polypeptide of the invention fused to other protein coding sequence to generate fusion proteins as known to those of skill in the art.

Constructs can be inserted into mammalian host cells by methods known to those of skill in the art including, but not limited to, electroporation, transfection, microinjection, micro-vessel transfer, particle bombardment, biolistic particle delivery, liposome mediated transfer and other methods described in Current Protocols in Cell Biology, Unit 20, pub. John Wiley & Sons, Inc., 2004 and incorporated herein by reference.

III. Therapeutic Uses

A. Subjects for Treatment

Renal therapeutic agents of the invention may be used in subjects that have received renal injury, or those at risk of chronic renal failure. As used herein, a subject is said to be in, or at risk of, chronic renal failure, or at risk of the need for renal replacement therapy (i.e., chronic hemodialysis, continuous peritoneal dialysis, or kidney transplantation), if the subject is reasonably expected to suffer a progressive loss of renal function associated with progressive loss of functioning nephron units. Whether a particular subject is in, or at risk of, chronic renal failure is a determination which may routinely be made by one of ordinary skill in the relevant medical or veterinary art. Subjects in, or at risk of, chronic renal failure, or at risk of the need for renal replacement therapy, include but are not limited to the following: subjects which may be regarded as afflicted with chronic renal failure, end-stage renal disease, chronic diabetic nephropathy, hypertensive nephrosclerosis, chronic glomerulonephritis, hereditary nephritis, and/or renal dysplasia; subjects having a biopsy indicating glomerular hypertrophy, tubular hypertrophy, chronic glomerulosclerosis, renal cell carcinoma, and/or chronic tubulointerstitial sclerosis; subjects having an ultrasound, MRI, CAT scan, or other non-invasive examination indicating renal fibrosis; subjects having an unusual number of broad casts present in urinary sediment; subjects having a GFR which is chronically less than about 50%, and more particularly less than about 40%, 30% or 20%, of the expected GFR for the subject; human male subjects weighing at least about 50 kg and having a GFR which is chronically less than about 50 ml/min, and more particularly less than about 40 ml/min, 30 ml/min or 20 ml/min; human female subjects weighing at least about 40 kg and having a GFR which is chronically less than about 40 ml/min, and more particularly less than about 30 ml/min, 20 ml/min or 10 ml/min; subjects possessing a number of functional nephron units which is less than about 50%, and more particularly less than about 40%, 30% or 20%, of the number of functional nephron units possessed by a healthy but otherwise similar subject; subjects which have a single kidney; and subjects which are kidney transplant recipients.

The methods and compositions of the present invention may be utilized for any mammalian subject. Such mammalian subjects include, but are not limited to, human subjects or patients. Exemplary subjects may also include domesticated mammals (e.g., dogs, cats, horses), mammals with significant commercial value (e.g., dairy cows, beef cattle, sporting animals), mammals with significant scientific value (e.g., captive or free specimens of endangered species), or mammals which otherwise have value.

B. Excipients

The renal therapeutic agents of the invention, alone or conjugated, may be formulated according to methods known to those skilled in the art to prepare pharmaceutically useful compositions, whereby the therapeutic agents are combined in a mixture with a pharmaceutically acceptable carrier or excipient. A composition is said to be a "pharmaceutically acceptable carrier" if its administration can be tolerated by a recipient patient and preserves the activity of the active component, in this case the renal therapeutic agent. Exemplary carriers include, but are not limited to, saline, buffered saline, dextrose, water, glycerol, ethanol, and combinations thereof. The formulation should suit the mode of administration. Other suitable carriers are well known to those skilled in the art (see, REMINGTON'S PHARMACEUTICAL SCIENCES, 19th Ed., 1995). Upon formulation, the antibody or immunoconjugate solutions will be administered in a manner compatible with the dosage formulation and in such amount as is therapeutically effective.

C. Dosage

In general, the dosage of administered renal therapeutic agents will vary depending upon such factors as the patient's age, weight, height, sex, general medical condition and previous medical history. For example, it is typically desirable to provide the recipient with a dosage of an antibody component, which is in the range of from about 1 μg/kg to 10 mg/kg (amount of agent/body weight of patient), although a lower or higher dosage also may be administered as circumstances dictate. Range finding studies may be conducted to determine appropriate dosage by techniques known to those skilled in the art and as described in *Current Protocols in Pharmacology*, Unit 10, pub. John Wiley & Sons, 2003 and incorporated herein by reference. A skilled artisan will recognize the therapeutically effective amount for each active compound may vary with factors including, but not limited to, the activity of the compound used, stability of the active compound in the recipient's body, the total weight of the recipient treated, the route of administration, the ease of absorption, distribution, and excretion of the active compound by the recipient, the age and sensitivity of the recipient to be treated, the type of tissue, and the like.

For purposes of therapy, renal therapeutic agents are administered to a patient in a therapeutically effective amount in a pharmaceutically acceptable carrier. In this regard, a "therapeutically effective amount" is one that is physiologically significant. An agent is physiologically significant if its presence results in a detectable change in the physiology of a recipient patient. In the present context, an agent is physiologically significant if its presence results in a clinically significant improvement in an assay of renal function when administered to a mammalian subject (e.g., a human patient). Such assays of renal function are well known to those of skill in the art and include, without being limited to, rates of increase in Blood Urea Nitrogen (BUN) levels, rates of increase in serum creatinine, static measurements of BUN, static measurements of serum creatinine, glomerular filtration rates (GFR), ratios of BUN/creatinine, serum concentrations of sodium (Na+), urine/plasma ratios for creatinine, urine/plasma ratios for urea, urine osmolality, daily urine output, and the like (see, Brenner and Lazarus (1994), in HARRISON'S PRINCIPLES OF INTERNAL MEDICINE, 13th edition, Isselbacher et al., eds., McGraw Hill Text, N.Y.)

Additional pharmaceutical methods may be employed to control the duration of action of an antibody in a therapeutic application. Control release preparations can be prepared through the use of polymers to complex or adsorb the renal therapeutic agent. For example, biocompatible polymers include matrices of poly(ethylene-co-vinyl acetate) and matrices of a polyanhydride copolymer of a stearic acid dimer and sebacic acid (Sherwood et al., *Bio/Technology* 10:1446, 1992). The rate of release of an agent from such a matrix depends upon the molecular weight of the protein, the amount of agent within the matrix, and the size of dispersed particles (Saltzman et al., *Biophys. J.* 55:163, 1989; Sherwood et al., *Bio/Technology* 10:1446, 1992). Other solid dosage forms are described in REMINGTON'S PHARMACEUTICAL SCIENCES, 19th ed. (1995) and can be prepared by techniques known to those skilled in the art.

D. Routes of Administration

Administration of renal therapeutic agents to a patient can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses. Intravenous injection provides a useful mode of administration due to the thoroughness of the circulation in rapidly distributing antibodies.

E. Methods for Testing Renal Therapeutic Agents

The renal therapeutic agents of the present invention may be tested in animal models of chronic renal failure or nephronic degeneration. Mammalian models of nephronic degeneration in, for example, mice, rats, guinea pigs, cats, dogs, sheep, goats, pigs, cows, horses, and non-human primates, may be created by causing an appropriate direct or indirect injury or insult to the renal tissues of the animal. For example, animal models of nephronic degeneration may be created by administering cisplatin, which causes nephrotoxicity and reduced creatinine clearance. Animal models of nephronic degeneration may also be created by performing a partial (e.g., 5/6) nephrectomy which reduces the number of function nephron units to a level which initiates compensatory renal hypertrophy, further nephron loss, and the progressive decline in renal function (see, Vukicevic, et al. *J. Bone Mineral Res.* 2:533, 1987). Alternatively, animal models of renal cell carcinoma may be generated by subcapsular renal injection of renal carcinoma (RENCA) cells that results in the development of primary tumors with subsequent development of metastases in the lungs, lymph nodes, and spleen (see, Hillman, G. G., Droz, J., and Haas, G. H. *In Vivo*, 8: 77-80, 1994). The above-described animal models may be generated by techniques well-known to those of skill in the art.

The renal therapeutic agents may be administered to the above-described animal models and markers of renal function can be monitored (see, Examples 1-3). Preferably kidney function is determined using markers of renal function such as Blood Urea Nitrogen (BUN) levels, serum creatinine levels, or glomerular filtration. Exemplary renal therapeutic agents will result in a decrease of BUN or serum creatinine levels or increase in glomerular filtration rate compared to control animals. Control animals will be animal models treated with a control solution not containing the renal therapeutic agent being tested, preferably a non-irritating buffer solution or other carrier.

IV. Kits

The present invention provides articles of manufacture and kits containing materials useful for treating the pathological conditions described herein. The article of manufacture may include a container of a medicament as described herein with a label. Suitable containers include, for example, bottles, vials, and test tubes. The containers may be formed from a variety of materials such as glass or plastic. The container holds a composition having an active agent which is effective for treating, for example, diseases characterized by nephronic degeneration. Alternatively, the container may hold a composition that includes a nephronic degeneration-inducing agent. The active agent in the composition is a renal therapeutic agent of the invention, including a peptide, protein, antibody, small molecule, or an agent such as a vector or cell preparation capable of allowing production of a renal therapeutic agent in vivo. The label on the container indicates that the composition is used for treating nephronic degenerative diseases, or malignant diseases, and may also indicate directions for administration and monitoring techniques, such as those described above.

The kit of the invention includes the container described above and a second container, which may include a pharmaceutically acceptable diluent. It may further include other materials desirable from a commercial and user standpoint, including other buffers, diluents, filters, needles, syringes, and package inserts with instructions for use.

EXAMPLES

As can be appreciated from the disclosure provided above, the present invention has a wide variety of applications. Accordingly, the following examples are offered for illustration purposes and are not intended to be construed as a limitation on the invention in any way. Those of skill in the art will readily recognize a variety of non-critical parameters that could be changed or modified to yield essentially similar results.

Example 1. WISE/SOST Antibody Production

SOST and Wise both share the same gene structure, and produce a secreted protein whose second exon encodes a cystein knot. Molecular dissection of SOST at the amino acid level revealed putative LRP5/6 binding sites located in the first arm of the cystein knot. An immunoprecipitation assay of Flag tagged SOST variants and LRP6 was used to confirm which of these sites were necessary for LRP5/6 binding. Variants of SOST were generated with mutations at positions 60-62 (M1), 78-81 (M2), 89-90 (M3), 100-103 (M4), 140-143 (M7), and 162-166 (M8s). An immunoprecipitated western blot of Flag tagged SOST was mixed with LRP6-IgG and was quantified using phosphor-imager and its software ImageQuant. SOST variants M1, M2 and M3 showed a significant loss of binding ability to LRP6 (FIG. 1), thus indicating potential sites for mediating the block between SOST and its natural binding partners including LRP5/6, BMP6, and BMP7.

In order to block the binding of SOST to LRP 5/6, BMP6, or BMP7 inhibitory antibodies were generated that recognize the altered amino acids of SOST variants M1, M2, and M3. Specific epitopes targeting these amino acids were identified using antigenic hydrophobic plots. These plots revealed that the best sites for generation of an antibody were between amino acids 50-62, 68-80, and 83-98 of SEQ ID NO. 215 and 217. The resultant peptides selected as antigens to produce antibodies are listed in SEQ ID NOS 15-18 and were used to generate monoclonal antibodies.

The peptides of SEQ ID NO 15-18 were used to immunize mice. Following immunization, B lymphocytes (B cells) were obtained from peripheral blood samples. The B cells from the immunized mice were then fused with murine myeloma cells to produce hybridomas. The cells were cultured in HAT medium with hypoxanthine and thymidine to select out the hybridoma cells. Hybridomas were then cultured by single-clone dilution in microtiter plates, followed by ELISA testing of the individual clonal supernatants for desired anti-antigen reactivity. There were 27 ELISA positive monoclonal antibodies generated against SOST.

Example 2. Acute Renal Failure Treatment

Acute renal failure manifests itself immediately following renal insult or injury. Therapeutics of the present invention may be analyzed for use as a treatment for preventing or reversing acute renal failure.

Mice subjected to partial nephrectomies or decapsulation may be used as models of nephronic degeneration to test renal therapeutic agents of the invention (see, Vukicevic, et al. *J. Bone Mineral Res.* 2:533, 1987). A partial nephrectomy involves removing one kidney and 2/3 of the remaining kidney. After initial dramatic increases in plasma creatinine and BUN levels indicating an acute failure phase, the levels decline to an elevated level compared to normal levels. Approximately two weeks following surgery, the elevated level gradually increases with time as the animal progresses to chronic renal failure. Decapsulation is a mock surgery in which the kidneys are decapsulated but no renal tissue is removed or nephronic injury introduced. Decapsulated mice may be used as controls for kidney functionality comparison.

To determine if a renal therapeutic agent of the invention can prevent or delay the effects of acute renal failure, nephrectomized and decapsulated mice that have immediately recovered from their respective surgeries may be used. Mice may be divided into six groups as follows: 1) nephrectomized, receiving renal therapeutic agent; 2) nephrectomized, receiving vehicle buffer only; 3) nephrectomized, receiving no treatment; 4) decapsulated, receiving renal therapeutic agent; 5) decapsulated, receiving vehicle buffer only; and 6) decapsulated, receiving no treatment. Group one can be further divided into mice receiving 1, 3, 10, or 50 μg/kg body weight of renal therapeutic agent. Prior to or during the acute failure phase, nephrectomized mice may be administered their respective treatment by intraperitoneal injection twice daily for at least three days. Serum creatinine levels should be monitored prior to surgery, immediately following surgery, each day of treatment, and for each of at least four days following the last injection.

A decrease in serum creatinine levels in nephrectomized mice treated with a therapeutic agent of the invention may indicate a successful candidate for further testing of preventing nephronic degeneration or inducing nephronic regeneration. An increase in serum creatinine levels beyond increases of serum creatinine levels of vehicle-only treated mice may indicate a therapeutic agent capable of inducing nephronic degeneration. Such an agent may be useful in treating renal cell carcinoma or other kidney cancer type.

Example 3. Chronic Renal Failure Treatment

Chronic renal failure manifests itself progressively following an initial acute renal failure phase or renal insult without concomitant acute renal failure. Therapeutics of the present invention may be analyzed for use as a treatment for preventing or reversing chronic renal failure.

To determine if a therapeutic agent of the invention may prevent the development of chronic renal failure, nephrectomized and decapsulated mice that have recovered from their respective surgeries for at least two weeks may be used. Animals surviving the surgery for two weeks are past the acute renal failure phase and have not yet entered chronic renal failure.

Mice may be divided into six groups as follows: 1) nephrectomized, receiving renal therapeutic agent; 2) nephrectomized, receiving vehicle buffer only; 3) nephrectomized, receiving no treatment; 4) decapsulated, receiving renal therapeutic agent; 5) decapsulated, receiving vehicle buffer only; and 6) decapsulated, receiving no treatment. Group one can be further divided into mice receiving 1, 3, 10, or 50 µg/kg body weight of renal therapeutic agent. Mice may be treated intraperitoneally at least three times per week for a period of approximately 6-9 weeks. Serum creatinine levels should be monitored prior to treatment, during the treatment period, and at least 1 week following the treatment period.

During weeks 1-5 of treatment, nephrectomized mice may exhibit elevated serum creatinine levels compared to decapsulated mice. The amount of elevation between the groups of nephrectomized mice may correlate with the course of treatment used. If the serum creatinine levels are less elevated with increasing amounts of the renal therapeutic agent being tested, then the agent may be a successful candidate for further tests of preventing nephronic degeneration and inducing nephronic regeneration. If the serum creatinine levels become increasingly elevated with increasing amounts of the renal therapeutic agent in decapsulated mice, then the agent may be a nephronic degeneration inducing agent. Such an agent may be useful in treating renal cell carcinoma or other kidney cancer type.

Example 4. Renal Cell Carcinoma Treatment

Constitutive activation of the Wnt signaling pathway may be involved in the development of renal cell carcinoma and other kidney cancer types. The renal therapeutic agents of the invention that result in ectopic activation of the Wnt signaling pathway via interaction with the natural receptors of WISE and SOST may be useful in therapies treating renal cell carcinoma or other kidney cancer types. Therapeutics of the present invention may be analyzed for use as a treatment for preventing or reversing kidney cancer types.

To investigate novel therapeutic strategies for the treatment of human renal cell carcinoma, such as adoptive immunotherapy or cytokine therapy, murine renal cell carcinoma has been a particularly suitable animal model for assessing novel therapeutic approaches (Sayers, T. J., Wiltrout, T. A., McCormick, K., Husted, C., and Wiltrout, R. H., *Cancer Res.*, 50: 5414-5420, 1990; Salup, R. R., and Wiltrout, R. H. *Cancer Res.*, 46: 3358-3363, 1986). In this model, primary kidney tumors are induced by subcapsular renal injection of renal carcinoma (RENCA) cells with subsequent development of metastases in the lungs, lymph nodes, and spleen (Hillman, G. G., Droz, J., and Haas, G. H. *In Vivo*, 8: 77-80, 1994).

Murine RENCA cells originally obtained from a tumor that arose spontaneously in the kidney of BALB/c mice may be injected into BALB/c mice to generate a renal cell carcinoma model. Histologically, RENCA is a granular cell type adenocarcinoma, which is pleomorphic with large nuclei. Monolayers of murine RENCA cells may be grown in RPMI 1640 with phenol red supplemented with 10% FCS, 2 mM L-glutamine, 100 units penicillin/ml, and 100 µg of streptomycin/ml. RENCA cells may be cultured in a humidified atmosphere of 95% air and 5% carbon dioxide at 37° C.

Female BALB/c mice approximately 6-8 weeks of age (approximate weight, 20 g) may be injected with RENCA cells in 0.2-ml aliquots into the subcapsular space of the left kidney performed through a flank incision after the animals are anesthetized with 0.5-1.5 volume percent isoflurane, which may be used in combination with an oxygen flow of 1.5 l/min. The subcapsular renal injection of RENCA cells in a syngeneic BALB/c mouse may be followed by the progressive development of a primary tumor mass in the left kidney. One week after application, the primary tumor may be macroscopically visible; after 10 days, spontaneous metastases may develop in the regional lymph nodes, in the lung, the peritoneum, and the liver, allowing the RENCA model to be staged similarly to human renal cell carcinoma. The mean survival time of RENCA-bearing mice may be 32 days after RENCA cells are injected.

Treatments with a renal therapeutic agent of the invention or vehicle only may be initiated 1 day after tumor cell inoculation into the subcapsular space of the left kidney. Mice receiving the renal therapeutic agent may receive about 1, 3, 10, or 50 µg/kg body weight of the renal therapeutic agent intraperitoneally at least three times per week for a period of approximately 6-9 weeks. Serum creatinine levels should be monitored prior to treatment, during the treatment period, and at least 1 week following the treatment period. Animal weights should be taken every other day.

Two or 3 weeks after starting treatment, 6 or 10 mice, respectively, may be sacrificed in each group for determination of weight and volume of primary tumors, weight, and number of metastasis of the lung and metastasis formation in the abdominal lymph nodes. The volumes of primary tumors taken macroscopically may be calculated by taking and multiplying the distances of all three dimensions. The number of metastases in the lung and abdominal lymph nodes may be counted using a dissection microscope. In the abdominal cave, all visible lymph nodes may be counted for detection of metastasis, knowing that in healthy animals visible lymph nodes are usually absent. More animals may be sacrificed at later time points to monitor the progression or regression of tumor development.

A renal therapeutic agent of the invention that results in a significant decrease in primary tumor size or number of metastasis compared to mice treated with vehicle only may be successful candidates for renal cell carcinoma therapy. Agents that do not result in a significant decrease or result in a significant increase in primary tumor size or number of metastasis may be successful candidates for preventing nephronic degeneration or promoting nephronic regeneration.

SEQUENCE LISTING

The Sequence Listing, in computer readable form (CRF), is submitted on compact disc, and is hereby incorporated by reference into this patent application. A total of 217 sequences are being submitted.

What is claimed is:

1. An isolated antibody that specifically binds to the contiguous amino acids contained in amino acid numbers 50-62 or 68-80 of SEQ ID NO: 216.

2. The isolated antibody of claim 1, wherein the antibody is selected from the group consisting of a monoclonal antibody, a polyclonal antibody, a Fv fragment of an antibody, a Fab fragment of an antibody, a F(ab')$_2$ fragment of an antibody, a recombinant single chain Fv fragment (scFv), a diabody, a triabody, and a tetrabody.

3. The isolated antibody of claim 2, wherein the antibody is a monoclonal antibody.

4. The isolated antibody of claim 1, wherein the antibody is a monoclonal antibody.

5. An isolated antibody that specifically binds to amino acid numbers 83-98 of SEQ ID NO: 216.

6. The isolated antibody of claim 5, wherein the antibody is a monoclonal antibody.

* * * * *